US008535641B2

(12) United States Patent
Weichert et al.

(10) Patent No.: US 8,535,641 B2
(45) Date of Patent: *Sep. 17, 2013

(54) **PHOSPHOLIPID ANALOGS AS DIAPEUTIC\* AGENTS AND METHODS THEREOF**

(75) Inventors: Jamey Weichert, Fitchburg, WI (US); Marc Longino, Verona, WI (US); Anatoly Pinchuk, Madison, WI (US)

(73) Assignee: Cellectar, Inc., Madison, WI (US)

( \* ) Notice: Subject to any disclaimer, the term of this patent is extended or adjusted under 35 U.S.C. 154(b) by 1250 days.

This patent is subject to a terminal disclaimer.

(21) Appl. No.: 10/906,687

(22) Filed: Mar. 2, 2005

(65) Prior Publication Data

US 2005/0196339 A1 Sep. 8, 2005

Related U.S. Application Data

(60) Provisional application No. 60/521,166, filed on Mar. 2, 2004.

(51) Int. Cl.
*A61K 51/00* (2006.01)
*A61M 36/14* (2006.01)

(52) U.S. Cl.
USPC ....... 424/1.85; 424/1.11; 424/1.65; 424/1.81; 424/9.1

(58) Field of Classification Search
USPC .................. 424/1.11, 1.37, 1.65, 1.73, 1.81, 424/1.85, 1.89, 9.1, 9.3, 9.4, 9.5, 9.6, 9.7, 424/9.8; 558/70, 153, 166, 168, 169, 170
See application file for complete search history.

(56) References Cited

U.S. PATENT DOCUMENTS

| | | | |
|---|---|---|---|
| 4,925,649 A | 5/1990 | Counsell | |
| 4,965,391 A | 10/1990 | Counsell | |
| 5,087,721 A \* | 2/1992 | Counsell et al. | 558/166 |
| 5,347,030 A | 9/1994 | Counsell | |
| 5,369,097 A | 11/1994 | Salari | |
| 5,626,654 A | 5/1997 | Breton et al. | |
| 5,795,561 A | 8/1998 | Counsell et al. | |
| 5,965,108 A \* | 10/1999 | Dean | 424/1.69 |
| 6,255,519 B1 | 7/2001 | Counsell et al. | |
| 6,417,384 B1 | 7/2002 | Counsell | |
| 6,503,478 B2 | 1/2003 | Chaiken et al. | |
| 7,041,859 B1 | 5/2006 | Kabalka | |
| 7,220,539 B1 | 5/2007 | Du et al. | |
| 7,632,644 B2 | 12/2009 | Weichert et al. | |
| 7,700,075 B2 \* | 4/2010 | Weichert et al. | 424/9.3 |
| 7,893,286 B2 | 2/2011 | Pinchuk et al. | |
| 2002/0065429 A1 | 5/2002 | Counsell | |
| 2006/0013767 A1 | 1/2006 | Weichert et al. | |
| 2006/0115426 A1 | 6/2006 | Weichert et al. | |
| 2006/0228298 A1 | 10/2006 | Weichert et al. | |
| 2007/0020178 A1 | 1/2007 | Weichert et al. | |
| 2007/0098633 A2 | 5/2007 | Weichert et al. | |
| 2008/0075660 A1 | 3/2008 | Weichert et al. | |
| 2008/0207492 A1 | 8/2008 | Polt et al. | |
| 2008/0312459 A1 | 12/2008 | Pinchuk et al. | |
| 2010/0316567 A1 | 12/2010 | Weichert et al. | |
| 2011/0064660 A1 | 3/2011 | Pinchuk et al. | |
| 2011/0064661 A1 | 3/2011 | Pinchuk et al. | |
| 2012/0156133 A1 | 6/2012 | Pinchuk et al. | |

FOREIGN PATENT DOCUMENTS

| | | |
|---|---|---|
| CA | 2276284 A1 | 6/1998 |
| WO | WO 98/24480 A1 | 6/1998 |
| WO | WO 2005/063774 A1 | 7/2005 |
| WO | WO 2005/084716 A2 | 9/2005 |
| WO | WO 2006/014589 A2 | 2/2006 |
| WO | WO 2007/013894 A2 | 2/2007 |

OTHER PUBLICATIONS

Stedman's Medical Dictionary 27th Edition, the term therapy; copyright© 2000 Lippincott Williams & Wilkins.\*
Golub et al., Science, Oct. 15, 1999, pp. 531-537.\*
Counsell et al, Isotope Production and Applications in the 21st Century, Proceedings of the International Conference on Isotopes, 3rd, Vancouver, BC, Canada, Sep. 6-10, 1999 (2000), Meeting Date 1999, 163-166.\*
Nijsen et al (Radioactive holmium loaded poly(L-lactic acid) microspheres for treatment of hepatic malignancies: efficacy in rabbits, Thesis, 2001, Chapter 7).\*
Arthur, G., Bittman, R. Biochim Biophys Acta. 1998; 1390:85-102.
Becher, R. et al., Onkologie-Germany (1993)16:1(11-15).
Berdel, W. E. et al., Onkologie-Germany (1992)15:238-242.
Counsell, R. E., et al., (1990)31:3(332-336).
Counsell, R.E., Quart J Nucl Med. 1997; 41(suppl 1):14-16.
Curley, SA, et al., Ann Surg 1999;230:1-8.
De Gramont, A, et al., J Clin Oncol 1997; 15:808-815.
Fong, Y, et al., Ann Surg 1999; 230:309-318.
Giacchetti, S., et al. Journal of Clinical Oncology 2000; 18:136-147.
Greven, K., et al., Cancer Journal Scientifica American 1997;3:353-357.
Ike, H., et al., Dis Colon Rectum 2002; 45:468-473.
Imboden, M., et al., Cancer Res 2001; 61:1500-1507.
Kallman, Robert F. ed, Pergamon Press, New York, pp. 111-132, 1987.
Lencioni, R., et al., Abdom Imaging 2001; 26:345-360.
Longino, M. A. et al., Molecular Imaging 2004, 3(3), (Abstract #337).
Mayr, N. A. et al., International Journal of Radiation Oncology, Biology, Physics 2002; 52;1:14-22.
Meta-Analysis: Modulation of fluorouracil by leucovorin in patients with advanced colorectal cancer: evidence in terms of response rate. Advanced Colorectal Cancer Meta-Analysis Project. J Clin Oncol 1992; 10:896-903.
Moser, A.R. et al., Online Aug. 15-18, 2003 Presentation No. 305.
O'Dwyer, P.J, et al., Seminars in Oncology 2001; 28:Suppl-9, (pp. 45-49).
Penna, C, Nordlinger B. Burg Clin North Am 2002; 82: 1075-1090.

(Continued)

*Primary Examiner* — D L Jones
(74) *Attorney, Agent, or Firm* — Wolf, Greenfield & Sacks, P.C.

(57) ABSTRACT

The present invention provides methods and uses of phospholipid ether analogs as diagnostic and therapeutic agents for numerous cancers.

5 Claims, 23 Drawing Sheets

(56) References Cited

OTHER PUBLICATIONS

Pickhardt, P. J., et al., NE J Med (2003)349:23(2191-2200.
Plotzke, K. P., et al., J Nucl Med. 1993; 34(5):787-792.
Plotzke, K.P., et al., Int J RadPart B, Nucl Med & Biology. 1992; 19(7):765-773.
Rampy, M. A., et al., J Nucl Med. 1996; 37(9):1540-1545.
Rampy, M.A., et al., J Med Chem. 1995; 38:3156-3162.
Saltz, L. B., et al., N Engl J Med 2000; 343:905-91.
Snyder, F., Wood, R., Cancer Research. 1969; 29:251-257.
Snyder, F., et al., Biochem Biophys Acta. 1969; 176:502-510.
Solbiati, L., et al., Radiology 2001;221:159-166.
Stahl, A., et al., Abdominal Imaging (2004) 29:3(388-397).
Terwogt, J.M.M. et al., British Jrnl of Cancer (1999) 79(1158-1161).
Weber, S. M., et al.,Ann Surg Oncol 1999; 6:186-194.
Weichert, J. P., et al., Int J Appl Rad Isotopes. 1986; 37:907-913.
Weichert, J. P., et al., Molecular Imaging Online (2004)3:3(269-270).
Pinchuk, A., et al., J Med Chem 2006, 49:2155-2165.
Weichert, J. P.,et al., J Med Chem 1995; 38:636-646.
Wichmann, M. W., et al., Anticancer Research 2000; 20:4953-4955.
Zasadny, K. R., et al., J Nucl Med, 1999; 40(5):39P.
International Preliminary Report on Patentability for PCT/US2010/048340 mailed Mar. 22, 2012.
European Office Action for Application No. 08010321.1 dated May 8, 2012.
European Office Action for Application No. 08020805.1 dated May 3, 2012.
Office Communication for U.S. Appl. No. 12/879,093 mailed May 3, 2012.
Partial European Search Report for EP 08010321.1 mailed Jul. 13, 2009.
Extended European Search Report for EP 08010321.1 mailed Oct. 6, 2009.
Extended European Search Report for EP 08020805.1 mailed Jul. 14, 2009.
Invitation to Pay Additional Fees for PCT/US2005/006681 mailed Nov. 8, 2005.
International Search Report and Written Opinion for PCT/US2005/006681 mailed Feb. 20, 2006.
International Preliminary Report on Patentability for PCT/US2005/006681 mailed Sep. 14, 2006.
International Search Report and Written Opinion for PCT/US2005/024259 mailed Mar. 1, 2006.
International Preliminary Report on Patentability for PCT/US2005/024259 mailed Jan. 18, 2007.
International Search Report and Written Opinion for PCT/US2005/047657 mailed Jan. 22, 2007.
International Preliminary Report on Patentability for PCT/US2005/047657 mailed Jul. 5, 2007.
International Search Report and Written Opinion for PCT/US2010/048340 mailed Oct. 14, 2010.
Invitation to Pay Additional Fees for PCT/US2010/038294 mailed Jul. 23, 2010.
International Search Report and Written Opinion for PCT/US2010/048351 mailed Oct. 19, 2010.
Written Opinion for PCT/US2007/017885 dated Jul. 31, 2008.
International Search Report for PCT/US2007/017885 mailed Aug. 14, 2008.
International Preliminary Report on Patentability for PCT/US2007/017885 mailed Feb. 26, 2009.
Canadian Office Action for Application No. 2557698 dated Dec. 8, 2010.
Chinese Office Action for Application No. 200580007056.9 dated Mar. 6, 2009.
European Office Action for Application No. 05729873.9 dated Apr. 26, 2007.
Summons to Attend Oral Proc for Application No. 05729873.9 dated Jan. 22, 2008.
European Office Action for Application No. 05729873.9 dated Jun. 16, 2008.
European Office Action for Application No. 05729873.9 dated Mar. 23, 2009.
Israeli Office Action for Application No. 177645 dated Aug. 13, 2009.
Israeli Office Action for Application No. 177645 dated May 13, 2010.
Indian Office Action for Application No. 4875/DELNP/2006 dated Jun. 7, 2011.
Japanese Office Action for Application No. 2007-501917 dated Dec. 7, 2010.
Japanese Office Action for Application No. 2007-501917 dated Sep. 13, 2011.
Mexican Office Action for Application No. PA/a/2006/009681 dated Nov. 20, 2008.
New Zealand Office Action for Application No. 549562 dated Mar. 5, 2009.
New Zealand Office Action for Application No. 549562 dated Sep. 23, 2009.
New Zealand Office Action for Application No. 549562 dated Dec. 1, 2009.
New Zealand Office Action for Application No. 549562 dated Jan. 12, 2010.
Australian Office Action for Application No. 2005-269861 dated Jan. 13, 2010.
Chinese Office Action for Application No. 200580026935.6 dated May 8, 2009.
Chinese Office Action for Application No. 200580026935.6 dated Nov. 27, 2009.
European Office Action for Application No. 05769481.2 dated Dec. 21, 2007.
Israeli Office Action for Application No. 180363 dated Sep. 13, 2009.
New Zealand Office Action for Application No. 552914 dated Apr. 24, 2009.
New Zealand Office Action for Application No. 552914 dated Nov. 17, 2009.
New Zealand Office Action for Application No. 552914 dated Dec. 2, 2009.
Office Communication for U.S. Appl. No. 11/177,749 mailed Apr. 1, 2009.
Notice of Allowance for U.S. Appl. No. 11/177,749 mailed Nov. 23, 2009.
European Office Action for Application No. 05858499.6 dated Oct. 9, 2007.
Mexican Office Action for Application No. MX/a/2007/007497 dated Apr. 5, 2010.
Office Communication for U.S. Appl. No. 11/316,620 mailed Apr. 2, 2009.
Office Communication for U.S. Appl. No. 11/316,620 mailed Nov. 12, 2009.
Office Communication for U.S. Appl. No. 11/316,620 mailed Jun. 22, 2010.
Office Communication for U.S. Appl. No. 11/316,620 mailed Mar. 10, 2011.
Office Communication for U.S. Appl. No. 11/316,620 mailed Oct. 13, 2011.
Notice of Allowance for U.S. Appl. No. 12/156,287 mailed Oct. 12, 2010.
Office Communication for U.S. Appl. No. 11/382,645 mailed Apr. 22, 2009.
Notice of Allowance for U.S. Appl. No. 11/382,645 mailed Sep. 24, 2009.
Office Communication for U.S. Appl. No. 11/671,403 mailed Apr. 6, 2009.
Office Communication for U.S. Appl. No. 11/891,939 mailed Dec. 3, 2008.
[No Author Listed] Database Registry RN 208986-86-9 Jul. 26, 1998. 1 page.
[No Author Listed] Iodine. The Merck Index. Merck & Co., Inc. 1989:794.
Brownstein, Clinical Experience with Inorganic, Non-radioactive Iodine-Iodide. The Original Internist. 2005:105-8.
Chia et al., Abberations in Phospholipase D Activity-A Pharmacological Target for Cancer Detection. The FASEB Journal. 2006;20:A488. Abstract 330.10.

Clezy et al., The Chemistry of Pyrrolic Compounds. VIII. Dipyrrylthiones. Aust J Chem. 1969;22:239-49.

Goud et al., Synthesis of 8-heteroatom-substituted 4,4-difluoro-4-bora-3a, 4a-diaza-s-indacene dyes (BODIPY). Tetrahedron. 2006;62:5084-91.

Hunt et al., Assessment of the aggregation state of integral membrane proteins in reconstituted phospholipid vesicles using small angle neutron scattering. J Mol Biol. Nov. 14, 1997;273(5):1004-19.

Jhanwar et al., Current status of therapy of solid tumors. J Nucl Med. Jan. 2005;46 Suppl 1:141S-50S.

Jurcic et al., Radiolabeled anti-CD33 monoclonal antibody M195 for myeloid leukemias. Radiolabeled anti-CD33 monoclonal antibody M195 for myeloid leukemias. Cancer Res. Dec. 1, 1995;55(23 Suppl):5908s-5910s.

Kamigaki et al., Therapy and imaging of pancreatic carcinoma xenografts with radioiodine-labeled chimeric monoclonal antibody A10 and its Fab fragment. Jpn J Cancer Res. Dec. 1995;86(12):1216-23.

Kuerschner et al., Polyene-lipids: a new tool to image lipids. Nat Methods. Jan. 2005;2(1):39-45. Epub Dec. 21, 2004.

Liebeskind et al., Heteroaromatic thioether-boronic acid cross-coupling under neutral reaction conditions. Org Lett. Mar. 21, 2002;4(6):979-81.

Longino et al., Preliminary Clinical Imaging and Pharmacokinetic Results with NM404 in Non-Small Cell Lung Cancer. Presentation abstract. Presented at the 5th International Symposium on Radiohalogens meeting in Whistler, B.C. Sep. 11-15, 2004. Last accessed on Jul. 13, 2011 at http://legacyweb.triumf.ca/5ISR/5ISR%20Abstracts.pdf.

Longino et al., Preliminary Clinical Imaging and Pharmacokinetic Results with NM404 in Non-Small Cell Lung Cancer. Presented at the 5th International Symposium on Radiohalogens meeting in Whistler, B.C. Sep. 11-15. Slideshow presentation on Sep. 15, 2004. Last accessed on Jul. 13, 2011 at http://legacyweb.triumf.ca/5ISR/44-CS29-NM404%20Imaging%20&%20PK.pdf. 20 pages.

Maier et al., Fluorescent lipid probes: some properties and applications (a review). Chem Phys Lipids. Jun. 2002;116(1-2):3-18.

Meyer et al., Potential tumor or organ-imaging agents. 30. Radioiodinated phospholipid ethers. J Med Chem. Sep. 1989;32(9):2142-7.

Miyagawa et al., Imaging of HSV-tk Reporter gene expression: comparison between [18F]FEAU, [18F]FFEAU, and other imaging probes. J Nucl Med. Apr. 2008;49(4):637-48. Epub Mar. 14, 2008.

Murray et al., Phase II radioimmunotherapy trial with 131I-CC49 in colorectal cancer. Cancer. Feb. 1, 1994;73(3 Suppl):1057-66.

Nakabeppu et al., Radionuclide therapy of malignant pheochromocytoma with 131I-MIBG. Ann Nucl Med. Nov. 1994;8(4):259-68.

Noh et al., Overexpression of phospholipase D1 in human breast cancer tissues. Cancer Lett. Dec. 20, 2000;161(2):207-14. Abstract only. Previously Cited As Dong-Young.

Oshimoto et al., Increased activity and expression of phospholipase D2 in human colorectal cancer. Oncol Res. 2003;14(1):31-7. Abstract only. 4 pages.

Pickhardt et al., Microcomputed tomography colonography for polyp detection in an in vivo mouse tumor model. Proc Natl Acad Sci U S A. Mar. 1, 2005;102(9):3419-22. Epub Feb. 22, 2005.

Plotzke et al., Biodistribution, metabolism, and excretion of radioiodinated phospholipid ether analogs in tumor-bearing rats. J Nucl Biol Med. Dec. 1993;37(4):264-72.

Quon, et al., "Flying through" and "flying around" a PET/CT scan: Pilot study and development of 3D integrated 18F-FDG PET/CT for virtual bronchoscopy and colonoscopy. J Nucl Med. Jul. 2006;47(7):1081-7.

Rampy et al. Synthesis and biological evaluation of radioiodinated phospholipid ether analogs. Nucl Med Biol. May 1995;22(4):505-12.

Sandgren et al., Evaluation of 125I-NM404 in a Spontaneous Murine Pancreatic Adenocarcinoma Model. Aug. 2003, 2nd Annual Meeting of the Society of Molecular Imaging.

Sik Min et al., Neoplastic transformation and tumorigenesis associated with overexpression of phospholipase D isozymes in cultured murine fibroblasts. Carcinogenesis. Oct. 2001;22(10):1641-7.

Wagner et al., Boron-dipyrromethene dyes for incorporation in synthetic multi-pigment light-harvesting arrays. Pure & Appl Chem. 1996;68(7):1373-80.

Wang et al., Molecular imaging with 123I-FIAU, 18F-FUdR, 18F-FET, and 18F-FDG for monitoring herpes simplex virus type 1 thymidine kinase and ganciclovir prodrug activation gene therapy of cancer. J Nucl Med. Jul. 2006;47(7):1161-71.

Weichert et al., Specificity of NM404 for Hyperplasia versus Neoplasia in the ApcMin /+Endogenous Mammary Adenocarcinoma Model. 2nd Annual Meeting of the Society of Molecular Imaging. San Francisco. Aug. 15-18, 2003. Presentation No. 305. Abstract only. 1 page. Retrieved from the Internet on Jan. 27, 2006 at http://www.abstractsonline.com/viewer/viewAbstract.asp?CKey={175C0489-C808-47DF-B4EF-5CF57EE52265}&MKey={4C56C7C9-3CB4-404E-A0C1-3F37525A5245}&AKey={A4C6DD8F-4BF2-400D-97ED-20C14381CDBB}&SKey={0AAB7B18-F58E-4226-A5DF-755F3585A60F}.

Weichert, Noninvasive Evaluation of Colon Tumors in Live Mice using MicroCT Virtual colonoscopy. Academy of Molecular Imaging Meetings—Orlando. Mar. 18-23, 2005. Presented on Mar. 22, 2005. Slideshow presentation. 40 pages.

Office Communication for U.S. Appl. No. 11/316,620 mailed Dec. 21, 2012.

Office Communication for U.S. Appl. No. 12/813,992 mailed Jul. 27, 2012.

Office Communication for U.S. Appl. No. 12/813,992 mailed Feb. 28, 2013.

Office Communication for U.S. Appl. No. 12/879,167 mailed Oct. 5, 2012.

Office Communication for U.S. Appl. No. 13/403,445 mailed Oct. 3, 2012.

* cited by examiner

PHOSPHOLIPID ANALOGS AS DIAPEUTIC* AGENTS AND METHODS THEREOF

RELATED APPLICATION

The present application seeks priority from U.S. Provisional Application 60/521,166, filed on Mar. 2, 2004, which is incorporated herein by reference for all purposes.

BACKGROUND OF INVENTION

The invention generally relates to diagnostic imaging of tumors and specifically relates to diagnostic imaging of tumors using phospholipid analogs.

The early detection of cancer has been one of the primary goals of modern imaging technology, since the identification of a suspected tumor in a localized stage significantly improves the chances for successful treatment and elimination of the cancerous tissue. A large number of imaging strategies have therefore been designed, using a variety of techniques and modalities, to aid the physician in making an accurate diagnosis as early as possible.

Unfortunately, conventional imaging techniques such as computerized tomography (CT) and MRI (magnetic resonance imaging) are limited in their ability to afford a conclusive diagnosis of a suspected lesion, since they are only capable of observing differences in the density or morphology of tissues. A more invasive and costly biopsy procedure is often necessary to provide a definitive diagnosis. In contrast, nuclear medicine techniques such as positron emission tomography (PET) and single photon emission tomography (SPECT) can provide functional or biochemical information about a particular organ or area of interest. However, the success of these nuclear imaging techniques depends in large part on the selective uptake and detection of appropriate radiopharmaceuticals. Selective uptake, in turn, depends upon the development of radiopharmaceuticals with a high degree of specificity for the target tissue. Unfortunately, the tumor-localizing agents developed thus far for oncological applications have had only limited application.

For example, one of these prior art compounds, $^{67}Ga$ gallium citrate, was originally identified for its ability to accumulate in tumor tissue. Unfortunately, $^{67}Ga$ gallium citrate is taken up by a variety of other non-cancerous lesions as well, including inflammatory lesions, and unacceptable amounts of radioactivity can also accumulate in liver and spleen tissue. The rapid buildup of a radiopharmaceutical in these organs can seriously interfere with the imaging of nearby lesions and also negatively impacts the dosage that can safely be given to a patient.

An alternative approach has been to develop radiolabeled monoclonal antibodies (Mabs) directed to tumor-specific antigens. However, these monoclonal antibodies are specific only to the particular tumor tissue for which they have been produced, and therefore will not localize generally in neoplastic tissue. Moreover, the use of Mabs for diagnostic imaging has lead to additional problems, including varying degrees of antigen expression, low tumor uptake, non-specific binding and adverse immunogenic reactions.

In an attempt to address these problems, the present inventors have recently identified and developed a series of novel compounds demonstrating useful tumor specificity. See, e.g., U.S. Pat. Nos. 4,925,649; 4,965,391; 5,087,721; 5,347,030 and 6,417,384; all of which are herein incorporated by reference. It is believed that these radioiodinated phospholipid ether analogs take advantage of a unique biochemical characteristic of malignant tumor cells; i.e. the large concentration of naturally-occurring ether lipids in the tumor cell membranes relative to corresponding normal tissues. Although the precise mechanism of action is not fully understood, the prevailing hypothesis is that the phospholipid ether analogs become entrapped in tumor membranes. Accordingly, these compounds localize in tumor tissue and remain in place for diagnostic and/or therapeutic applications.

The selective retention of the radiolabeled phospholipid ether analogs described in the above patents has been demonstrated in a variety of rodent and animal tumor xenografts and not in spontaneous tumor models which are thought to more closely mimic the human disease. Unfortunately, the data obtained from these studies has also demonstrated a relatively rapid clearance of the radiopharmaceutical compound from the blood, and an undesirable accumulation by non-target tissues. As noted above, non-target tissue uptake can decrease the efficacy of radiodiagnostic imaging by creating high background activity, or by causing excessive exposure of radiosensitive tissues to the injected radioactivity.

Accordingly, there remains a significant need in the art for radiopharmaceuticals which exhibit a rapid clearance from non-target tissues as well as an extended half-life in the plasma, while still retaining its specificity and avidity for neoplastic tissue. Such an agent should not only assist in the non-invasive imaging of primary tumors and metastases, but should also serve as a carrier for a cytotoxic agent for site-specific eradication of malignant tumor tissue, especially as it relates to most frequently diagnosed forms of cancers. It is further desirable that radiopharmaceuticals are selective for malignant tumors and not precancerous tissues including adenomas and hyperplasia.

Approximately 147,000 new cases of colorectal cancer are diagnosed each year in the United States. Thus colorectal cancer is the fourth most common cancer, accounting for 60,000 deaths per year.[1] Treatment depends primarily on the cancer stage, but may include surgery, radiation, chemotherapy, and/or radiofrequency or cryo ablation. In routine follow-ups for colorectal cancer patients, however, determination of carcinoembryonic antigen (CEA), a colorectal tumor marker, and repeat colonoscopies[5] fail to detect recurrent disease in over 50% of patients.[6] Therefore, there is a need for development of additional methods for detection of recurrent disease. Further, during treatment and diagnosis using CT scanning and RF ablation, functional information from CT scans is difficult to obtain. With contrast-enhanced helical CT, the tumor vascularity may be assessed to some degree, but there is no way of accurately determining if viable tumor cells remain within the RF lesion. In addition, the thermal lesions created by RF normally have a rim of inflammation surrounding them on post procedure CT scans for up to 6 months post-procedure. PET scanning has been used to follow post-ablation patients, but the rim of inflammation surrounding RF thermal lesions normally displays increased uptake, even in the absence of viable tumor. This decreases the sensitivity and specificity for early detection of recurrent tumor. Accordingly, agents like NM404 that are selective for and retained indefinitely by malignant tumor cells are preferable, unlike FDG which is not selective for tumor cells and goes to infectious sites and hyperplasias (Barret's Esophagus). Moreover, compounds like NM404 containing $^{124}I$, which has a 4 day physical half-life and can be shipped anywhere in the world, are preferable as compared to FDG which has a 110 minute half-life and therefore may only be have limited distribution within 200 miles of the production site. Further compounds like NM404 that undergo prolonged retention (not metabolized) are preferable since it is more likely that they may have significant therapeutic potential when mated with an appropriate radioisotope like [131]I. Also, compounds like NM404, which can be labeled with a variety of iodine isotopes and have expanded versatility (diagnosis and therapy as well as a tool for experimental animal studies) are preferable as compared to FDG, which is limited to $^{18}$F for PET scanning or potentially [19]F (stable) for magnetic resonance imaging albeit at very low sensitivity levels. Regardless of its tumor targeting ability, FDG due to its rapid metabolism in tumor cells, does not have potential for therapy. Therefore, other compounds are needed to investigate post RF local recurrences. Likewise, if the tumor becomes metastatic, either by progression or recurrence of the local tumor, a hybrid imaging modality (PET and CT combination), replacing post-procedure separate CT and PET scanning is highly desirable.

Moreover, even where chemotherapy is the mode of treatment, improved monitoring of the response to chemotherapy is essential. Therefore, development of an early marker to study response to chemotherapy to allow physicians to quickly discontinue use of ineffective chemotherapeutic regimens without exposing patients to the toxicity of prolonged treatments is desirable. Where External Beam Radiation Therapy is an alternate treatment for patients with tumors of similar histology, tumors may have dramatically different responses to curative-intent external radiation therapy (XRT). Some patients with rectal cancer treated with pre-operative radiation will have a complete response, while others with similar histology (at the light microscopy level) will have a poor response to treatment and disease will recur. Response to radiation is a predictive factor for ultimate tumor control and survival for many cancers, including many gastrointestinal cancers, lung cancer, head and neck cancer, and gynecologic cancers. Most response characterization methods, while very predictive of response, are performed after completion of treatment. While some intra-treatment clinical assessments are useful in adjusting treatment,[14] in most cases there is no accurate method of predicting tumor response during actual treatment. Such a test, especially one applicable to a broad range of tumor sites and histologies, would obviously be very useful and desirable. Other treatment and diagnostic methods include molecular assays that have been proposed to predict response to therapy, and recent efforts include use of DNA microarrays to identify genetic changes that correlate with response or lack of response to treatment. These are investigational and none are in routine clinical use.

Yet other methods of diagnosis and treatment include use of imaging modalities to predict response during XRT treatment. Intra-treatment PET scans using FDG are under active investigation, wherein the isotope uptake in the primary tumor midway through radiation therapy is compared to the pre-treatment uptake. Several retrospective studies suggest patients with continued strong uptake during treatment have poorer tumor control outcomes than patients whose tumors are less FDG-avid during treatment.[15] However, more effect screening, diagnostic and treatment methods for various cancers are extremely desirable.

Other well observed tumors include malignant gliomas that are the most common type of primary brain tumors. Despite aggressive treatment with surgery, radiation, and chemotherapy, most patients harboring these tumors have less than a two-year survival after diagnosis. Recent advances in neuroradiology and magnetic resonance imaging (MRI) have made a significant impact in early diagnosis and treatment of these tumors. Most malignant gliomas, however, have an infiltrative component, which is poorly differentiated from edematous brain tissue by present imaging techniques. It is often this component of the tumor that is most difficult to treat and responsible for local recurrence. Undoubtedly, better visualization of invasive glioma cells is desirable for significant therapeutic treatment.

Likewise, pancreatic cancer is a highly lethal disease with the poorest likelihood of survival among all of the major malignancies. It is the fifth leading cause of cancer death in the United States and of all the newly diagnosed cancers in the United States, 2% per year are due to pancreatic cancer. However, it is one of the most highly lethal diseases which accounts for 5% of all cancer deaths. Miller B A, et al. NIH Pub. No. 96-4104. Bethesda, Md. 1996. This is demonstrated by the fact that there are no five-year survivors in patients with unresectable disease. In addition, although surgical resection offers the only hope for cure, the five-year survival after resection is only 20%. Geer R J, Brennan M F. Am J Surg 1993; 165:68-72; Yeo C J, Cameron J L, et al., Ann Surg 1997. Although PET scanning with 18-FDG has shown promise in imaging a variety of other primary cancers, it appears to have only limited ability to improve upon the imaging capability of CT scan for patients with pancreatic cancer, particularly in assessing for metastatic disease. Kasperk R K, Riesener K P, et al., World J Surg 2001; 25:1134-1139; Sendler A, Avril N, et al., World J Surg 2000; 24:1121-1129. Thus, there remains a need for a method of accurately imaging patients with occult metastatic pancreatic cancer.

Hepatocellular cancer is the most common solid organ malignancy worldwide, due to its common etiology of chronic liver damage from hepatitis or alcoholism. Incidence rates vary markedly, from 2.1 per 100,000 in North America to 80 per 100,000 in high-incidence regions of China. The risk of developing HCC in patients with cirrhosis is 1-6% per year. Although resection is the only curative option, only 10-30% of patients are candidates for surgery at the time of presentation, due to either poor hepatic reserve or the presence of unresectable or metastatic disease. Attesting to the aggressive nature of this disease, the five-year survival is only 15-35% after curative resection. Treiber G. Digestive Diseases (2001) 19:311-323.

Breast cancer is a major health concern for women in the United States today. It was anticipated that nearly 216,000 women in the US alone would be diagnosed with breast cancer in 2004 and of these 40,000 were expected to die. Accurate assessment of local, regional and distant metastatic spread is critical for optimal disease treatment and management. The development of a non-invasive imaging modality that would allow detection and or characterization of local or distant breast cancer metastases including lymph node involvement would represent a significant advancement in the management of this disease. Although mammography is the current screening method of choice for initial detection of breast cancer, histologic confirmation and regional spread to neighboring lymph nodes are typically evaluated via biopsy. More sophisticated imaging methods including scintigraphic scanning with [99m]Tc-Sestamibi and $^{18}$F-FDG PET scanning have now been extensively examined, but have not impacted treatment planning significantly due mainly to unpredictable specificity. Wahl R L. *Quart J of Nucl Med* (1998) 42:1-7. The role of PET scanning has indicated efficacy, however, in monitoring tumor response to chemotherapy. Smith I C, Welch A E, et al., *J of Clin Oncol* (2000) 18:1676-1688; Schelling M, Avril N, et al., *J of Clin Oncol* (2000) 18:1689-1695. Radiation therapy has a well-established role in the treatment of breast cancer due mainly to the sensitivity of many solid epithelial tumors, including infiltrating ductal carcinoma, to ionizing radiation. DeVita V, Hellman S, Rosenberg S. Cancer: Principles and Practice of Oncology, 6th edition. Philadelphia (Pa.): Lippincott, Williams and Wilkins, 2002, pp. 1667-1680. The most common indication for radiation in breast cancer is as adjuvant treatment following lumpectomy or mastectomy. In this context, radiation therapy has been shown to dramatically decrease the incidence of local and regional recurrence by sterilizing microscopic deposits in these tissues. Chemotherapy is offered when the patient has metastatic disease or is deemed to have an increased risk for occult metastases. In this latter indication, that of adjuvant chemotherapy administration, studies confirm improved survival in patients receiving adjuvant chemotherapy or hormonal therapy. Radiation is also used in the palliative setting with good effect in reducing the pain and volume effects of metastases in solid organs and bone. Many patients relapse after definitive therapy for reasons that are multifactorial. Acquired resistance to radiation and chemotherapy undoubtedly contributes to recurrence after primary therapy. Additionally, the use of radiation is associated with specific toxicities which are generally late-occurring and dose-limiting. Fibrosis, nerve damage, and soft tissue necrosis can be severe if excessive doses of radiation are used. Arm lymphedema is the most common and dreaded toxicity for breast cancer patients, and results most commonly from the combination of axillary dissection (done for diagnostic purposes) and adjuvant radiation to the axilla.

In contrast to new anticancer drugs that are largely targeted to receptors or molecules specific to each particular tumor type, new compounds that rely on a common mechanism applicable to a variety of different tumor types are extremely desirable.

Hence, there remains a dire clinical need for noninvasive breast cancer imaging techniques that afford both high sensitivity and specificity. Moreover, the potential to deliver a therapeutic dose of iodine-131 simultaneously to both primary and metastatic tumors is a significant added benefit.

Non-small cell lung cancer (NSCLC) is the leading cause of cancer death in the United States today. Surgical resection in appropriately selected patients offers the best chance for long-term survival and may be curative. Accurate pre-operative assessment of local, regional and distant metastatic spread is thus critical for optimal management. Evaluation of the mediastinal lymph node status is essential because nodal metastasis, which occurs in nearly half of all patients with NSCLC, is probably the most frequent barrier to cure. Accurate staging may also spare patients the morbidity of unnecessary, non-curative surgical procedures.

Imaging with FDG-PET scanning is quickly becoming the gold standard for imaging NSCLC, due to improved sensitivity rates, particularly when compared with CT imaging. However, this is an expensive imaging test which is not available in most community practices. Hence, there remains a need for an imaging technique which is sensitive, specific, and uses resources which are readily available to most patients.

Positron-emission tomography (PET) scanning with $^{18}$F-FDG has generated considerable interest as an imaging technique. A recent study prospectively compared the ability of a standard approach to staging for NSCLC (CT, ultrasound, bone scanning, etc) and PET scanning to detect metastases in mediastinal lymph nodes and distant sites. Pieterman R M, vanPutten J W G, Meuzzelaar J J, Mooyaart E L, Valburg W, Koeter G H, Fidler V, Prium J, Groen H J M. *Preoperative Staging of Non-Small Cell Lung cancer with Positron-Emission Tomography*. New Eng J Med 343:254-261, 2000. Mediastinal involvement was confirmed histopathologically, and distant metastases were confirmed by other imaging tests. The sensitivity and specificity of PET for detecting mediastinal metastases were 91% and 86%, respectively; for detecting distant metastases, 82% and 93%, respectively. This compares to sensitivity and specificity for CT scanning of mediastinal involvement 75% and 66%, respectively. Another study compared imaging with FDG-PET, CT, and histology results. Overall sensitivity, specificity, and accuracy of PET for staging mediastinal nodes (n=168 in 54 patients) was 96%, 93% and 94%, as compared to 68%, 65%, and 6% with CT. Gupta N C, Graeber G M, Bishop H A. *Comparative efficacy of positron emission tomography with fluorodeoxyglucose in evaluate of small (<1 cm), intermediate (1 to 3 cm), and large (>3 cm) lymph node lesions*. Chest 117(3):773-778, 2000. Limitations of PET scanning, however, include the cost, limited availability, inability to detect lesions under 1 cm, and lack of specificity, particularly in patients with inflammatory or granulomatous disease. Stokkel M P, Bakker P F, Heine R, Schlosser N J, Lammers J W, Van Rijk P P. *Staging of lymph nodes with FDG dual headed PET in patients with non-small cell lung cancer*. Nucl Med Communications 20(11):1001-1007, 1999; Kapuco L O, Meltzer C C, Townsend D W, Keenan R J, Luketich J D. *Fluorine-18-fluoro-deoxyglucose uptake in pneumonia*. J Nucl Med 39(7): 1267-1269, 1998.

Conventional anatomic imaging techniques such as CT scanning are also not good at predicting survival following treatment despite tumor shrinkage following therapy. In a recent study involving 56 NSCLC patients receiving treatment with concurrent cisplatin-based chemo/radiotherapy or radiotherapy alone for advanced disease, response by conventional CT imaging did not correlate with survival. MacManus M P, Hicks R J, Wada M, Hoff A, Matthews J, Wirth A, Rischin D, Ball D L. *Early F-18 FDG-PET response to radical chemoradiotherapy correlates strongly with survival in unresectable non-small cell lung cancer*. Proc ASCO 19:483a, 2000. Response by FDG-PET scans, however, did correlate strongly with survival (p=0.0006). Survival from the date of a follow-up PET scan was 84% and 84% at 1 and 2 years respectively for 24 patients who had achieved a complete response on PET, but only 43% and 31% of the 32 patients who did not (p=0.010). These results corroborate similar findings reported recently by other authors. Patz E F Jr, Connolly J, Herndon J. *Prognostic value of thoracic FDG PET imaging after treatment for non-small cell lung cancer*. Am J Roentgenology 174(3):769-774, 2000; Vansteenkiste J F, Stroobants S G, Dupont P J, DeLeyn P R, Verbeken E K, Deneffe G J, Mortelmans L A, Demedts M G. *Prognostic importance of the standardized uptake value on (18)F-fluoro-2-deoxy-glucose positron emission tomography scan in non-small cell lung cancer: An analysis of 125 cases*. J Clin Oncol 17(10):3201-3206, 1999; Ahuja V, Coleman R E, Herndon J, Patz E F Jr. *The prognostic significance of fluorodexoyglucose positron emission tomography imaging for patients with non-small cell lung carcinoma*. Cancer 83(5):918-924, 1998.

Therefore, a readily available radiopharmaceutical that could accurately identify and potentially treat early metastatic disease in the patients with NSCLC would have an important impact on patient care, in terms of both staging and response to therapy. Although PET imaging procedures are gaining effectiveness in this area, the cost and inaccessibility severely limits its practical application. There remains a need for an accurate functional imaging technique based upon a tumor-specific function that can non-invasively screen the whole body using relatively inexpensive and widely available imaging devices.

SUMMARY OF THE INVENTION

The present invention generally provides methods and techniques for the detection and treatment of various cancers.

In one preferred embodiment, the present invention provides a method for detecting and locating Lung cancer, Adrenal cancer, Melanoma, Colon cancer, Colorectal cancer, Ovarian cancer, Prostate cancer, Liver cancer, Subcutaneous cancer, Intestinal cancer, Hepatocellular carcinoma, Retinoblastoma, Cervical cancer in subject that has or is suspected of having cancer. The method comprises the steps of:
(a) administering a phospholipid ether analog to the subject; and
(b) determining whether an organ suspected of having cancer of the subject retains a higher level of the analog than surrounding region(s) wherein a higher retention region indicates detection and location of the cancer. In this method, the phospholipid analog is selected from:

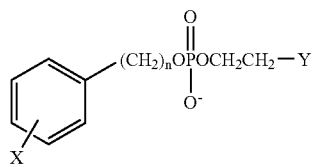

where X is selected from the group consisting of radioactive isotopes of iodine; n is an integer between 16 and 30; and Y is selected from the group comprising
$NH_2$, $N(R)_2$, and $N(R)_3$, wherein R is an alkyl or arylalkyl substituent or

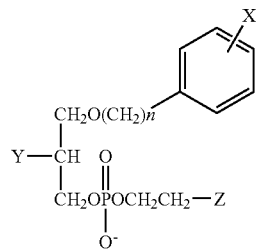

where X is a radioactive isotope of iodine; n is an integer between 16 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. In this method, X is selected from the group of radioactive isotopes of iodine consisting of $^{122}I, ^{123}I, ^{124}I, ^{125}I$, and $^{131}I$. Preferably, in this method, the phospholipid ether is 18-(p-lodophenyl)octadecyl phosphocholine, 1-O-[18(p-lodophenypoctadecyl]-1,3-propanediol-3-phosphocholine, or 1-O-[18(p-lodophenyl)octadecyl]-2-O-methyl-rac-glycero-3-phosphocholine, wherein iodine is in the form of a radioactive isotope.

In another embodiment, the present invention provides a method for the treatment of cancer in a subject. The method comprises administering to the subject an effective amount of a molecule comprising a phospholipid ether analog, as described above. In this method, the cancer is selected from a group consisting of Lung cancer, Adrenal cancer, Melanoma, Colon cancer, Colorectal cancer, Ovarian cancer, Prostate cancer, Liver cancer, Subcutaneous cancer, Intestinal cancer, Hepatocellular carcinoma, Retinoblastoma, Cervical cancer, Glioma, Breast cancer, Pancreatic cancer, Carcinosarcoma and Prostrate cancer.

The present invention also contemplates the use of a phospholipid ether analog for the production of a pharmaceutical composition for the treatment of cancer. These phospholipid analogs are selected from the group discussed above.

Yet another embodiment of the present invention provides a method of differentiating inflammation, adenoma and hyperplasia from neoplasia in a subject. The method comprises the steps of:
(a) administering a phospholipid ether analog to the subject; and
(b) determining whether an organ suspected of having inflammation, adenoma, hyperplasia or neoplasia of the subject retains a higher level of the analog than surrounding region(s). When the subject exhibits a higher retention region, it indicates detection and location of the neoplasia and when the subject exhibits a lower retention region, it indicates the presence of an organ suspected of having the adenoma, hyperplasia or inflammation.

Another embodiment of the present invention provides a method of detecting neoplasia in a tissue sample having a phospholipase D (PLD). The method comprises the step of:
(a) quantifying the PLD protein activity level or the PLD mRNA level in the tissue sample; and
(b) determining whether the tissue sample has a lower level of protein activity than surrounding tissue region(s) wherein a lower activity region indicates detection and location of the neoplasia, or
(c) determining whether the tissue sample has a lower level of mRNA than surrounding tissue region(s) wherein a lower mRNA level region indicates detection and location of the neoplasia.

In this method, the PLD protein activity or the mRNA level may be quantified by contacting the tissue sample with a PLE analog, as described above.

Yet another embodiment of the present invention provides an anti-tumor agent selected by a method of screening a tissue sample having a PLD, comprising the step of: (a) quantifying the PLD protein activity or PLD mRNA level, wherein reduced PLD protein activity or reduced mRNA level compared to the surrounding tissue region(s) is indicative of neoplasia. The PLD protein activity or the mRNA level may be quantified by contacting the tissue sample with a PLE analog, as described above.

Other objects and advantages of the present invention will be apparent from the detailed description, drawings and claims accompanying the specification

I. GENERAL DESCRIPTION OF THE INVENTION

Figure 1:
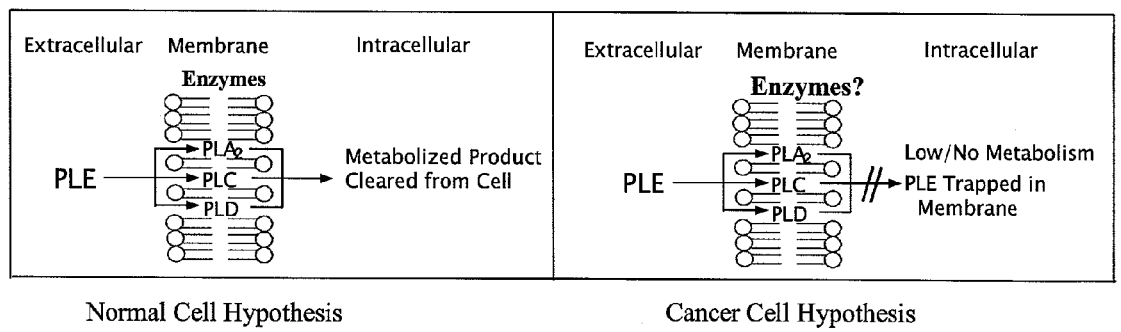
FIG. 1. PLE Tumor Cell Imaging Hypothesis.

General Description of the Invention: Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to optical isomers and analogs, structural isomers and analogs, conformational isomers and analogs, and the like. In one embodiment, this invention encompasses the use of different optical isomers of an anti-tumor compound of Formula 3A. It will be appreciated by those skilled in the art that the anti-tumor compounds useful in the present invention may contain at least one chiral center. Accordingly, the compounds used in the methods of the present invention may exist in, and be isolated in, optically-active or racemic forms. Some compounds may also exhibit polymorphism.

It is to be understood that the present invention may encompass the use of any racemic, optically-active, polymorphic, or stereoisomeric form, or mixtures thereof, which form possesses properties useful in the treatment of tumor-related conditions described and claimed herein. In one embodiment, the anti-tumor compounds may include pure (R)-isomers. In another embodiment, the anti-tumor compounds may include pure (S)-isomers. In another embodiment, the compounds may include a mixture of the (R) and the (S) isomers. In another embodiment, the compounds may include a racemic mixture comprising both (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes method utilizing derivatives of the anti-tumor compounds. The term "derivatives" includes but is not limited to ether derivatives, acid derivatives, amide derivatives, ester derivatives and the like. In addition, this invention further includes methods utilizing hydrates of the anti-tumor compounds. The term "hydrate" includes but is not limited to hemihydrate, monohydrate, dihydrate, trihydrate and the like.

This invention further includes methods of utilizing metabolites of the anti-tumor compounds. The term "metabolite" means any substance produced from another substance by metabolism or a metabolic process.

As defined herein, "contacting" means that the anti-tumor compound used in the present invention is introduced into a sample containing the receptor in a test tube, flask, tissue culture, chip, array, plate, microplate, capillary, or the like, and incubated at a temperature and time sufficient to permit binding of the anti-tumor compound to a receptor. Methods for contacting the samples with the anti-tumor compound or other specific binding components are known to those skilled in the art and may be selected depending on the type of assay protocol to be run. Incubation methods are also standard and are known to those skilled in the art.

In another embodiment, the term "contacting" means that the anti-tumor compound used in the present invention is introduced into a patient receiving treatment, and the compound is allowed to come in contact in vivo.

As used herein, the term "treating" has a commonly understood meaning of administration of a remedy to a patient who has or is suspected of having a disease or a condition. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-tumor phospholipid ether compound. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-tumor substance using a phospholipid ether compound or (2) is susceptible to a disorder that is preventable by administering the anti-tumor compound using a phospholipid ether compound As used herein, "pharmaceutical composition" means therapeutically effective amounts of the anti-tumor compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of disease (e.g., pancreatic cancer, breast cancer); and (b) the reversal or stabilization of such disease. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween (Polysorbate) 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, tansdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 15-138 (1984). Other controlled release systems are discussed in the review by Langer (Science 249:1527-1533 (1990).

The pharmaceutical preparation can comprise the anti-tumor compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-tumor compound can be administered to a patient by, for example, subcutaneous implantation of a pellet. In a further embodiment, a pellet provides for controlled release of anti-tumor compound over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

The pharmaceutical preparations administerable by the invention can be prepared by known dissolving, mixing, granulating, or tablet-forming processes. For oral administration, the anti-tumor compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the anti-tumor compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-tumor compounds or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

For use in medicine, the salts of the anti-tumor compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Generally, NM404 is a promising new tumor-selective diagnostic imaging agent to monitor the treatment response of several tumor treatment modalities. Radioiodinated NM404, a second-generation phospholipid ether analog, had displayed remarkable tumor selectivity in 10/10 xenograft tumor models and more recently in another 14/14 spontaneous rodent tumor models. Due to a lack of metabolic phospholipase enzymes in the membranes of tumor cells, the prevailing hypothesis of this approach is that phospholipid ether analogs become trapped exclusively in tumor cell membranes because of their inability to become metabolized and eliminated. Thus, the differential clearance rates of phospholipid ethers from normal cells versus viable tumor cells form the basis of this concept. Results obtained in a variety tumor models indicate that NM404 is sequestered and selectively retained by viable tumor cells and localizes in both primary and metastatic lesions regardless of anatomic location including those found in lymph nodes. Unlike FDG, this agent does not localize in infectious sites. Other advantages of NM404 over FDG include the following: NM404 is selective for and retained indefinitely by malignant tumor cells whereas FDG in not selective for tumor cells and goes to infectious sites and hyperplasias (Barret's Esophagus). Further, since $^{124}$I has a 4 day physical half life it can be shipped anywhere in the world whereas FDG with its 110 min half-life, may have limited distribution within 200 miles of the production site. NM404 undergoes prolonged retention (not metabolized) and therefore affords a significant therapeutic potential when mated with an appropriate radioisotope like $^{131}$I whereas FDG does not possess any therapeutic potential. NM404 can be labeled with a variety of iodine isotopes expanding it versatility (diagnosis and therapy as well as a tool for experimental animal studies) whereas FDG is limited to $^{18}$F for PET scanning or potentially $^{19}$F (stable) for magnetic resonance imaging albeit at very low sensitivity levels. Regardless of its tumor targeting ability, due to its rapid metabolism in tumor cells, it has not potential for therapy. NM404 affords the potential to not only accurately predict local tumor response to various treatment modalities, but also allows detection of distant metastatic lesions in cases of sub-therapeutic primary tumor treatment.

II. THE INVENTION

The present invention generally provides methods and techniques for the detection and treatment of various cancers.

In one preferred embodiment, the present invention provides a method for detecting and locating Lung cancer, Adrenal cancer, Melanoma, Colon cancer, Colorectal cancer, Ovarian cancer, Prostate cancer, Liver cancer, Subcutaneous cancer, Intestinal cancer, Hepatocellular carcinoma, Retinoblastoma, Cervical cancer in subject that has or is suspected of having cancer. The method comprises the steps of:
(a) administering a phospholipid ether analog to the subject; and
(b) determining whether an organ suspected of having cancer of the subject retains a higher level of the analog than surrounding region(s) wherein a higher retention region indicates detection and location of the cancer. In this method, the phospholipid analog is selected from:

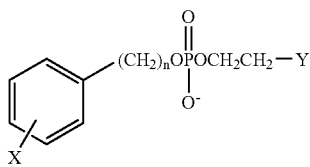

where X is selected from the group consisting of radioactive isotopes of iodine; n is an integer between 16 and 30; and Y is selected from the group comprising $NH_2$, $N(R)_2$, $N(R)_3$, wherein R is an alkyl or arylalkyl substituent or

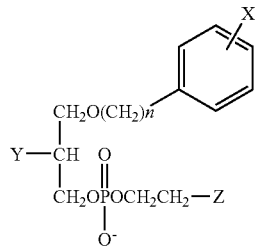

where X is a radioactive isotope of iodine; n is an integer between 16 and 30; Y is selected from the group consisting of H, OH, COOH, COOR and OR, and Z is selected from the group consisting of $NH_2$, $N(R)_2$, and $N(R)_3$, wherein R is an alkyl or aralkyl substituent. In this method, X is selected from the group of radioactive isotopes of iodine consisting of $^{122}I$, $^{123}I$, $^{124}I$, $^{125}I$, and $^{131}I$. Preferably, in this method, the phospholipid ether is 18-(p-Iodophenyl)octadecyl phosphocholine, 1-O-[18(p-Iodophenyl)octadecyl]-1,3-propanediol-3-phosphocholine, or 1-O-[18(p-Iodophenyl)octadecyl]-2-O-methyl-rac-glycero-3-phosphocholine, wherein iodine is in the form of a radioactive isotope. Various phospholipid ethers and related methodologies for the manufacture and use of the phospholipid ether compounds are described in U.S. Pat. Nos. 4,925,649; 4,965,391; 5,087,721; 5,347,030; 6,255,519 and 6,417,384 and all of which are herein incorporated by reference.

In another embodiment, the present invention provides a method for the treatment of cancer in a subject. The method comprises administering to the subject an effective amount of a molecule comprising a phospholipid ether analog, as described above. In this method, the cancer is selected from a group consisting of Lung cancer, Adrenal cancer, Melanoma, Colon cancer, Colorectal cancer, Ovarian cancer, Prostate cancer, Liver cancer, Subcutaneous cancer, Intestinal cancer, Hepatocellular carcinoma, Retinoblastoma, Cervical cancer, Glioma, Breast cancer, Pancreatic cancer, carcinosarcoma and Prostrate cancer.

The present invention also contemplates the use of a phospholipid ether analog for the production of a pharmaceutical composition for the treatment of cancer. These phospholipid analogs are selected from the group discussed above.

Yet another embodiment of the present invention provides a method of differentiating inflammation, adenoma, hyperplasia from neoplasia in a subject. The method comprises the steps of:
(a) administering a phospholipid ether analog to the subject; and
(b) determining whether an organ suspected of having inflammation, adenoma, hyperplasia or neoplasia of the subject retains a higher level of the analog than surrounding region(s). When the subject exhibits a higher retention region, it indicates detection and location of the neoplasia and when the subject exhibits a lower retention region, it indicates the presence of an organ suspected of having the adenoma, hyperplasia or inflammation.

Another embodiment of the present invention provides a method of detecting neoplasia in a tissue sample having a phospholipase D (PLD). The method comprises the step of:
(a) quantifying the PLD protein activity level or the PLD mRNA level in the tissue sample; and
(b) determining whether the tissue sample has a lower level of protein activity than surrounding tissue region(s) wherein a lower activity region indicates detection and location of the neoplasia, or
(c) determining whether the tissue sample has a lower level of mRNA than surrounding tissue region(s) wherein a lower mRNA level region indicates detection and location of the neoplasia.

In this method, the PLD protein activity or the mRNA level may be quantified by contacting the tissue sample with a PLE analog, as described above.

Yet another embodiment of the present invention provides an anti-tumor agent selected by a method of screening a tissue sample having a PLD, comprising the step of: (a) quantifying the PLD protein activity or PLD mRNA level, wherein reduced PLD protein activity or reduced mRNA level compared to the surrounding tissue region(s) is indicative of neoplasia. The PLD protein activity or the mRNA level may be quantified by contacting the tissue sample with a PLE analog, as described above.

The following sections discuss the use and methods related to only certain phospholipid ether compounds, however, such uses are exemplary and should not be deemed to narrow the scope of the present invention.

For example, NM404 a phospholipid ether has demonstrated marked specificity for neoplastic tissue but not in preneoplastic tissue in many experimental tumor models. The high tumor to background avidity and tumor selectivity of NM404 suggests it may be potentially superior to $^{18}F$-FDG PET scanning for intra-treatment tumor imaging. The precise mechanism of tumor specificity of NM404 is under investigation, and currently is not as well described as the glucose utilization mechanism for $^{18}F$-FDG uptake. It is not well established whether NM404 uptake in neoplastic tissue depends on the viability of that tissue, or if this uptake phenomenon is related to some membrane or matrix component that is independent of tissue viability. If this uptake and specificity are linked to tumor viability, it would follow that NM404 uptake in tumors recently sterilized by radiation would be non existent or poor, whereas tumors resistant to radiation would show continued uptake. Recently, Inventors demonstrated NM404 uptake and killing in both radio sensitive and radio resistant squamous cancer cells (SCC1 and 6) in nude mice. Such an assay would be invaluable in managing patients treated with radiation therapy since patients manifesting no post-treatment NM404 localization would indicate cure, whereas those with resistant tumors (continued uptake of NM404) could be offered other non-radiation options (surgery, chemotherapy, etc).

One approach to the development of sensitive, more available imaging exams is to design carrier molecules which are capable of selectively delivering a radiopharmaceutical probe to the desired target tissue. The inventors approach has been to capitalize on unique biochemical or pharmacological properties of molecules displaying a high degree of tissue or tumor selectivity.

Snyder and coworkers[16,17] observed that a variety of animal and human tumor cells contain much higher concentrations of naturally occurring ether lipids in the cell membranes than normal tissue. He proposed that the accumulation of ether lipids in tumors was a result of a lower capacity of tumor cells to metabolize these lipids due to a lack of key metabolic enzymes. The inventors have capitalized on this observation by synthesizing a number of radioiodinated phospholipid ether (PLE) analogs as potential tumor-selective imaging agents. Several of these PLE analogs have exhibited a striking and apparently universal ability to localize in and be selectively retained by a wide variety of spontaneous and transplanted rat, murine, and human tumor models (24/24).

The inventors prevailing hypothesis (FIG. 1) is that phospholipid ethers become trapped in viable tumor cell membranes because of their inability to become metabolized and eliminated. Extraction of tumors following administration of radioiodinated phospholipid ethers showed the presence of only the intact agent, whereas analysis of the urine and feces revealed only metabolites. Thus, it is the differential clearance rates of phospholipid ethers from normal cells versus tumor cells that form the basis of this concept. Preliminary results obtained in over 24 xenograft and spontaneous tumor models have universally shown NM404 to undergo selective uptake and prolonged retention in tumors. Because the agent is metabolized to some extent in the liver, the inventors avoided earlier compound evaluation in liver tumor models due to high liver background radioactivity levels. Further, because NM404 affords lower liver background levels than its predecessors, the inventors expanded evaluation into liver tumors in light of the fact that imaging patients with HCC has been problematic. Many patients have underlying cirrhosis and therefore it is difficult to distinguish regenerating nodules from HCC on cross sectional imaging. Moreover, preliminary studies evaluating PET scanning with FDG have shown only 20-50% sensitivity in detecting the disease. Verhoef C, Valkema R. et al., Liver (2002) 22:51-56. Further, PET-FDG is not useful in diagnostic screening in brain. Similarly FDG has not useful in evaluating disease in liver due to high natural uptake by hepatocytes.

Following examples depict preferred embodiments of the present invention and are for illustrative purposes only. These examples should not be deemed to narrow the scope of the present invention.

III. EXAMPLES

A. Example I

Synthesis, Radiolabeling, and Formulation of NM404

The inventors' synthetic approach was based on the copper-catalyzed cross-coupling reaction of Grignard reagents with alkyl tosylates or halides for the alkyl chain elongation (see the scheme below). The synthesis was started from p-iodobenzyl alcohol 1 which was converted into p-iodobenzyl bromide 2 by reaction with trimethylsilyl bromide. p-Iodobenzyl bromide 2 was further coupled with Grignard reagent 3 in the presence of $Li_2CuCl_4$ as a catalyst. 12-(p-Iodophenyl)dodecanol 5 obtained after deprotection of the first coupling product 4 was converted into tosylate 6. In the next step, tosylate 6 was coupled with Grignard reagent 7 containing 6 carbon atoms and this completed the chain elongation process. THP deprotection of 8 gave 18-(p-iodophenyl)octadecanol 9 which was converted into 10 (NM-404) by two-step procedure as shown in the scheme.

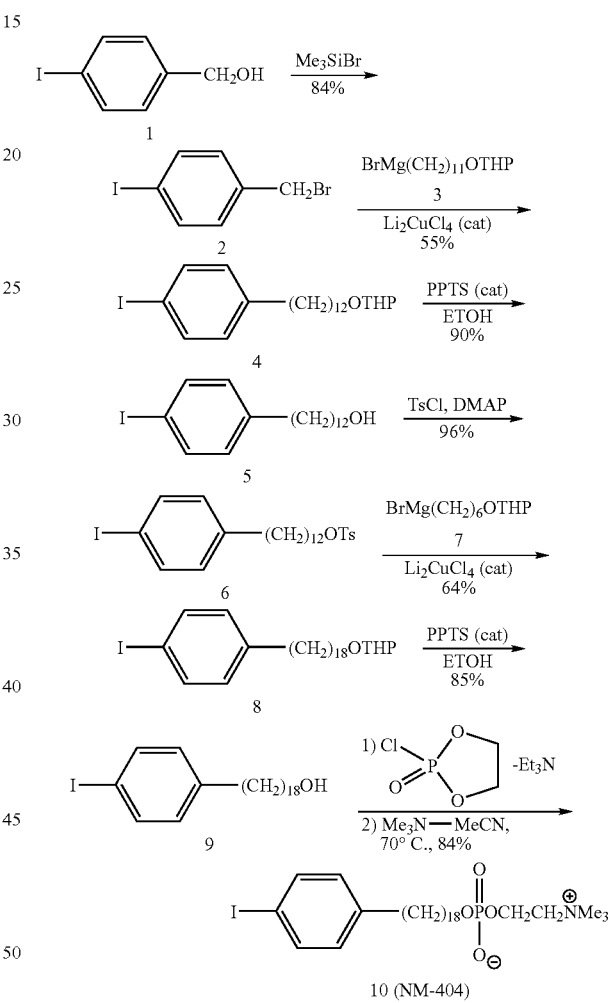

Further, rapid high yield synthesis process for labeling NM404 with any isotope if iodine, including [124]I, $^{125}$I and $^{131}$I was carried out by the following process:

First, an aluminum heating block apparatus was preheated to 145° C. and a condenser was prepared using a 5 ml disposable syringe barrel fitted with a bent 1.5 inch 18 ga disposable needle and a rubber septum at the top.

Second, the HPLC system was initiated and the reservoir was filled with filtered degassed solvent (hexane/isopropanol/water (40:52:8). The system was equilibrated followed by a systematic check-up of the ancillary systems such as the pump, detectors, chart recorders and computer integrators.

Third, a 3-mi disposable syringe charcoal trap as prepared by using a glass wool plug in bottom, filling the syringe with 2.5 mL with granulated charcoal, adding another glass wool plug and inserting a septum on top. A short tubing adaptor needle was placed on the syringe and an 18-ga needle was inserted through the septum on the top. The charcoal trap was connected to the top-of the condenser and vented to the atmosphere through a sodium thiosulfate trap.

Fourth, 5 mg of ammonium sulfate was added in 20 μl of deionized water in 2 ml borosilicate glass v-vial followed by 20 μg of unlabeled NM404 in 20-μl of absolute ethanol to the vial. The vial was gently swirled or flicked to ensure mixing and 6 borosilicate glass beads (3 mm) were also added to the vial. The vial was then sealed with a Teflon-coated butyl rubber septum and an aluminum crimp cap. The septum was punctured with an 18-ga needle and the desired amount of aqueous sodium iodide-131 (in 0.1 N NaOH, typically 5 mCi in 15 μl) was added via a Hamilton microsyringe through the septum. The vial was again gently swirled or flicked to ensure mixing. The vial was assayed in a dose calibrator.

Fifth, the charcoal trap syringe was inserted into the reaction vial and the reaction vial was lowered into the heating block well (filled half way with sand). The reaction vial was heated at 145° C. for 40 min during which most of the solvent distilled off and condensed in the condenser. A stream of air (4×25 ml) was slowly inserted through the reaction vial with a 25-ml syringe. The temperature of the reaction vile was increased to 155° C. and heating was continued for an additional 30 minutes. The reaction vial was removed from the block heater and the condenser/trap assembly was disconnected and discarded and vial was allowed to cool to room temperature.

Sixth, 0.5 ml of absolute ethanol was added into the reaction vial. The vial was gently swirled and assayed in the dose calibrator.

Seventh, a radio-TLC analysis of the crude labeled product mixture was conducted on silica gel (chloroform/methanol/water (65/35/4).

Eighth, Amberlite IRA 400-OH resin column was prepared by presoaking 1.0 g of resin in 5 ml of abs. ethanol for 30 minutes. Ethanol was decanted and the resin was rinsed with two additional 5 ml portions of ethanol. The wet resin was added into a 3 ml disposable syringe barrel with a glass wool plug at the bottom and fitted with an Acrodisc filter and a 1-way stopcock. The ethanolic solution of the crude radioiodinated product was gradually eluted through the resin column into a 5 ml vial.

Ninth, a septum was inserted and the solvent was blown off with a stream of nitrogen. A charcoal syringe was attached on the outlet of the vial prior to initiating nitrogen flow. Once dry, 50 μl of ethanol was used to dilute and transfer contents to a 300 μl v-vial. The source vial was rinsed with a second 50 μl ethanol wash and transferred to the v-vial.

Tenth, HPLC pump was stabilized and a solvent flow of 1.0 ml/min was established. The reaction mixture was purified by HPLC on a Perkin-Elmer cartridge silica column (4.3×33 mm, 3 μm silica) eluted with hexane/isopropanol/water (40:52:8) at 1.0 ml/min. Peak detection was performed by UV at 230 and 254 nm and by radioactivity. Once the appropriate peak was collected in a sterile vial, a small sample for radio-TLC analysis was removed and the remaining solvent was evaporated with a stream of nitrogen to give the desired compound as a dry residue. Specific activity was calculated as necessary.

Eleventh, Polysorbate 20 was added at a ratio of 0.1 μl/1.0 μg of NM-404 to the flask from a stock solution of 5% Polysorbate 20 in absolute ethanol. Polysorbate 20 is the pharmaceutical grade of Tween 20 that is now used in both human and animal studies with NM404. The solvent was removed by rotary evaporation for 10 min at <30° C. The residue was dissolved with mixing in sufficient sterile water to yield a 2% Polysorbate 20 solution. The formulated product was passed through a sterile 0.2 μm Pall-Gelman Acrodisc filter (13 mm) into a dry, sterile, multidose vial (Hollister-Stier) vented with another sterile 0.2 μm filter. 100 μl of product solution was diverted into a vial for QC analysis.

Twelfth, radioactivity was measured in the dose calibrator and quality control tests (sterility, apyrogenicity) were performed.

All unlabeled NM404 were taken from the original stock batch that recently underwent acute toxicology testing in order to minimize potential synthetic differences between studies. Radioiodination of NM404 was routinely achieved by an isotope exchange reaction in a melt of pivalic acid developed by the inventors[19] or by the new method described herein and prepared for injection according to standard methods described by the inventors.[22] This procedure was used effectively for preparing sterile material for the initial human trials with NM324, the predecessor of NM404 and has been used over 40 times to prepare $^{125}$I- and $^{131}$I-labeled NM404. Generally, following purification and accurate mass quantification by HPLC, the radiopharmaceutical was dissolved in absolute ethanol (50-500 μl) and Polysorbate 20 (0.1 μl/μg of compound). The ethanol is removed under vacuum and the residue dissolved in sterile water to give a final solution containing no more than 2-3% Polysorbate 20. Sterilization was achieved by filtration through a sterile 0.2 μm filter unit. Final radiochemical purity must exceed 97% before using in animals. Quantification and calculation of final specific activity were achieved by HPLC analysis using known mass standards, and quantification of radioactivity ($^{125}$I) was accomplished by dilution and counting in a PE Wallac gamma-counter in order to avoid attenuation concerns. Quantification of higher energy isotopes including $^{131}$I were done with a dose calibrator with built in settings for these isotopes. Specific activities of 1 mCi per 100 μg of radioiodinated NM404 were typically achieved. Injection volumes were typically around 100 μl per mouse. Tissue distribution data were expressed as a percent injected dose (+SEM) per gram of tissue and also as percent injected dose per organ when whole organs were weighed according to published procedures established by the inventors.[22] At each time point, tumor-to-tissue-ratios were calculated on a percent injected dose per gram of tissue basis.

General tissue distribution (TD) analysis: Biodistribution studies were performed in female mice according to the standard procedure developed by the inventors.[27] Radioiodinated NM404 (5 μCi in 100 μl) was administered via tail vein injection. At the predetermined time points animals (3/time point) were euthanized by exsanguination while under pentobarbital anesthesia. A total of 16 tissues including blood, plasma, adrenal glands, bladder, bone marrow, fat, heart, kidney, liver, lung, muscle, spleen, ovaries, skin, thyroid, and tumor were excised, rinsed, and dissected free of extraneous tissue. Large organs were minced and duplicate tissue samples will be weighed and placed in plastic tubes for isotope counting. Injection site and residual carcass radioactivity were also determined in a well counter. These standard procedures have been utilized for many years in the inventor's laboratory under appropriate animal care and radiation safety approval. Tissue distribution tables were generated by a computer program which produces decay-corrected tissue radioactivity concentration data on a percent injected dose/g, % kg dose, and percent injected dose/organ +SEM basis. At each time point, tumor to tissue ratios were calculated based on a percent injected dose per gram of tissue basis. A control TD study (3 mice/time point, 15 total mice) were performed on tumor bearing mice at 4, 7, 14, 21, and 28 days most NM404 injection in order to establish comparative TD tables for all of the therapeutic regimens.

General imaging protocols: Animals received [125]I-NM404 (10 µCi) via tail vein injection and at predetermined timepoints thereafter were anesthetized (sodium pentobarbital anesthesia, 0.06 mg/g bw) and underwent radionuclide scanning using a Bioscan AR2000 radio-TLC scanner modified for mouse imaging (1 mm high resolution collimator/1 min acquisition time per lane/1 mm lane increments). Data were quantitated and presented using Winscan 2D software from Bioscan. Once excised, control and treated tumors were also scanned ex vivo on the Bioscan unit in order to allow for more accurate ROI analysis by eliminating whole body radionuclide attenuation. Animals (sodium pentobarbital anesthesia, 0.06 mg/g bw) underwent microCT scanning (Imtek Micro-CAT I, 390 step acquisition/43Kvp/410 µA) using medium resolution acquisition parameters. Data sets were reconstructed 3-dimensionally and are visualized with AMIRA 3D-visualization software. The software allows for ROI density analysis and convenient on-screen measuring.

B. Example II

Preclinical Studies with First Generation PLE Analogs

Phospholipid ethers can easily be labeled with iodine radioisotopes using an isotope exchange method developed by the inventors.[19] The iodophenyl phospholipid ether analogs are specifically designed so that the radioiodine affixed to each molecule is stable to facile in vivo deiodination. Over 20 radiolabeled PLE compounds were synthesized and tested in vitro and in vivo.[20-22] Two of these, namely NM294 and NM324 [12-(3-iodophenyl)-dodecyl-phosphocholine], initially showed the most promise in animal tumor localization studies. These prototype compounds, labeled with iodine-125, selectively localized in tumors over time in the following animal tumor models; 1) Sprague-Dawley rat bearing Walker 256 carcinosarcoma; 2) Lewis rat bearing mammary tumor; 3) Copenhagen rat bearing Dunning R3327 prostate tumors; 4) Rabbits bearing Vx2 tumors; and 5) athymic mice bearing human breast (HT39), small cell lung (NCl-69), colorectal (LS174T), ovarian (HTB77IP3), and melanoma tumors. Optimal tumor localization of these agents takes from one to several days.

Mechanistic Studies with PLE Analogs: NM324 and NM404 are similar in structure to miltefosine (hexadecylphosphocholine), an antitumor ether lipid studied most extensively in Europe. The antitumor properties of miltefosine and several other antitumor phospholipid ether analogs have been demonstrated in a wide range of tumor cell lines including prostate-, bladder-, and terato-carcinomas, murine and human leukemias, as well as lung, colon, ovarian, brain and breast cancers.[23] In contrast to many anticancer drugs, these phospholipid ether analogs do not bind directly to DNA and are not mutagenic. Although the precise antiproliferative mechanism of action has not been determined, they apparently act at several tumor cell sites. These compounds have been associated with a variety of cellular effects including transport, promotion of cytokine formation, apoptosis induction, and interference with a variety of key lipid metabolism and cell signaling enzymes most of which are located in the cellular membrane. Although a debate exists regarding the mode of uptake into cells, the majority of reports now support the idea that these ether lipids are directly absorbed into cell membranes where they accumulate. A widespread belief is that these agents act by perturbing membrane phospholipid metabolism; however, cellular distribution studies with these agents have been limited by spontaneous cellular compartmental redistribution during homogenization and subcellular fractionation procedures. In contrast to the tracer imaging doses (several pg) the inventors have employed, antitumor effects are seen only at doses generally exceeding 300-1000 mg per day.[23]

Figure 24:
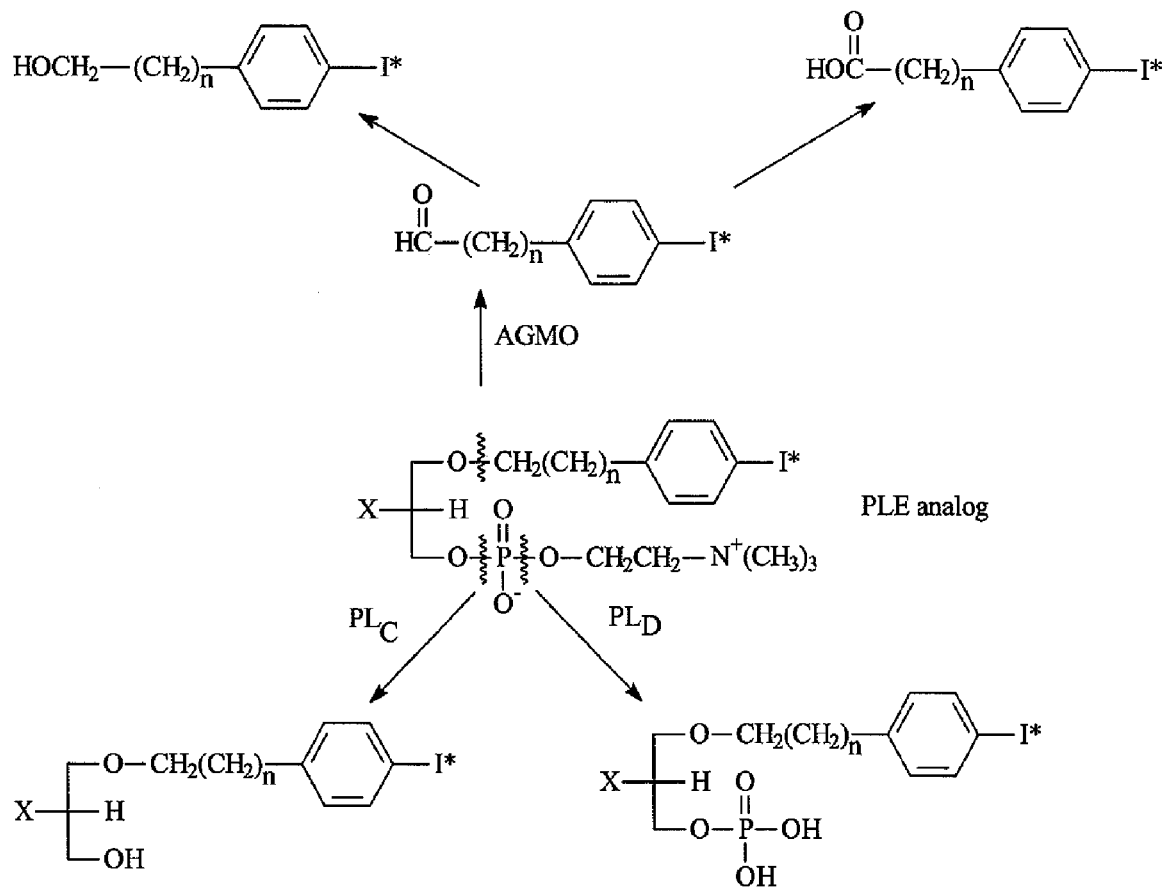
FIG. 24. Enzymatic Metabolism of PLE's.

Formal metabolism studies were conducted on several PLE analogs including NM324, the predecessor of NM404. In these studies, each agent was examined to determine their ability to serve as substrates for enzymes associated with PLE metabolism. As shown in FIG. 24, three major enzymatic pathways are involved in the metabolism of PLE. O-Alkyl glycerol monooxygenase (AGMO) is responsible for cleavage of the alkyl ether linkage at C-1 to form either the long chain fatty alcohol or subsequently, the corresponding fatty acid. Phospholipases C ($PL_C$) and D ($PL_D$), on the other hand, give rise to the glycerol or phosphatidic acid products, respectively. Using a microsomal AGMO enzyme preparation, NM324 was not a substrate for this enzyme when compared to [$^3$H]-lyso-PAF (platelet activating factor), which was extensively metabolized. In a similar fashion, NM324 was analyzed as a substrate for $PL_C$ isolated from *Bacillus cereus* and was not hydrolyzed relative to 1-palmitoyl-2-[3H]-palmitoyl-L-3-phosphatidylcholine (DPPC), which underwent significant hydrolysis.

Finally, several PLE analogs were subjected to a PLD assay. The PLD, which was isolated from cabbage, is similar to mammalian $PL_D$ in that the cabbage form affords phosphatidylethanol-type products in addition to phosphatidic acid when the enzymatic reaction is performed in the presence of ethanol. Several of the PLE analogs subjected to these assay conditions did give rise to the phosphatidylethanol adduct, indicating possible interaction with $PL_D$.

Several NM404 precursors were also subjected to in vitro metabolism studies in various cell lines including Walker tumor cells, rat muscle (H9c2), and rat hepatocytes. In these studies, the extent of metabolism was determined on the basis of radiolabeled products formed after incubation for various time periods and the results normalized to cell number or the amount of cellular protein. Subsequent lipid extraction of the incubation medium and cell suspension demonstrated little generation of PLE metabolites in the Walker tumor cells whereas a significant production of metabolites was seen in both the muscle cells and hepatocytes over the 48 h time period studied. These results correlate nicely with in vivo biodistribution studies completed on all analogs. Although several studies have been completed, the role of metabolic trapping in the uptake and retention of radiolabeled PLE analogs in tumor cells is not well defined and currently remains an active area of examination.

Figure 2:
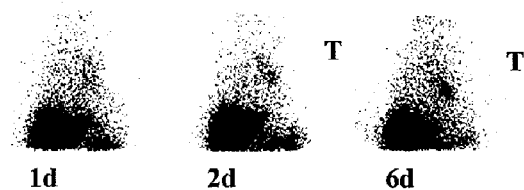
FIG. 2. Scintigraphy of the anterior chest of Patient 03 acquired at 1, 2, and 6 days after IV administration of 1 mCi $^{131}I$-NM324. Uptake is seen in the left lingular lung cancer (T) with increasing tumor-to-background ratios over time.

Clinical Evaluation of NM324: Of several promising first generation PLE analogs, NM324 was more readily synthesized and was thus selected as the lead compound for initial clinical studies. Although images obtained in 5 human lung cancer patients detected tumors, images were complicated by high liver radioactivity (FIG. 2).

Figure 3:
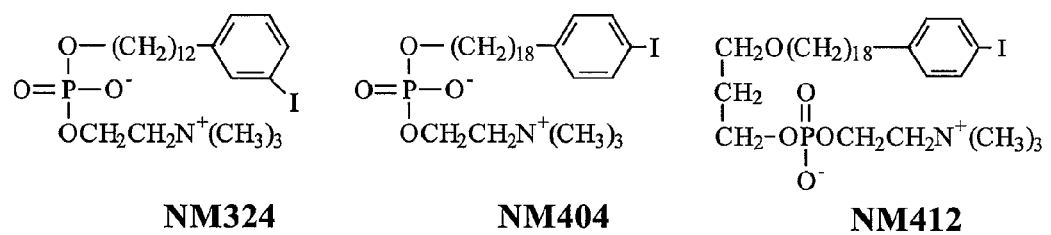
FIG. 3. Structures of PLE analogs.

Second Generation PLE Analogs: In order to decrease liver uptake and prolong the plasma phase, 9 structural analogs of NM324 were synthesized and radiolabeled with $^{125}$I for initial image analysis in Copenhagen rats bearing Dunning R3327 prostate tumors. Based upon this initial screen, NM347, NM404 [18-(4-iodophenyl)-octadecylphosphocholine] and NM412 (FIG. 3) were selected to undergo further imaging and biodistribution analysis in animal-tumor models.

Figure 4:
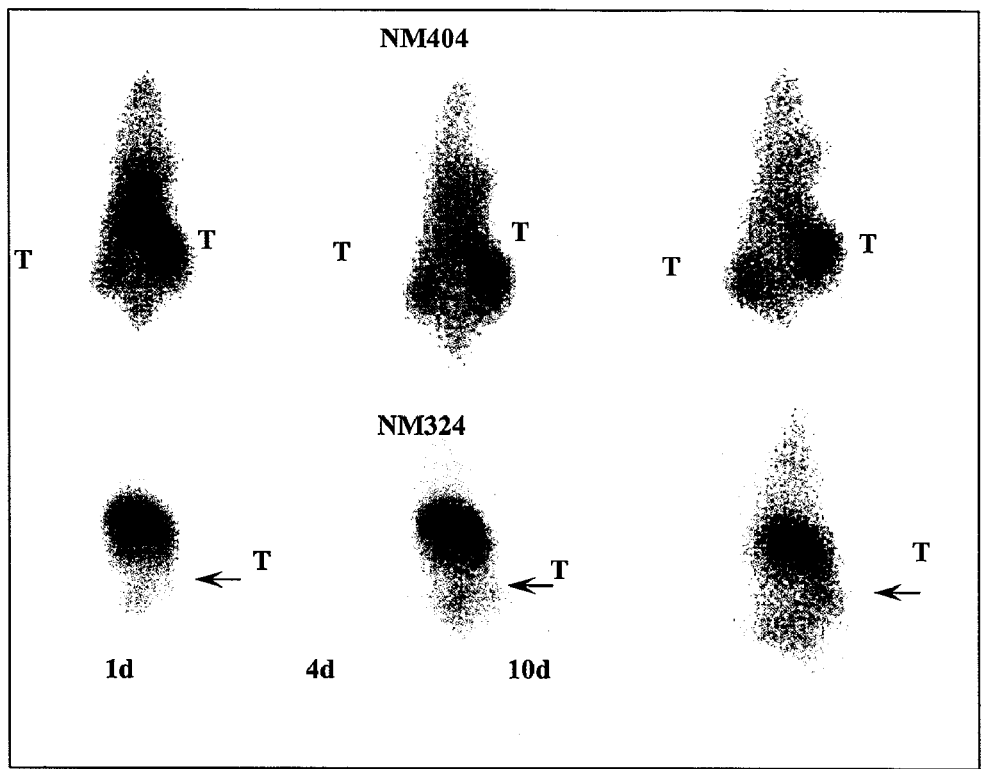
FIG. 4. Comparison of NM324 and NM404 in SCID mouse A549 lung tumor model following IV administration. Note that most of the NM324 activity is found in the gut and not in the tumor (implanted in the thigh) whereas NM404 identified one tumor in each thigh.
Figure 4A:
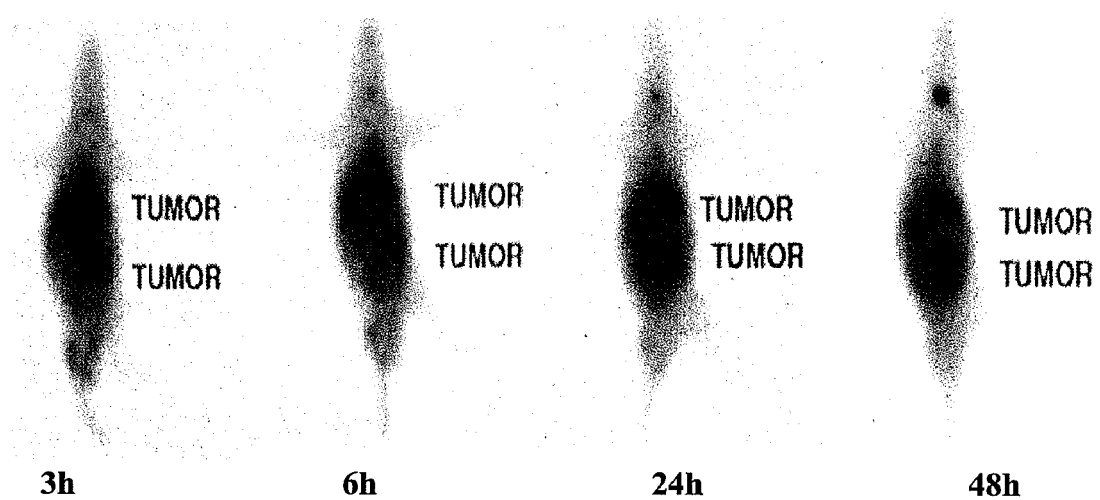
FIG. 4A. Scintigraphic NM404 images of Dunning R3327 metastatic prostate tumors in a Copenhagen rat with primary tumor site (leg) surgically removed. Two lymph node tumors were verified post mortem.

More recent imaging studies with NM404 and NM412 in animal models showed that both were superior to NM324 in visualizing a variety of tumors. Significantly, lymph node metastases were clearly delineated in a metastatic prostate tumor model following intravenous administration of either NM404 or NM412. Most importantly, the tracer was not retained by uninvolved lymph nodes.[24] (FIG. 4A). Although conducted in a prostate model, this finding is particularly relevant to breast cancer wherein lymph node involvement is such an important prognostic indicator. A preliminary pilot study conducted in SCID mice bearing human A549 NSCLC tumors were encouraging and demonstrated that NM404 overcomes the problem of high first pass clearance of NM324 by the liver. NM404 shows excellent tumor visualization, especially striking in the delayed images, with minimal liver and kidney uptake in comparison with NM324 (FIG. 4). Tissue biodistribution studies further confirmed the high levels of radioactivity residing in the tumors. Although imaging results were similar with NM404 and NM412, dosimetry data obtained in rats revealed lower kidney doses were found with NM404 relative to NM412, and thus NM404 was selected for further studies. Comparative biodistribution data for NM324 and NM404 in SCID mice with prostate and A549 lung cancer tumor models have revealed high tumor to normal tissue ratios and tumor uptake exceeding 25% of the injected dose with NM404.

Animal imaging studies performed in mouse models aimed at determining the uptake characteristics in a wide variety of tumor models are summarized in Table 1. Preliminary results in B6 Apc$^{Min}$/+ mice indicate that NM404 is not taken up by adenomatous polyps but is taken up and retained by mammary adenocarcinomas in this model, thus indicating a possible specificity for malignant tumor cells. These studies are aimed at determining the potential of NM404 to noninvasively characterize tumors. NM404 has displayed significant tumor uptake and retention in every adenocarcinoma model studied.

TABLE 1

Summary of tumor models examined with NM404

| Tumor Model | Species | Category | Uptake |
|---|---|---|---|
| Human Tumor Xenografts | | | |
| Prostate PC-3 | SCID Mouse | Adenocarcinoma | Yes |
| Lung A-549 (NSCLC) | SCID Mouse | Adenocarcinoma | Yes |
| Lung NCI H-69 (Oat | Nude Mouse | Adenocarcinoma | Yes |
| Adrenal H-295 | SCID Mouse | Adenocarcinoma | Yes |
| Adrenal RL-251 | SCID Mouse | Adenocarcinoma | Yes |
| Melanoma A-375 | Nude Mouse | Adenocarcinoma | Yes |
| Colon LS-18O | Nude Mouse | Adenocarcinoma | Yes |
| Ovarian HTB-77 | Nude Mouse | Adenocarcinoma | Yes |
| Animal Tumor Xenografts | | | |
| Mammary MCF-7 | Rat | Adenocarcinoma | Yes |
| Prostate MatLyLu | Rat | Adenocarcinoma | Yes |
| Walker-256 | Rat | Carcinosarcoma | Yes |
| Recent Rodent Models | | | |
| TRAMP prostate | Spontaneous mouse | Adenocarcinoma | Yes |
| Liver CT-26 | Mouse xenograft | Colorectal adenocarcinoma | Yes |
| Subcutaneous CT-26 | Mouse xenograft | Colorectal adenocarcinoma | Yes |
| Min Mouse Intestinal | Endogenous Mouse | Adenocarcinoma | Yes |
| Melanoma | Mouse xenograft | Adenocarcinoma | Yes |
| SCC1 and 6 | Nude mouse | Squamous cell carcinoma | Yes |
| Mammary SCC and AC | Apc$^{Min/+}$ mouse | SCC and Adenocarcinoma | Yes |
| Hepatocellular Carcinoma | Spontaneous mouse | Adenocarcinoma | Yes |
| Retinoblastoma | Spontaneous mouse | Blastoma | Yes |
| Cervical Adenocarcinoma | Spontaneous mouse | Adenocarcinoma | Yes |
| Pancreatic c-myc and kras | Spontaneous mouse | Adenocarcinoma | Yes |
| Glioma L9 | Rat Xenograft | Glioma | Yes |
| Intestinal polyp | Apc$^{Min/+}$ mouse | Adenoma | No[1] |
| Mammary Hyperplasia | Apc$^{Min/+}$ mouse | Alveolar Hyperplasia | No[1] |

[2]Tumor uptake was <<1% injected dose/gram

Figure 5:
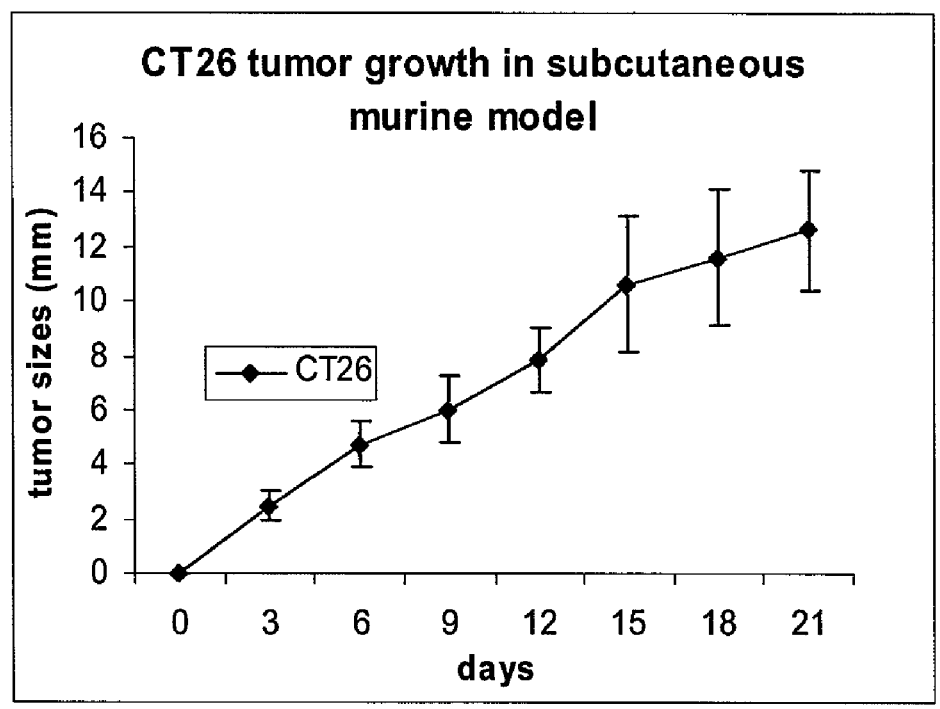

Relevance of CT26 Murine Tumor Model: Inventors explored NM-404 as a predictor of tumor response in a murine (BALB/c mice) model with subcutaneous CT26 cell inoculation into the flanks of the mice. The CT26 cell line is a poorly differentiated murine adenocarcinoma that was induced by rectal injection of N-nitroso-N-methylurethane in BALB/c mice. The cell line is simple to grow in vitro and results in a predictable growth pattern when injected in the vasculature (tail vein injection, metastatic model), or into the skin (FIG. 5) or liver.[25,26] Because the cell line is derived from a colorectal cancer, this murine model is highly clinically relevant for these studies.

Figure 6:
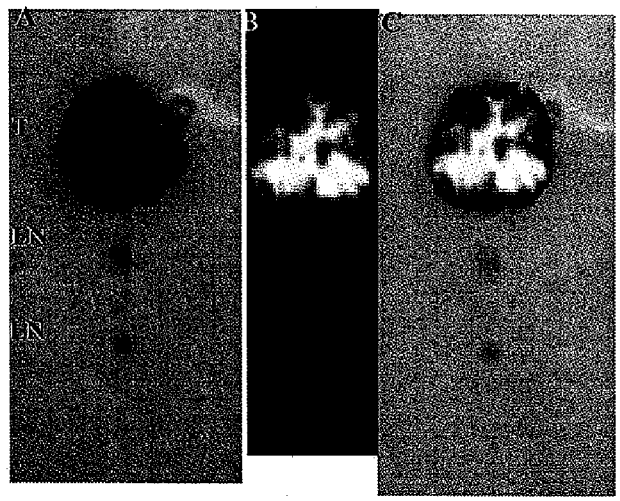
FIG. 6. Digital Photo (A) of excised CT-26 tumor (T) and left and right lymph nodes (LN). Bioscan image (B) and fused photo/Bioscan image (C) showing correlation of radioactivity in tumor.
Figure 7:
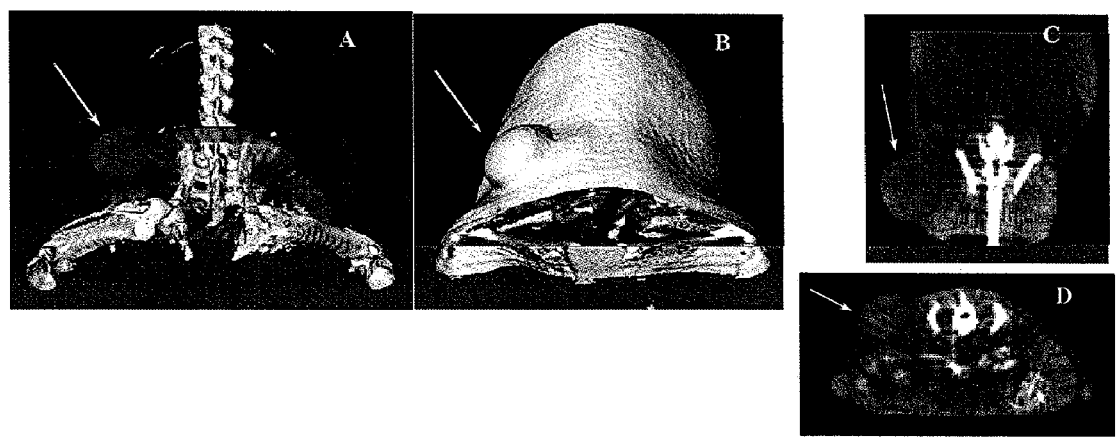
FIG. 7. MicroCT images of live mouse of FIG. 6 showing size and location of CT-26 tumor (arrows). 3D-surface rendered and planer slice images (A, B) as well as coronal (C) and axial (D) slices (40 μm thickness).

Preliminary Imaging Results with NM404 in CT26 Tumors: In a preliminary experiment to show that NM404 localizes in subcutaneous CT26 xenografts, two animals were injected (IV tail vein) with $^{125}$I-NM404 (10 µCi) and subsequently imaged on a modified Bioscan AR2000 radio TLC scanner (equipped with high resolution 1 mm collimator and 2-D acquisition and analysis software) at 1, 4, and 7 days post injection. On day 7, the animal was euthanized and the tumor removed, photographed, and scanned ex vivo on the Bioscan (FIG. 6). Ex vivo scanning is standard protocol in the inventor's lab due to the severe tissue attenuation effects associated with iodine-125. Each animal also underwent microCT scanning (FIG. 7) on day 7 prior to euthanasia and dissection of the tumor. Focal hot spots correlated visually with all tumors on ex vivo Bioscan images (FIG. 6). Although lymph nodes are visible, no radioactivity was associated with them indicating a lack of tumor cell infiltration. The main tumor in FIGS. 6 and 7 was histologically categorized as an adenocarcinoma. The inventors have scanned a wide variety of subcutaneous tumors via microCT and all are very easily detectable down to less than 300 microns in diameter.

Figure 8:
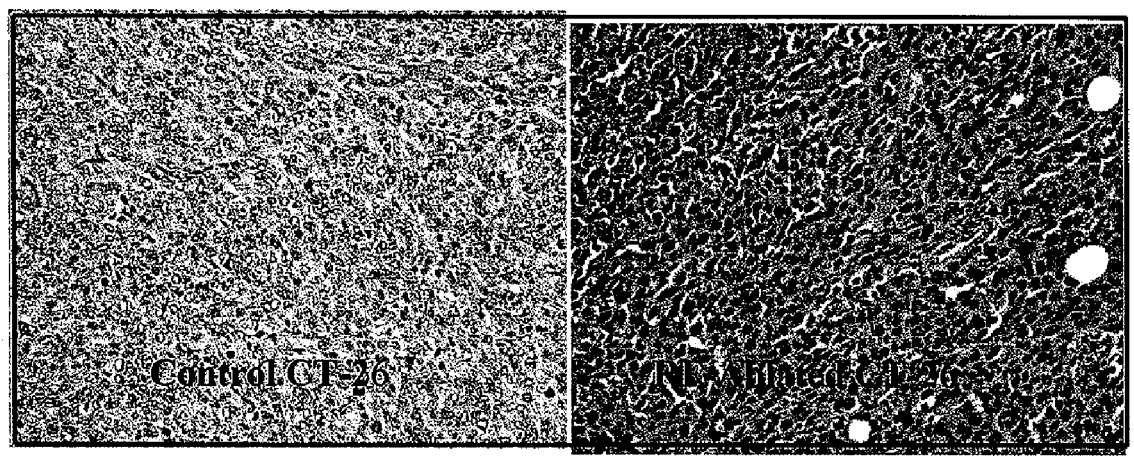
FIG. 8. Histologic section (H&E) of normal (left) and RF-ablated (right) CT-26 tumor. Ablated section has lost membrane integrity and appears pyknotic.

Initial RF ablation of a subcutaneous mouse CT26 tumor was successful and resulted in severe cellular damage (FIG. 8) as indicated by the loss of cellular membranes in the treated H&E-stained section.

C. Example III

Non-Small Cell Lung Cancer

Imaging and biodistribution studies were performed in SCID (severe combined immune deficiency mutation) mice bearing the human NSCLC adenocarcinoma A549 cell line (adenocarcinoma has become the most frequent human lung cancer histologic type). Preliminary pilot results in five animals were encouraging and demonstrated that the new agent NM404 overcomes a limitation of the NM-324 compound. While there is reasonably good tumor uptake with NM324, imaging is compromised by a high first pass clearance by the liver. However, NM404 shows excellent tumor visualization, especially striking in the delayed images, with minimal liver and kidney uptake. Moreover, tissue biodistribution studies further confirmed the high levels of radioactivity residing in the tumors. A comparison of NM324 and NM404 images in a SCID mouse-human NSCLC model are shown in FIG. 4. Note the relative lack of liver, kidney and gut activity with NM404, coupled with excellent tumor visualization. Although imaging results were similar with NM404 and NM412, recent dosimetry data obtained in rats revealed lower kidney doses were found with NM404 relative to NM412, and thus NM404 has been selected for further studies.

Extensive biodistribution data for the prototype agent $^{125}$I-NM324 in several tumor models have previously been compiled. Counsell R E, Schwendner S W, Meyer K L, Haradahira T, Gross M D. *Tumor visualization with a radioiodinated phospholipid ether*. J Nucl Med 31(3):332-336, 1990; Plotzke K P, Fisher S J, Wahl R L, Olken N M, Skinner S, Gross MD, Counsell R E. *Selective localization of a radioiodinated phospholipid ether analog in human tumor xenografts*. J Nucl Med 34(5):787-792, 1993; Rampy M A, Brown R S, Pinchuk A N, Weichert J P, Skinner R W, Fisher S J, Wahl R L, Gross M D, Etheir S P, Counsell R E. *Biological disposition and imaging of a radioiodinated alkylphosphocholine in two rodent models of breast cancer*. J Nucl Med 37(9):1540-1545, 1996. Tumor-to-blood ratios exceeding 8:1 were seen at delayed times post-injection. For example, in a rat mammary tumor model, tumor-to-normal tissue ratios reached a maximum at 96 hours with a tumor-to-blood ratio of 8.6 and tumor-to-muscle ratio of 20:1. Rampy M A, Brown R S, Pinchuk A N, Weichert J P, Skinner R W, Fisher S J, Wahl R L, Gross M D, Etheir S P, Counsell R E. *Biological disposition and imaging of a radioiodinated alkylphosphocholine in two rodent models of breast cancer*. J Nucl Med 37(9): 1540-1545, 1996. Moreover, the biodistribution of PLE-associated radioactivity is heterogeneous in tumor, as demonstrated by microautoradiography studies showing that the PLE radioactivity resides exclusively in viable tumor cells located toward the outer regions rather than the central necrotic regions. Rampy M A, Brown R S, Pinchuk A N, Weichert J P, Skinner R W, Fisher S J, Wahl R L, Gross M D, Etheir S P, Counsell RE. *Biological disposition and imaging of a radioiodinated alkylphosphocholine in two rodent models of breast cancer*. J Nucl Med 37(9):1540-1545, 1996.

Comparative biodistribution data for NM324 and NM404 in SCID mice thus far have only been performed in prostate and A549 lung cancer tumor models. These studies have revealed high tumor to normal tissue ratios and tumor uptake exceeding 25% of the injected dose with NM404, thus supporting our desire to study the biodistribution of PLE analogs in more spontaneous tumor models and humans.

Figure 23:
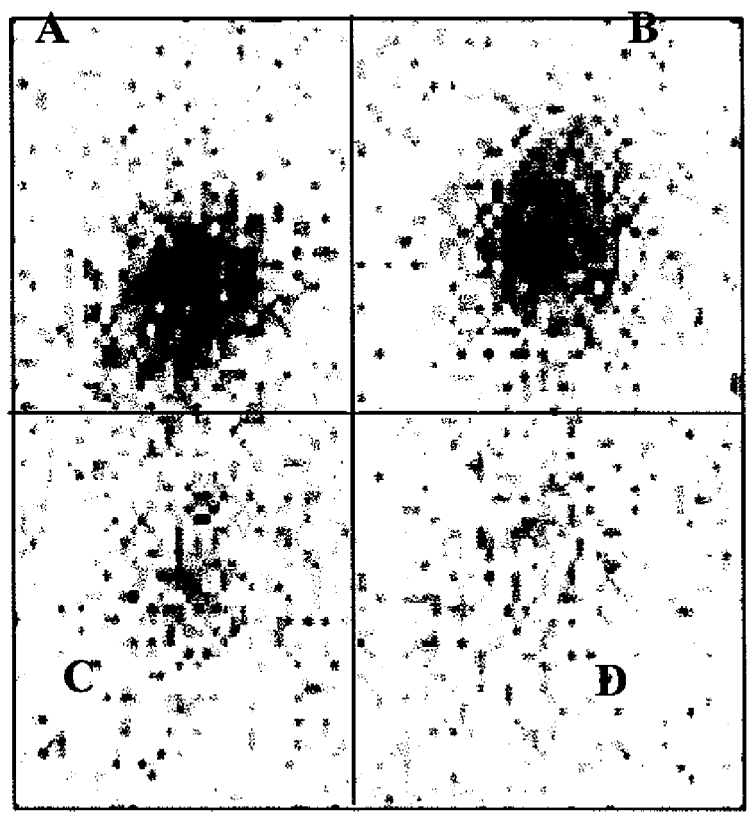
FIG. 23. Comparison of $^{125}$I-NM404 (A&B) and NM324 (C&D) uptake in excised SCID mouse lungs containing A549 lung CA micromets (<1 mm dia).

One additional study addressing the relative sensitivity of NM404 to NM324 was performed in a SCID mouse A549 lung cancer model. The lungs of each animal were excised 10 days after administration of equal doses of each agent and imaged ex vivo for one hour in order to enhance resolution. The low resolution and highly amplified images shown in FIG. 23 revealed the presence of a focal radioactivity in the lungs of both animals imaged with NM404 and little or no uptake in the NM324 pair. Subsequent pathologic analysis confirmed the presence of small A549 micro-metastases (less than 1 mm in diameter) in all 4 animals. The count rate in the NM404 mice was greater than 2.5 times that in the corresponding NM324 mice, again indicating a superiority of NM404 over NM324.

It is likely that because the tumor-targeting strategy appears to involve selective tumor retention over time, relatively short-lived nuclides such as $^{18}$F or even $^{99m}$Tc are not practical for labeling at the current time. However, as with the early use of monoclonal antibodies, which were labeled exclusively with radioisotopes of iodine, it may be possible in the future to label PLE analogs with alternative labels, such as iodine-124, wherein the physical half-life matches well with PLE tumor uptake and retention kinetics. In fact, the utility of $^{124}$I-labeled NM404 as a tumor selective PET agent is the subject of a pilot project for our microPET acquisition. The aim of that project is to evaluate the feasibility of labeling NM404 with iodine-124, a relatively new positron isotope with a 4-day physical half-life, and to evaluate its promise for PET imaging of tumors in small animal models. In addition to capitalizing on the resolution enhancement and 3-dimensional capabilities PET imaging affords relative to traditional gamma camera imaging, this approach would compliment the use of fluorine-18 FDG in that its uptake into tumor cells occurs via a different biochemical mechanism than glucose utilization.

As has been discussed above, the utility of currently available tracers (e.g. $^{67}$Ga and $^{18}$F-FDG) is limited by lack of specificity to distinguish neoplasm from inflammation. However, preliminary studies with PLE agents has offered promise in overcoming this clinically significant limitation wherein carrageenan-induced granulomas in rats failed to visualize above background activity and showed no tissue retention. Counsell R E, Schwendner S W, Meyer K L, Haradahira T, Gross M D. *Tumor visualization with a radioiodinated phospholipid ether*. J Nucl Med 31(3):332-336, 1990. Gallium citrate, however, utilized as a control in that study, did concentrate significantly in the granuloma. Such findings further justify extending the inventors" studies with PLE analog agents as potentially useful tumor-selective imaging agents.

Human Studies: Based upon the very promising pharmacokinetic and imaging data in animals, the inventors were encouraged to move studies of radiolabeled phospholipid ethers into the clinical arena. Unlabeled NM404 was initially assessed for its acute toxic effects on rats and rabbits in studies conducted at the Toxicology Research Center, State University of New (SUNY) at Buffalo. No toxic effects were seen at a dose level of 3.2 mg/kg (>150 times the highest anticipated human dose) in these acute dose toxicity studies. Moreover, no platelet activating properties were demonstrated at this high dose level.

Unlabeled NM324 was administered to five normal, disease-free, humans in order to gain approval of the radiolabeled agent for human administration by the Radioactive Drug Research Committee (RDRC). These subjects had no evidence of toxicity, as manifested by symptoms, clinical examination, vital signs and sequential blood chemistries.

As a pilot feasibility project, 4 lung cancer patients were studied under RDRC approval with $^{131}$I-labeled NM324 at the Ann Arbor, Michigan V A hospital. Lung tumors were clearly visualized in all three of the patients with lung cancer (two with NSCLC and one with small cell lung cancer), described in detail below. Degree of tumor uptake, at various time points, varied from 1+ (barely perceptible above background) to 3+ (intense uptake, much greater than normal structures). Note that the patients selected for these initial studies were those with known, relatively large cancers. It was not intended at this stage to study patients in whom problems of tumor staging existed.

Case Histories:

Patient 01 was a 55 year old woman with a right middle lobe lung mass eroding into the right ribs, histologically a mucin-producing adenocarcinoma of probable lung origin. Initial $^{131}$I-NM324 scintigraphic images at 6 hours showed a focus of uptake in the right lateral mid-lung. For reasons unrelated to the scintigraphic study, the patient was unable to return to the hospital beyond 6 hours for further imaging session.

Patient 02 was a 62 year old man with a large (9×7×7.5 cm), lobulated mediastinal mass extending from the aortopulmonary window and left hilum. Tissue type was a small cell undifferentiated (oat cell) carcinoma. $^{131}$I-NM324 scintigraphic images revealed a focus of uptake in the left upper lung, which increased in intensity over time relative to the normal background activity.

Patient 03, a 74 year old man with a right upper lobe NSCLC (adenocarcinoma) treated 5 months previously with radiation therapy. Disease recurred in the left lingula (2.5× 2×3 cm mass), lower thoracic spine (approx. T8) and right lobe of the liver. $^{131}$I-NM324 scintigraphy showed well defined uptake in the lung mass and thoracic spine lesion, which demonstrated increasing target to background ratios over time (FIG. 2). Uptake in the liver metastasis could not be resolved above the normal liver background.

These studies provided an early glimpse of the clinical promise of radiolabeled PLE analogs. Although $^{131}$I is a suboptimal agent for imaging purposes, uptake in all three lung tumors was clearly depicted. As expected, based upon prior animal biodistribution experiments, activity in the tumors increased over time, as clearly demonstrated in patients 02 and 03. In patient 03 tumor-to-normal tissue ratios increased from 2.74 at 2 days to 4.23 at 7 days. Patient 01 did not return for later imaging sessions beyond 6 hours. The increasing target-to-background ratios constitute strong evidence that the mechanism for tumor visualization is not one based merely upon abnormal blood flow or tumor hypervascularity. Indeed, animal studies using $^{99m}$Tc human serum albumin confirmed this.[1]

Clinical Trial Evaluating Patients With Non-Small Cell Lung Carcinoma (NSCLC) using NM404

Figure 29:
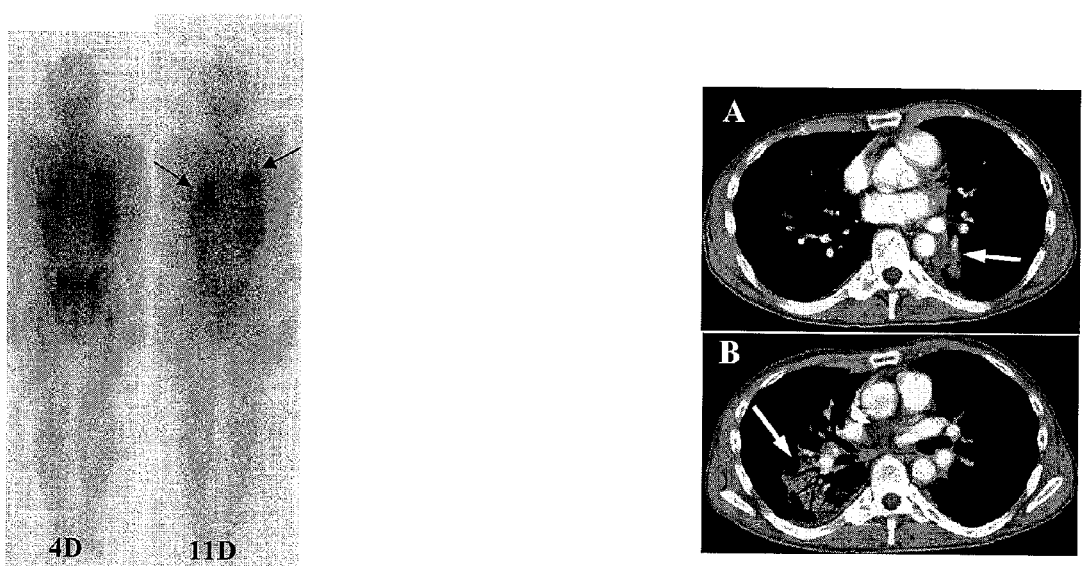
FIG. 29. Patient 1 gamma cameral images (left panel) at 4 and 11 days following $^{131}$I-NM404 injection showing intense and prolonged retention of the agent in both NSCLC tumors (arrows). Axial CT scans (right panel) showing location and size of focal 3 cm lesion in left lung (A) and large infiltrative mass in right lung (B) (arrows).
Figure 30:
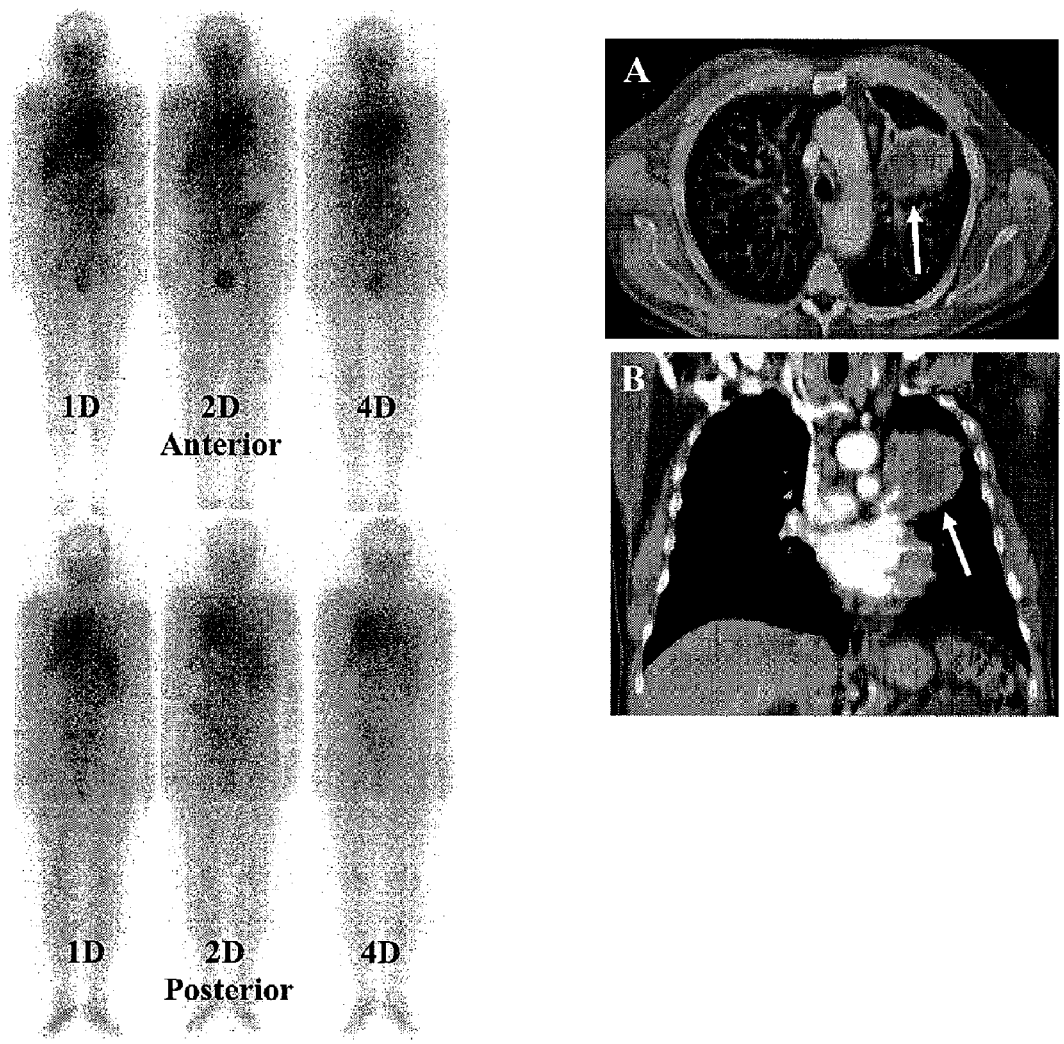
FIG. 30. Patient 2 anterior and posterior whole body planar nuclear medicine images (left panel) following iv administration of $^{131}$I-NM404. Axial (A) and coronal (B) CT scans (right panel) showing location of large 6 cm NSCLC (arrows).

Although NM404 has displayed selective and prolonged tumor retention in 25/25 xenograft and spontaneous rodent models, a physician sponsored IND recently initiated clinical evaluation of the agent in Stage 4 human non-small cell lung cancer patients in order to determine whether or not it would exhibit similar tumor uptake and retention properties in humans. To date, two patients with advanced NSCLC were imaged after an injection of <1 mCi of $^{131}$I-NM404. Blood and urine samples were collected at predetermined times, and gamma imaging performed at several time points following administration. In both patients, significant tumor uptake and retention of NM404 was demonstrated in the primary lung tumor, as seen in FIGS. 29 and 30. Relative to the high liver uptake values seen previously with its first generation predecessor, NM324, liver and abdominal activity are much lower with NM404, suggesting the feasibility of evaluating this agent in other abdominal cancers including pancreatic, colon, and prostate.

Materials and Methods: Following intravenous injection of iodine-131 labeled NM404 (1 mCi/20 µg), patients with advanced NSCLC where scanned at 3, 6, 24, 48, 96 h and at 7 and 11 days on a GE Maxxus dual Head SPECT scanner. Blood and urine samples were collected for pharmacokinetic analysis as well as clinical hematologic, renal, and hepatic bioanalysis.

Results: Initial qualitative imaging results indicate that iodine-131 labeled NM404 clearly localizes in bilateral pulmonary masses as early as 24 h after injection and is selectively retained in these tumors in excess of 11 days. Moreover, background radioactivity in the liver and lower abdominal region including urinary bladder, kidneys, and intestines was significantly less than was observed previously with its predecessor, NM324. No adverse reactions were observed in any of the patients.

Conclusions: These preliminary findings suggest that NM404 exhibits similar tumor uptake and retention properties in human NSCLC as was seen previously in rodent models.

Although based on only two patients at this point, it appears that NM404 does indeed localize in and undergo selective and prolonged tumor retention in human non-small cell lung cancer.

Patient 1: 55 year old male with bilateral 3 cm left lobe and infiltrative right lobe NSCLC and a brain metastasis and a small right adrenal mass. He has participated in numerous standard and experimental treatment regimens. Images are included in FIG. 29.

Patient 2: 70 year old male recently diagnosed with 6 cm upper lobe non small cell mass, a 5 mm liver mass, an ilial bone met and a very small brain metastasis. He had recently completed low dose carboplatin/taxol chemotherapy and palliative radiotherapy to the ilial and brain metastases the week prior to initiating the NM404 trial. Images are shown in FIG. 30.

D. Example IV

Mouse Pancreatic Adenocarcinoma Models

Inventors also studied tumor avidity of NM404, a second-generation PLE analog, in the c-myc mouse pancreatic adenocarcinoma model which is known to produce invasive tumors with mixed acinar/ductal phenotype.

Materials and Methods: Two murine strains that are endogenous for either c-myc, or k-ras, well-known oncogenes, have been developed at the University of Wisconsin.Sandgren E P, Quaife C J, et al., Proc Natl Acad Sci USA. 1991; 88:93-97; Grippo P J. Nowlin P S. Et al., Cancer Research. 63(9):2016-9, 2003.

Expression of c-myc is targeted to pancreatic acinar cells because it is linked to an elastase promoter, which is only expressed in the pancreas. These ela-1-myc endogenous mice develop acinar and ductal neoplasia, which results in death between 2 and 7 months of age. By one month of age, the pancreas appears thickened and firm. Thus mice between the ages of 1-3 months serve as excellent models for the study of pancreatic cancer. Most human pancreatic neoplasms have a ductal morphology and Dr. Sandgren's transgene targeting strategies are aimed at developing tumors that are specific for pancreatic ductal epithelium.

The c-myc model produces tumors that are invasive adenocarcinomas, with mixed acinar/ductal phenotype. The biology of the k-ras model is markedly different. The k-ras tumors have been classified as "carcinoma in situ", meaning that they have features of neoplasia, but they do not invade and generally stay small (<2 mm). Their cellular appearance is far more like the early human tumors so from a histological perspective they are a more relevant model of human disease. Further, they resemble the very early stages of the human disease. The ability to detect the "early" development of the k-ras tumors versus the large and more advanced tumors in the c-myc mice would be an exceptionally important step toward identifying early (perhaps curable) lesions in humans. The fact that k-ras mutations are the cause of over 90% of human pancreatic adenocarcinomas lends further support towards the validity of this model for the evaluation of new tumor imaging agents.

Figure 9:
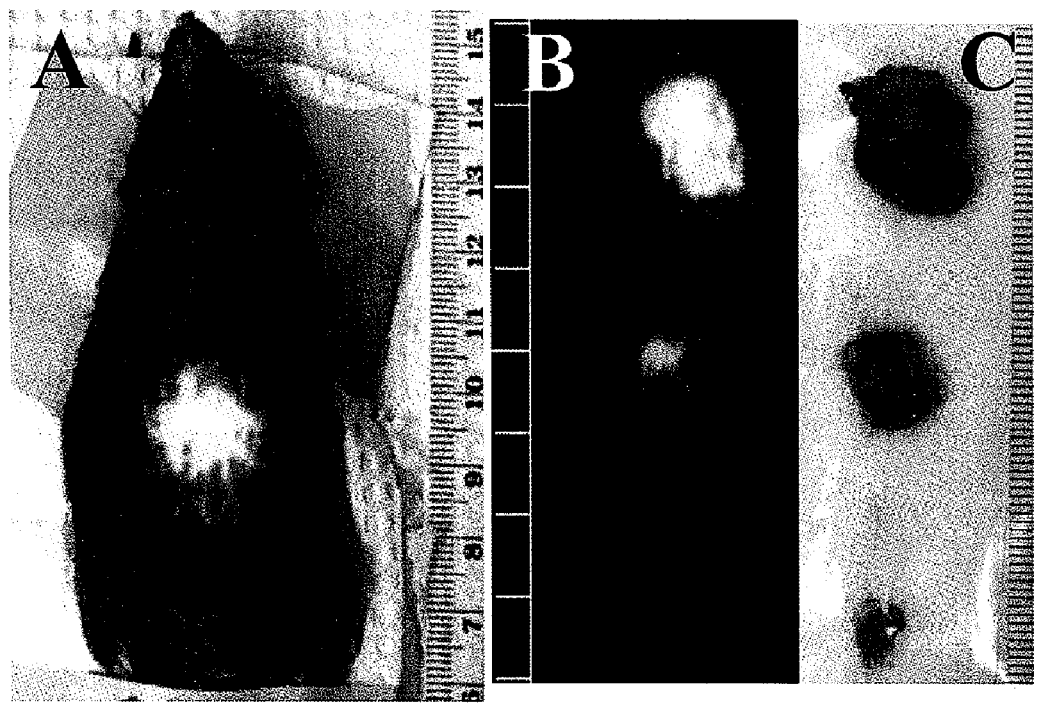
FIG. 9. Fused in vivo Bioscan/digital photo image of c-myc pancreatic tumor mouse 4 days post $^{125}$I-NM404 injection (A). Ex vivo image of excised tumors (B) for comparison with digital photo (C). Color range same as in FIG. 10.
Figure 10:
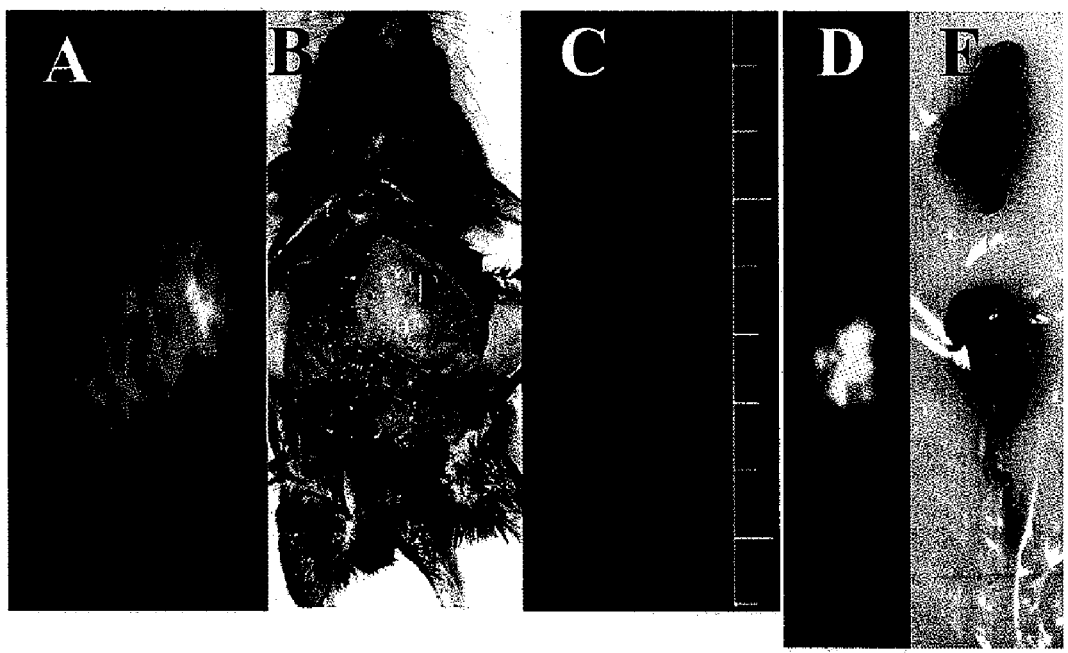
FIG. 10. Bioscan images of c-myc pancreatic tumor mouse 4-days post $^{125}$I-NM404 administration. In vivo image (A) compared with digital photo of dissected mouse (B) showing presence of a large (2 cm) pancreatic tumor (T). Three tumors were excised and the remaining carcass scanned (C). The excised tumors were scanned (D) for comparison with digital photo (E). Color scale ranges from 0 (black) to 40 (white) cpm.

Imaging Studies: In order to determine if NM404 localizes in mouse pancreatic tumors, six c-myc endogenous mice were scanned on a Bioscan AR-2000 radioTLC scanner (modified in the inventors lab for mouse imaging) from 2-21 days after tail vein injection of $^{125}$I-NM404 (15 µCi/20 g bw). On the last day, mice also underwent microCT scanning (42 kvp, 410 µA, 390 steps, MicroCAT-I, ImTek, Inc., Knoxville, Tenn.). Following in vivo imaging of anesthetized mice, the pancreatic tumors were excised and scanned ex vivo on the same scanner (equipped with high resolution 1 mm collimator and 2-D acquisition and analysis software) in order to avoid tissue attenuation associated with the low energy of iodine-125 (FIG. 9-10) At sacrifice, tissues were excised, weighed, and radioactivity quantitated in a gamma counter.

Figure 11:
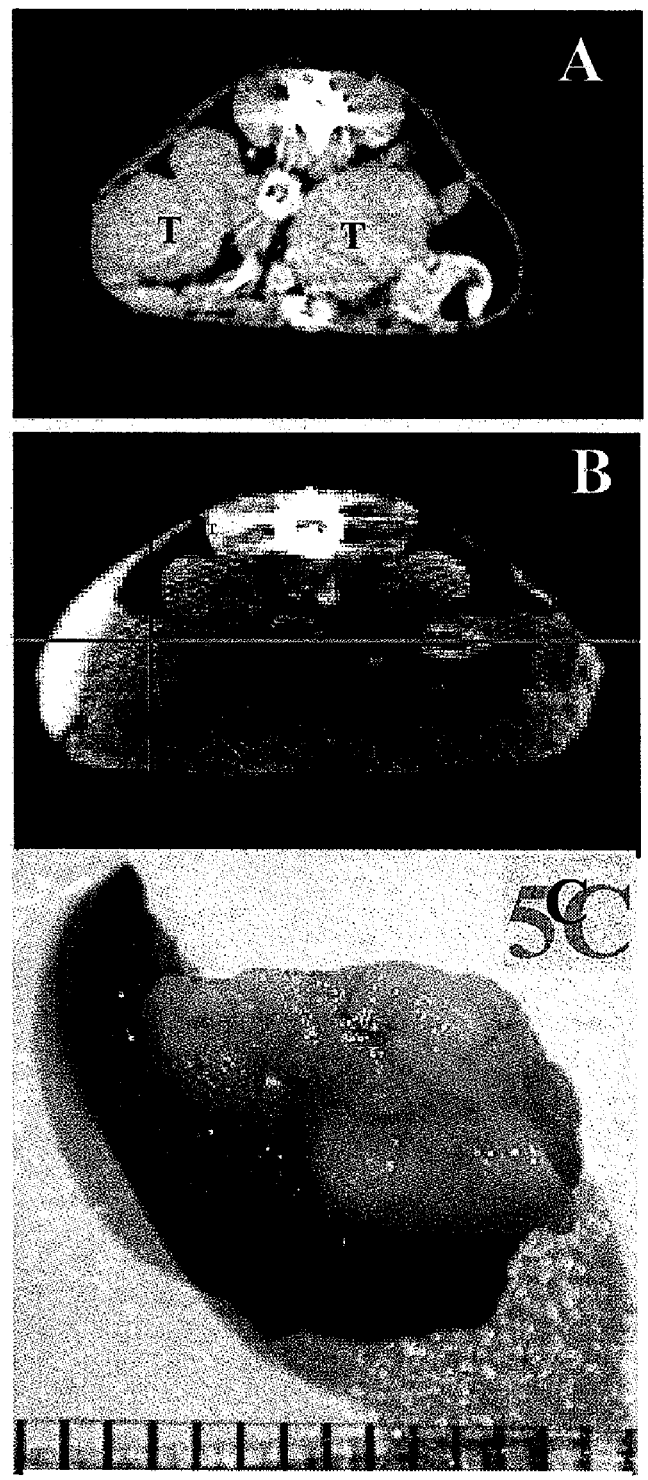
FIG. 11. MicroCT axial scans of pancreatic tumor-bearing mice. Two large tumors (T) are easily seen in the axial image in panel A. Image of a different mouse in B depicts a pancreatic tumor (arrow) located adjacent to the spleen. In mice, the pancreas is a ubiquitous tissue. A digital photo of the excised spleen and attached tumor is shown in 11 C for comparison.

Results and Discussion: Initial imaging results with NM404 in the c-myc model indicated striking uptake and prolonged retention (>21 days) in all adenocarcinomas ranging from 5-12 mm in diameter. As has been observed in previous cell culture and in vivo animal model studies, NM404 is apparently metabolized and eliminated from normal cells but becomes metabolically trapped in tumor cell membranes. Previous autoradiography experiments in other tumor models have suggested that only viable tumor cells, and not normal tissue or necrotic tissues, are capable of accumulating NM404. The inventors were also able to detect pancreatic tumors in live mice with microCT despite the ubiquitous nature of the pancreas in mice (FIG. 11) Although the number of pancreatic tumor-bearing animals is small (n=6), preliminary NM404 tumor to background data appears promising.

Conclusions: NM404 displayed selective and prolonged retention in spontaneous pancreatic adenocarcinomas examined in this study, thus further extending the tumor selectivity of this agent.

E. Example V

Rat Glioma Model

Materials and Methods: All animals were housed and handled in accordance with the University of Wisconsin Research Animal Resources Center guidelines. Rat C6 glioma cells were propagated in DMEM medium (Life Technologies, Gaithersburg, Md.) supplemented with 10% heat-inactivated FBS (BioWhittaker, Walkersville, Md.), 100 U/ml penicillin G, 100 mg/ml streptomycin, and 0.01 M HEPES (Life Technologies, Gaithersburg, Md.). Intracranial tumor implantation was performed as described previously (ref). Briefly, 1×10$^6$ C6 cells were resuspended in 5 ml 1.2% methylcellulose and injected into the frontal lobes of anesthetized female Wistar rats (Harlan, Indianapolis, Ind.). Sham-operated animals received intracranial injections of an equal volume of methylcellulose without tumor cells.

Imaging Studies: Ten days after implantation, the presence of intracranial tumors was confirmed with MRI. Briefly, anesthetized rats (6) received 2 ml of Gadodiamide (Gd, Omniscan 287 mg/ml, Nycomed, Princeton, N.J.) intraperitoneally and imaged 10 min later using a 1.5 Tesla clinical MR system (GE Signa LX) and a GE phased array extremity coil. The T1-weighted (TR=500 ms, TE=16.5 ms) multislice sequences covering the entire brain of each rat were inspected to select tumor-bearing rats with varying tumor sizes, and sham-operated rats for NM404 injections.

Figure 3A:
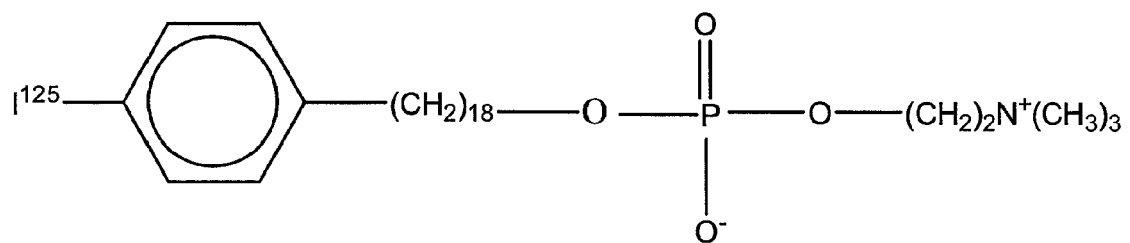
FIG. 3A. A NM404 analog.

NM404 [18-(4-iodophenyl)-octadecylphosphocholine] (FIG. 3A, 100 mg) was radioiodinated with $^{125}$I via isotope exchange with Na$^{125}$I in a melt of pivalic acid. Weichert, et al. Int J App. Rad Isotopes. 1986; 37:907-913. Following HPLC purification NM404 was dissolved in an aqueous 2% Polysorbate 20 solution prior to tail vein injection (5-20 µCi/200 g rat) into four tumor-bearing and three sham-operated rats. At 1 (n=1), 2 (n=1), and 4 (n=2) days after NM404 injection, animals were euthanized (CO2) and brains were excised and imaged on a modified Bioscan AR2000 radio-TLC scanner (1 mm increments at 2 min acquisition/lane and 1 mm high-resolution collimator). In addition, normal brain, blood, kidney, liver, spleen, thyroid, and tumor tissues were weighed, and radioactivity counted in a gamma counter. The tissue distribution of radioactivity was then correlated to brain histology.

Figure 12:
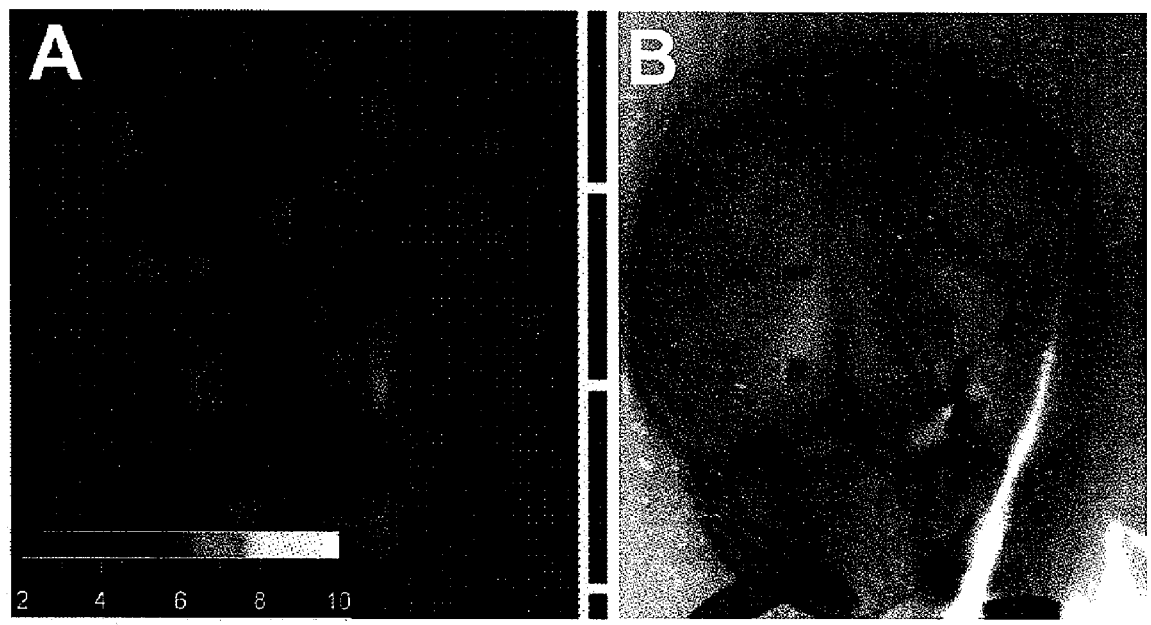
FIG. 12. Bioscan image (4 days after IV injection of $^{125}$I-NM404) of sham control rat brain (A) and same Bioscan image superimposed over the corresponding digital photograph of excised rat brain showing low background level of NM404 in normal brain tissue.
Figure 13:
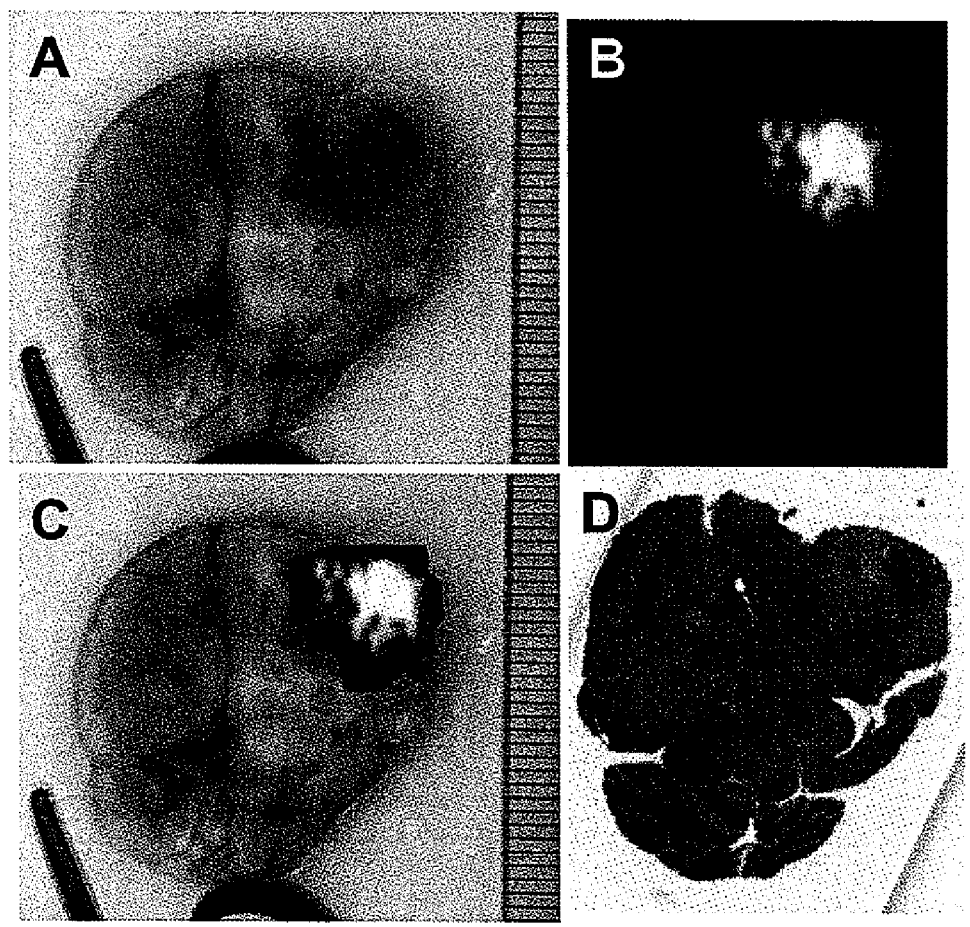
FIG. 13. Digital photograph (A) and corresponding Bioscan image of excised C6-glioma bearing rat brain (B) 4 days after IV injection of $^{125}$I-NM404. Position and size-matched fused Bioscan image and photograph (C) indicates intense localization of NM404 in tumor. The presence of tumor was histologically confirmed in H&E stained sample in D.

Results and Discussion: Initial imaging results with NM404 indicated striking uptake and prolonged retention in all gliomas ranging from 3-5 mm in diameter. Radioactivity in normal brain tissue was minimal in sham operated control animals (FIG. 12), whereas NM404 concentrated intensely in gliomas (FIG. 13). Tumor to brain ratios (% injected dose/g) in C6-bearing rats were 10.5, 12.2, and 6.7 at 24, 48, and 96 h, respectively. As has been observed in previous cell culture and in vivo animal model studies, NM404 is apparently metabolized and eliminated from normal cells but becomes metabolically trapped in tumor cell membranes. Previous autoradiography experiments in other tumor models have suggested that only viable tumor cells, and not normal tissue or necrotic tissues, are capable of accumulating NM404. Interestingly, even small tumors measuring a few mm in diameter, were also detected after NM404 administration. These preliminary findings suggest that NM404 may also be useful for visualization of small invasive tumor foci.

Conclusion: As has been the case in all tumor models examined previously, NM404 displayed selective and prolonged retention by rat C6-gliomas evaluated in this study.

F. Example VI

Murine Liver Tumor

Preliminary results obtained in over 14 xenograft and spontaneous tumor models have universally shown NM404 to undergo selective uptake and prolonged retention in tumors. Further, because NM404 affords lower liver background levels than its predecessors, the inventors expanded evaluation into liver tumors in light of the fact that imaging patients with HCC has been problematic. Many patients have underlying cirrhosis and therefore it is difficult to distinguish regenerating nodules from HCC on cross sectional imaging. Moreover, preliminary studies evaluating PET scanning with FDG have shown only 20-50% sensitivity in detecting the disease. Verhoef C, Valkema R. et al., Liver (2002) 22:51-56.

Materials and Methods: Endogenous Mouse HCC Model. The development of spontaneous hepatocellular cancer in endogenous mice over expressing the TGFα gene has been extensively evaluated and is an extremely promising animal model for study of this disease. Lee G H, Merlino G, Fausto N. Cancer Research (1992) 52:5162-5170. TGFα is a mitogen for epithelial cells and binds to the EGF receptor; unregulated expression of TGFα results in tumor formation. In male CD1 mice expressing the transgene TGFα under the control of the zinc-inducible metallothionine 1 (MT1) promoter, 75-80% develop HCC after 12 months of age. However, when the alkylating agent diethyinitrosamine (DEN), a chemical carcinogen, is used to induce tumor growth at 15 days of life, 90% of mice develop HCC by 6 months of age. On histologic examination, these tumors consist of well differentiated hepatocellular carcinomas of a solid pattern. Because the tumors arise spontaneously, the inventors utilize these animals as a suitable model for preclinical studies.

CT26 Colon Adenocarcinoma Xenograft Model: In addition to the spontaneous HCC model, NM404 was also evaluated in a xenograft colon adenocarcinoma tumor model whereby CT26 cells (5×10$^5$ cells/50 µl) were previously injected directly into the liver parenchyma of female BALB/c mice for creation of focal liver tumors.

Imaging Studies: NM404 (FIG. 3A, 100 µg) was radioiodinated with $^{125}$I via isotope exchange in a melt of pivalic acid. Weichert J P, et al., Int J Applied Radiat Isot (1986) 37(8):907-913. Following HPLC purification it was dissolved in an aqueous 2% Polysorbate 20 solution prior to tail vein injection (15 µCi/20 g mouse) into 3 TGFα endogenous mice or alternatively into 3 CT26-tumor bearing mice. Mice were anesthetized and scanned for up to 21 days post injection on a modified Bioscan AR2000 radio-TLC scanner (1 mm increments at 2 min acquisition/lane and 1 mm high-resolution collimator) and also in an ImTek microCT scanner (390 steps) for anatomic correlation. MicroCT images were displayed using Amira software. At sacrifice, tumor-bearing livers were initially excised and scanned ex vivo. Tumors were then excised, weighed, scanned ex vivo, and radioactivity quantitated. Lesion samples were submitted for histologic classification.

Figure 14:
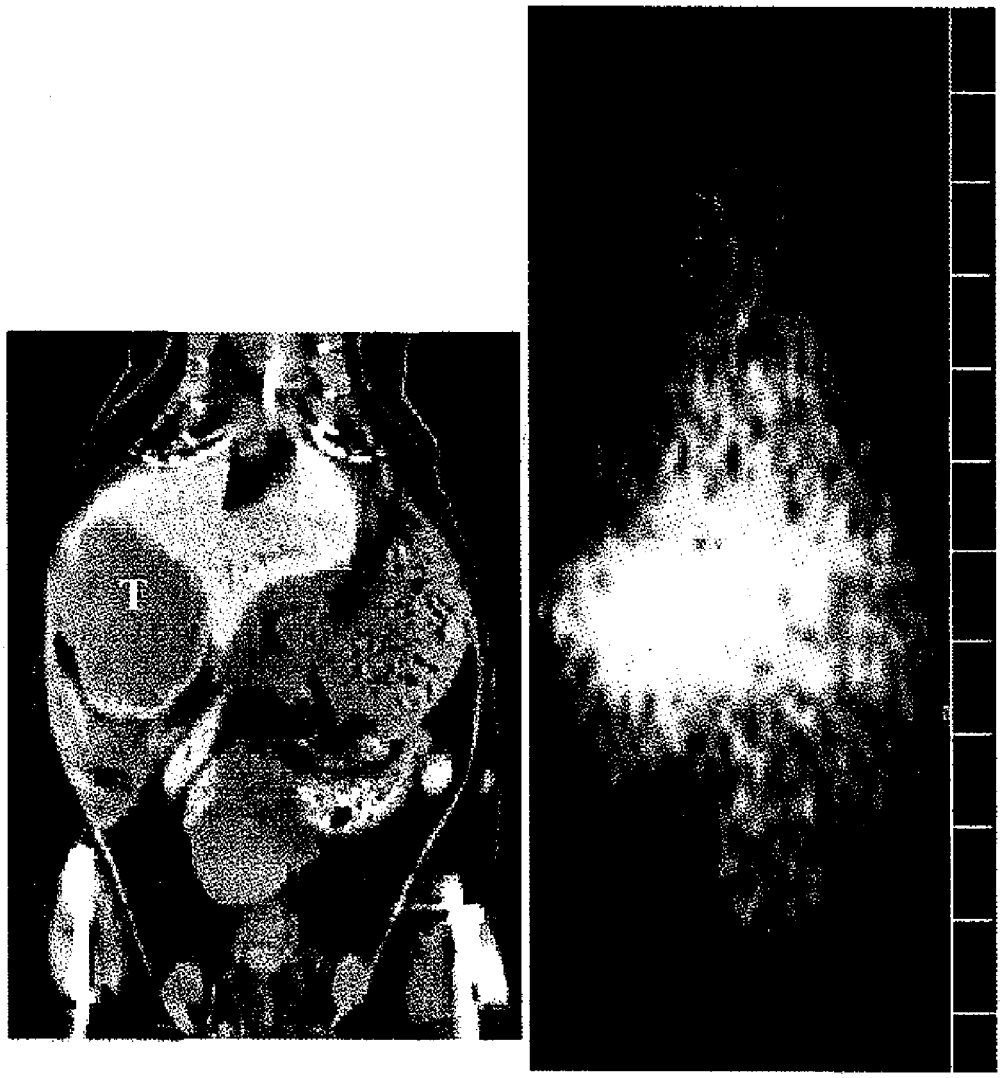
FIG. 14. Coronal microCT scan (left) and dorsal Bioscan image (right) of a TGFα hepatoma-bearing mouse 10 days post $^{125}$I-NM404 injection. Liver is enhanced on microCT image with ITG, a hepatocyte-selective CT contrast agent (Tumor=T).
Figure 15:
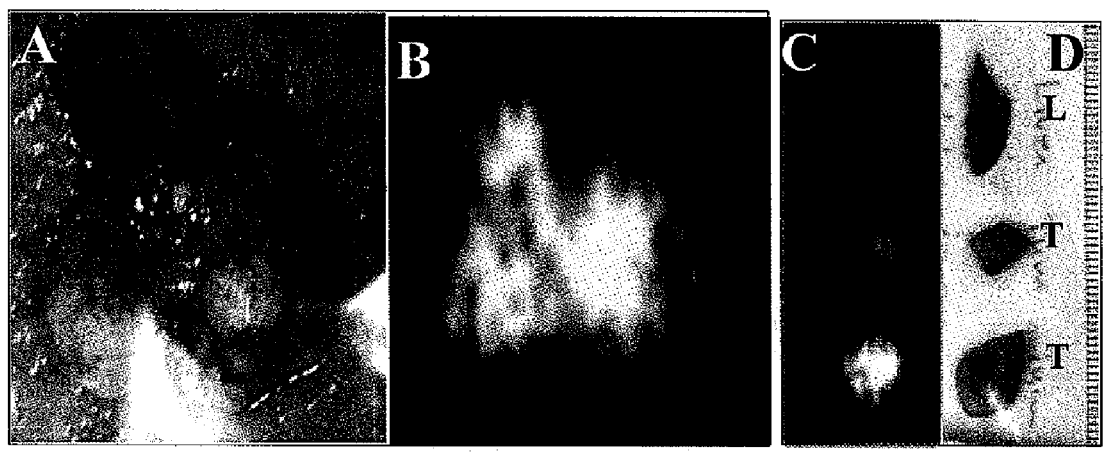
FIG. 15. Photograph (A) and Bioscan image (B) of excised CT-26 tumor-bearing mouse liver 7 days post NM404 injection. Liver tumor involvement was extensive. Tumor implant occurred 15 days prior to this scan. Bioscan image (C) and photograph (D) of excised dissected tumors (T) and normal uninvolved liver (L).
Figure 16:
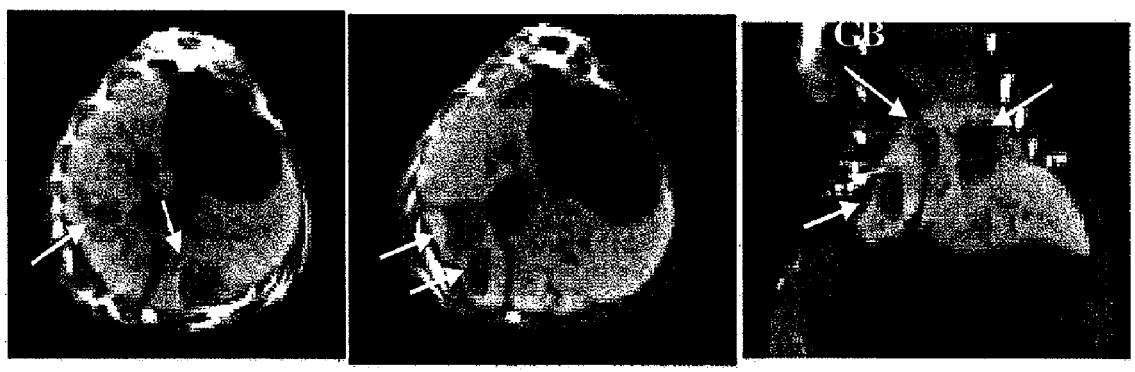
FIG. 16. MicroCT of same mouse presented in FIG. 15 showing the presence of multiple CT26 tumors. Liver was enhanced using ITG, a hepatocyte-selective contrast agent. These images were acquired 10 days post tumor cell implantation and 5 days prior to the Bioscan images above. (Tumors depicted by arrows and gall bladder=GB).

Results and Discussions: Initial imaging results with NM404 (FIGS. 14, 15) have shown striking uptake (>20% dose/g) and prolonged retention in both spontaneous and implanted carcinomas in the liver. Tumor retention of NM404 persisted in these animals for 21 days, the predetermined study endpoint. Contrast-enhanced microCT images confirmed the presence and precise location of all liver tumors (FIGS. 14, 16). Lipid extraction and subsequent HPLC analysis of tumor tissue indicated that the radioactivity was still associated with parent compound. As has been observed in previous cell culture and in vivo animal model studies, NM404 apparently is metabolized and eliminated from normal cells, but becomes metabolically trapped in tumor cell membranes Conclusions: As has been the case in all prior tumor models examined, NM404 displayed selective and prolonged retention by both spontaneous and xenograft murine liver tumor models evaluated in this study.

G. Example VII

Apc$^{Min}$/+ Spontaneous Mammary Carcinoma Model

Materials and Methods: Apc$^{Min}$/+ Mouse Model: This model is comprised of mice carrying the Min allele of Apc (Apc$^{Min}$/+ mice). This model offers specific advantages over xenograft models in that female Apc$^{Min}$/+ mice are predisposed to develop mammary hyperplasias and carcinomas and intestinal adenomas. On the C57BL/6J genetic background, about 5% of untreated females will develop a mammary tumor by 100 days of age. Moser A R, Dove, et al. *Proc Natl Acad Sci USA* (1993) 90:8977-81. The incidence and multiplicity of the mammary lesions can be increased by a single dose of ethyinitrosourea (ENU), a direct acting alkylating agent. Treatment with ENU results in 90% of B6 Apc$^{Min}$/+ females developing an average of 3 mammary squamous cell carcinomas (SCC), but few hyperplasic lesions within 60 days after treatment.

Apc$^{Min}$/+ mice carry a single base pair change in the Apc (adenomatous polyposis coli) gene. The APC/Apc gene encodes a large protein with several potential functional domains. Groden, J., Thliveris, A., Samowitz, W., Carlson, M., Gelbert, L., Albertsen, H., Joslyn, G., Stevens, J., Spirio, L., Robertson, M. and et al. Identification and characterization of the familial adenomatous polyposis coli gene. *Cell*, (1991) 66, 589-600; Kinzler, K. W., Nilbert, M. C., Vogelstein, B., Bryan, T. M., Levy, D. B., Smith, K. J., Preisinger, A. C., Hamilton, S. R., Hedge, P., Markham, A. and et al. Identification of a gene located at chromosome 5q21 that is mutated in colorectal cancers. *Science*, (1991) 257, 1366-70. The mouse and human APC proteins are 90% identical and all potential functional domains are conserved. APC regulates β-catenin levels. β-catenin has multiple roles in the cell, including stabilization of E-cadherin and regulation of transcription through the LEF and TCF family of transcription factors. Aberle, H., Schwartz, H. and Kemler, R. Cadherin-Catenin Complex—Protein Interactions and Their Implications For Cadherin Function. *Journal of Cellular Biochemistry*, (1996) 67, 514-523; Huber, O., Korn, R., McLaughlin, J., Ohsugi, M., Herrmann, B. G. and Kemler, R. Nuclear localization of beta-catenin by interaction with transcription factor LEF-1. *Mechanisms of Development*, (1996) 59, 3-10; Behrens, J., Vonkries, J. P., Kuhl, M., Bruhn, L., Wedlich, D., Grosschedl, R. and Birchmeier, W. Functional Interaction of Beta-Catenin With the Transcription Factor Lef-1. *Nature*, (1996) 382, 638-642. The regulation of β-catenin levels involves the interaction of APC, axin or conductin, and glycogen synthase kinase 3β (GSK3β) with β-catenin. Behrens, J., Jerchow, B. A., Wurtele, M., Grimm, J., Asbrand, C., Wirtz, R., Kuhl, M., Wedlich, D. and Birchmeier, W. Functional interaction of an axin homolog, conductin, with beta-catenin, APC, and GSK3beta. *Science*, (1998) 280, 596-9; Ikeda, S., Kishida, S., Yamamoto, H., Murai, H., Koyama, S. and Kikuchi, A. Axin, a negative regulator of the Wnt signaling pathway, forms a complex with GSK-3beta and beta-catenin and promotes GSK-3beta-dependent phosphorylation of beta-catenin. *EMBO Journal*, (1998) 77, 1371-84; Kishida, S., Yamamoto, H., Ikeda, S., Kishida, M., Sakamoto, I., Koyama, S. and Kikuchi, A. Axin, a negative regulator of the wnt signaling pathway, directly interacts with adenomatous polyposis coli and regulates the stabilization of beta-catenin. *Journal of Biological Chemistry*, (1998) 273, 10823-6; Sakanaka, C., Weiss, J. B. and Williams, L. T. Bridging of beta-catenin and glycogen synthase kinase-3beta by axin and inhibition of beta-catenin-mediated transcription. *Proceedings of the National Academy of Sciences of the United States of America*, (1998) 95, 3020-3; Rubinfeld, B., Albert, I., Porfiri, E., Fiol, C., Munemitsu, S. and Polakis, P. Binding of GSK3beta to the APC-beta-catenin complex and regulation of complex assembly. *Science*, (1996) 272, 1023-6; Rubinfeld, B., Souza, B., Albert, I., Muller, O., Chamberlain, S. H., Masiarz, F. R., Munemitsu, S. and Polakis, P. Association of the APC gene product with beta-catenin. *Science*, (1993) 262, 1731-4; Polakis, P. The adenomatous polyposis coli (APC) tumor suppressor. *Biochimica et Biophysica Acta*, (1997) 7332, F127-47. This interaction results in the phosphorylation of β-catenin, which targets it for degradation by the ubiquitin-proteasome pathway. Rubinfeld, B., Souza, B., Albert, I., Muller, O., Chamberlain, S. H., Masiarz, F. R., Munemitsu, S. and Polakis, P. Association of the APC gene product with beta-catenin. *Science*, (1993) 262, 1731-4; Su, L. K., Vogelstein, B. and Kinzler, K. W. Association of the APC tumor suppressor protein with catenins. *Science*, (1993) 262, 1734-7; Polakis, P. Mutations in the APC gene and their implications for protein structure and function. *Current Opinion in Genetics & Development*, (1995) 5, 66-71; Aberle, H., Bauer, A., Stappert, J., Kispert, A. and Kemler, R. beta-catenin is a target for the ubiquitin-proteasome pathway. *EMBO Journal*, (1997) 76, 3797-804. Most germline and somatic mutations in APC result in proteins missing some or all of the β-catenin binding sites.[26,28,29] Polakis, P. Mutations in the APC gene and their implications for protein structure and function. *Current Opinion in Genetics & Development*, (1995) 5, 66-71; Nagase, H. and Nakamura, YMutations of the APC (adenomatous polyposis coli) gene. *Human Mutation*. (1993) 2, 425-34; Beroud, C. and Soussi, T. APC gene: database of germline and somatic mutations in human tumors and cell lines. *Nucleic Acids Research*, (1996) 24, 121-4.Two regions of APC are required for this interaction; the truncated protein encoded by the Min allele lacks both of these regions; Polakis, P. Mutations in the APC gene and their implications for protein structure and function. *Current Opinion in Genetics & Development*, (1995) 5, 66-71; Su, L. K., Kinzler, K. W., Vogelstein, B., Preisinger, A. C., Moser, A. R., Luongo, C., Gould, K. A. and Dove, W. F. Multiple intestinal neoplasia caused by a mutation in the murine homolog of the APC gene. *Science*, (1992) 256, 668-70. APC also has a role in the transport of β-catenin out of the nucleus. Thus, in the absence of APC function, β-catenin would accumulate in the cytoplasm and nucleus, possibly affected both transcription of target genes and cell-cell interaction through E-cadherin. APC mutations are frequent in several tumor types in humans including intestinal tumors and other epithelial tumors. Loss of heterozygosity at the APC locus or increased levels of β-catenin have been found in more than 25% of breast cancers. Furuuchi, K., Tada, M., Yamada, H., Kataoka, A., Furuuchi, N., Hamada, J., Takahashi, M., Todo, S., and Moriuchi, T. Somatic mutations of the APC gene in primary breast cancers. *Somatic mutations of the APC gene in primary breast cancers, American Journal of Pathology*. (2000) 156: 1997-2005; Jonsson, M., Borg, A., Nilbert, M., and Andersson, T. Involvement of adenomatous polyposis coli (APC)/beta-catenin signaling in human breast cancer. *Involvement of adenomatous polyposis coli (APC)/beta-catenin signaling in human breast cancer, European Journal of Cancer*. (2000) 36: 242-248. Thus, the types of lesions that appear in these mice will be molecularly and histologically similar to breast cancers in humans.

Genetic background can affect the incidence, latency, and type of mammary lesions that develop. For example, FVBxB6 Apc$^{Min}$/+ female mice develop an average of 0.2 mammary tumors per mouse, but 4 hyperplasias per mouse within 120 days of treatment. BALB/xB6 Apc$^{Min}$/+ develop an average of 1.8 mammary tumors and 0.6 hyperplasias per mouse. Moser A R, Hegge L F, Cardiff R D. *Cancer Research* (2001) 61:3480-3485. FVBxB6 and BALBxB6 Apc$^{Min}$/+ mice develop both mammary SCC and adenocarcinomas (AC).

The hyperplastic lesions in the FVBxB6 Apc$^{Min}$/+ mice can be classified as either alveolar hyperplasias or squamous nodules. Moser, A. R., Hegge, L. F., and Cardiff, R. D. Genetic background affects susceptibility to mammary tumors and hyperplasias in Apc$^{Min}$/+ mice, Genetic background affects susceptibility to mammary tumors and hyperplasias in Apc$^{Min}$/+ mice. *Cancer Research* (2001) 61:3480-3485. Alveolar hyperplasias are precursors to the adenocarcinomas and the squamous nodules are precursor lesions to the SCC. Thus, by manipulation of the genetic background, mice that develop multiple types of hyperplasias and carcinomas may be generated, often within the same animal. The alveolar hyperplasias resemble atypical lobules (type A) commonly found in samples from human breasts. Cardiff, R. D. and Wellings, S. R. The comparative pathology of human and mouse mammary glands. *The comparative pathology of human and mouse mammary glands, Journal of Mammary Gland Biology & Neoplasia*. (1999) 4: 105-22. These atypical lobules are more common in cancerous breasts or in the contralateral breast in women with breast cancer. While SCC is not a frequent type of breast tumor, the AC resembles a common type of human breast tumor. In addition, tumors with alterations in the APC pathway are common in human breast cancers. Loss of heterozygosity at the APC locus or increased levels of β-catenin have been found in more than 25% of breast cancers. Furuuchi, K., Tada, M., Yamada, H., Kataoka, A., Furuuchi, N., Hamada, J., Takahashi, M., Todo, S., and Moriuchi, T. Somatic mutations of the APC gene in primary breast cancers. *Somatic mutations of the APC gene in primary breast cancers, American journal of Pathology*. (2000) 156::1997-2005.35. Jonsson, M., Borg, A., Nilbert, M., and Andersson, T. Involvement of adenomatous polyposis coli (APC)/beta-catenin signaling in human breast cancer. *Involvement of adenomatous polyposis coli (APC)/beta-catenin signaling in human breast cancer, Eur Journal of Cancer*. (2000) 36: 242-248. Thus, the types of lesions that appear in these mice will be molecularly and histologically similar to breast cancers in humans. One of the unique aspects and strengths of this model is the ability to generate mice that develop multiple types of mammary hyperplasias and carcinomas, often within the same animal. In this way we can test the uptake and retention of NM404 in multiple types of hyperplasias and tumors within the same animal.

Polyoma virus infection of mice leads to the development of numerous tumor types including mammary tumors. Endogenous mice expressing the polyoma middle T antigen (PyVT) under the control of the mouse mammary tumor virus LTR (MMTV) develop multifocal mammary dysplasias and tumors rapidly. Amy Moser; Guy, C. T., Cardiff, R. D., and Muller, W. J. Induction of mammary tumors by expression of polyomavirus middle T oncogene: a endogenous mouse model for metastatic disease. *Induction of mammary tumors by expression of polyoma virus middle T oncogene: a transgenic mouse model for metastatic disease, Molecular & Cellular Biology*. (1992) 12: 954-61. Evidence for in situ carcinoma can be seen as early as three weeks of age, with 100% incidence of mammary tumors by as early as 5 weeks of age. The tumors are primarily classified as AC and/or adenoacanthomas. The mice develop multiple metastatic lesions in the lung within 50 days of the appearance of the primary tumor Lifsted, T., Le Voyer, T., Williams, M., Muller, W., Kleinszanto, A A., Buetow, K. H., and Hunter, K. W. Identification of inbred mouse strains harboring genetic modifiers of mammary tumor age of onset and metastatic progression. *Identi-* fication of inbred mouse strains harboring genetic modifiers of mammary tumor age of onset and metastatic progression, Int J of Cancer. (1998) 77: 640-4. Thus, these mice provide a rapid model for metastatic mammary cancer. As with the Apc$^{Min}$/+ mice, genetic background affects the time course of tumor development and metastatic spread. Lifsted, T., Le Voyer, T., Williams, M., Muller, W., Klein-Szanto, A A., Buetow, K. H., and Hunter, K. W. Identification of inbred mouse strains harboring genetic modifiers of mammary tumor age of onset and metastatic progression. *Identification of inbred mouse strains harboring genetic modifiers of mammary tumor age of onset and metastatic progression, Int J of Cancer.* (1998) 77: 640-4. Thus, the inventors use crosses to generate mice with a slower course of tumor development. PyVT can associate with members of the SRC kinase family, phosphatidylinositol-3"kinase, the SHC adapter protein and protein phosphatase 2A. Dankort, D. L. and Muller, W. J. Transgenic models of breast cancer metastasis. *Transgenic models of breast cancer metastasis, Cancer Treatment & Research.* (1996) 83: 71-88. Activation of SRC family kinases is frequently observed in human breast tumors. Amy Moser;Muthuswamy, S. K. and Muller, W. J. Activation of the Src family of tyrosine kinases in mammary tumorigenesis. *Activation of the Src family of tyrosine kinases in mammary tumorigenesis, Advances in Cancer Research* (1994) 64: 111-23.

Figure 19:
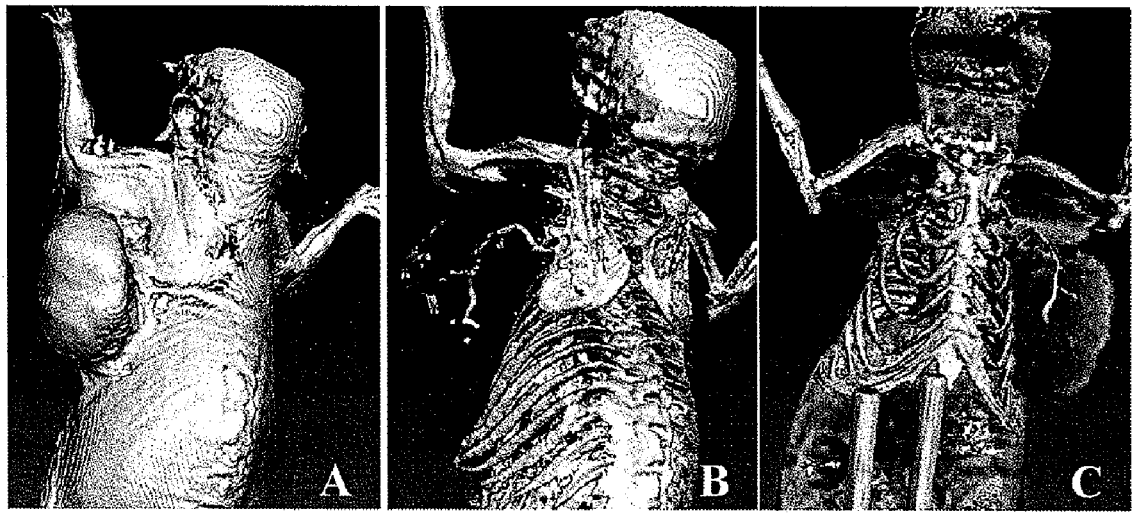
FIG. 19. MicroCT scans of Min mouse of FIG. 18. Panel A is a low density surface rendering showing a large left axillary mammary tumor. Panel B is the high density surface rendering after blood pool CT contrast agent BP10 was administered to help locate tumor feeder vessels. Panel C is a composite coronal CT image and high density surface rendering showing absolute feeder vessel localization. Orientation is from beneath in panel C, whereas Panels A and B are viewed from above.

Imaging Studies: NM404 (FIG. 3A, 100 µg) was radioiodinated with $^{125}$I via isotope exchange in a melt of pivalic acid. Following HPLC purification it was dissolved in an aqueous 2% tween-20 solution prior to tail vein injection (15 µCi/20 g mouse) into 6 female Apc$^{Min}$/+ mice. Mice were anesthetized and scanned for up to 50 days post-injection on a modified Bioscan AR2000 radio-TLC scanner (1 mm increments at 2 min acquisition/lane and 1 mm high-resolution collimator) and also in an ImTek microCT scanner (390 steps) for anatomic comparison. MicroCT images were displayed using Amira software. At sacrifice, mammary glands or excised tumors were imaged ex vivo, lesions were excised, weighed, and radioactivity quantitated. Lesion samples were submitted for histologic classification. If necessary a long-acting CT blood pool contrast agent (BP10), developed in the inventors' lab and suitable for long microCT acquisition times was injected intravenously prior to CT scanning in order to assist in blood vessel visualization. (FIG. 19). Weichert J P, et al., *Radiology* (2000) 216:865-871.

Figure 17:
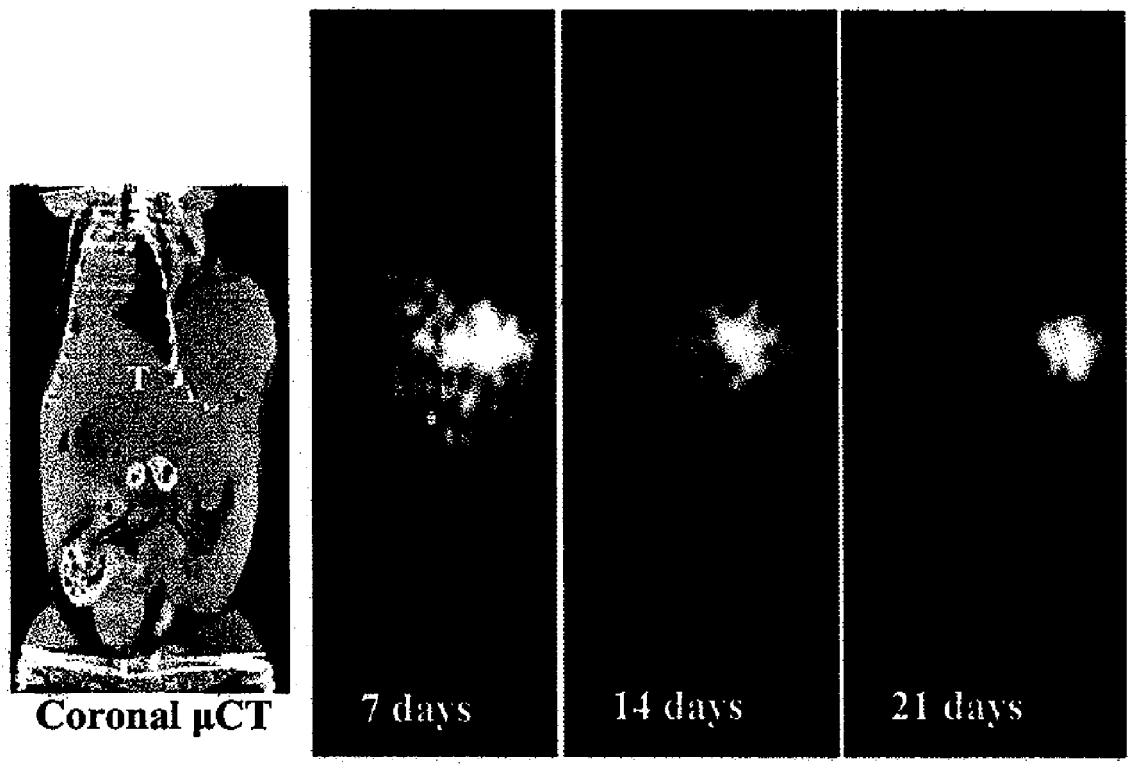
FIG. 17. NM404 Bioscan images of Min mouse with spontaneous right axillary mammary tumor (10 mm dia) at various times following IV administration of $^{125}$I-NM404 (15 μCi). Coronal microCT image (non-contrast-enhanced) is shown for anatomic comparison (left panel, T=tumor).
Figure 18:
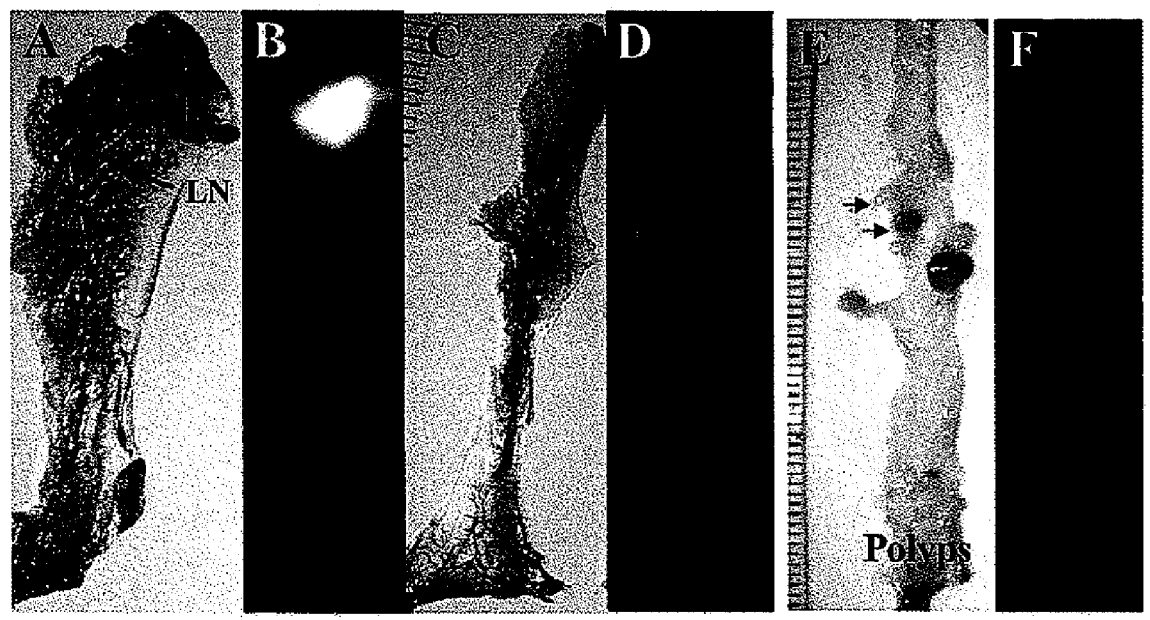
FIG. 18. Carmine stained photographs (A,C) and Bioscan images (B,D) of excised left and right abdominal mammary glands. Note 2 mm tumor in panel A (T) which is easily detected in Bioscan Image (B) of the left gland. Lymph node (small arrow in A) shows no uptake of NM404. No tumors were visually detected in the right gland (C, D). Photograph (E) and Bioscan image (F) of colon indicates no uptake of NM404 in adenomatous polyps (arrows).

Results and Discussion: This model is unique in that hyperplastic mammary lesions, mammary carcinomas, and intestinal adenomas develop in the same mouse. Initial imaging results with NM404 (FIGS. 17, 18) have shown striking uptake (>20% dose/g) and prolonged retention in all spontaneous mammary carcinomas ranging from 2-15 mm in diameter. Although tumor localization appears rapid, background radioactivity persists for several days in liver and gut during the body clearance phase. HPLC analysis of radioactive urine and feces indicated the presence of metabolites and no parent NM404. Tumor retention of NM404 persisted for 50 days, the predetermined study endpoint. NM404 did not localize, however, in intestinal adenomatous polyps found frequently in these mice (FIG. 18). MicroCT images confirmed the presence and precise location of all mammary tumors (FIG. 19). Lipid extraction and subsequent HPLC analysis of tumor tissue indicated that the radioactivity was still associated with parent compound. As has been observed in previous cell culture studies, NM404 apparently is metabolized and eliminated from normal cells but becomes metabolically trapped in tumor cell membranes.

Conclusions: NM404 has displayed striking tumor avidity in animal and human xenograft tumor models examined to date. Moreover, while it displayed selective and prolonged retention by mammary tumors in this spontaneous tumor model it did not localize in associated intestinal adenomatous polyps.

H. Example VIII

Specificity for Hyperplasia versus Neoplasia in the Apc$^{Min}$/+ Endogenous Mammary Adenocarcinoma Model Materials and Methods: Apc$^{Min}$/+ Mouse Model: This model is comprised of mice carrying the Min allele of Apc (Apc$^{Min}$/+ mice). This model offers specific advantages over xenograft models in that female Apc$^{Min}$/+ mice are predisposed to develop mammary hyperplasias and carcinomas and intestinal adenomas. On the C57BL/6J genetic background, about 5% of untreated females will develop a mammary tumor by 100 days of age. Moser A R, Dove, et al. *Proc Natl Acad Sci* USA (1993) 90:8977-81. The incidence and multiplicity of the mammary lesions can be increased by a single dose of ethyinitrosourea (ENU), a direct acting alkylating agent. Treatment with ENU results in 90% of B6 Apc$^{Min}$/+ females developing an average of 3 mammary squamous cell carcinomas (SCC), but few hyperplasic lesions within 60 days after treatment.

Genetic background can affect the incidence, latency, and type of mammary lesions that develop. For example, FVBxB6 Apc$^{Min}$/+ female mice develop an average of 0.2 mammary tumors per mouse, but 4 hyperplasias per mouse within 120 days of treatment. BALB/xB6 Apc$^{Min}$/+ develop an average of 1.8 mammary tumors and 0.6 hyperplasias per mouse. Moser A R, Hegge L F, Cardiff R D. *Cancer Research* (2001) 61:3480-3485. FVBxB6 and BALBxB6 Apc$^{Min}$/+ mice develop both mammary SCC and adenocarcinomas (AC).

Figure 22:
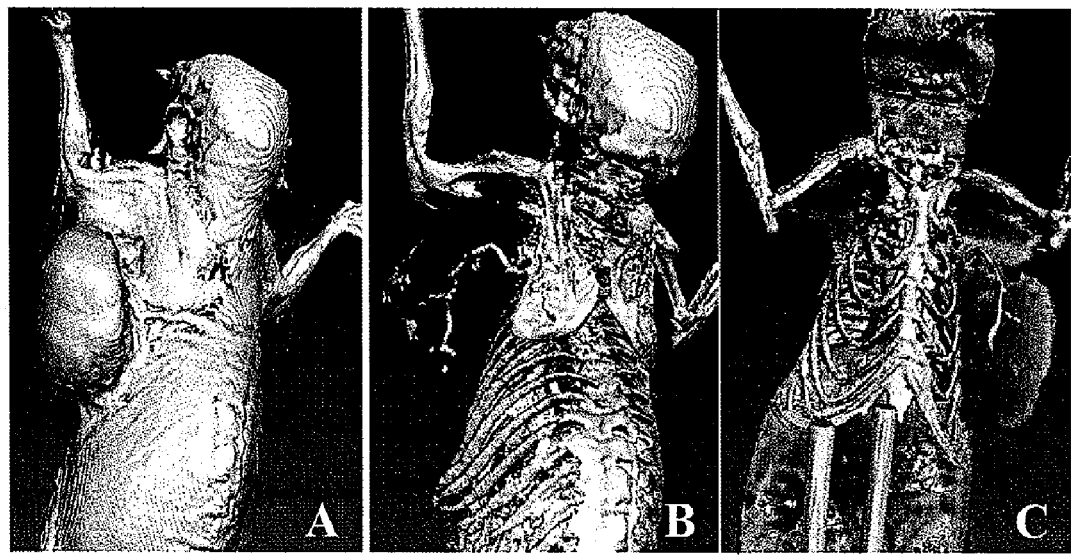
FIG. 22. MicroCT scans of Min mouse shown in FIG. 21. Panel A is a low density surface rendering showing a large left axial mammary tumor. Panel B is the high density surface rendering after blood pool CT contrast agent BP10 was administered to help locate tumor feeder vessels. Panel C is a composite coronal CT image and high density surface rendering showing absolute feeder vessel localization. Orientation is from beneath in panel C, whereas Panels A and B are viewed from above.

Imaging Studies: NM404 (FIG. 3A, 100 µg) was radioiodinated with $^{125}$I via isotope exchange in a melt of pivalic acid. Following HPLC purification it was dissolved in an aqueous 2% tween-20 solution prior to tail vein injection (15 µCi/20g mouse) into 6 female Apc$^{Min}$/+ mice. Mice were anesthetized and scanned for up to 30 days post injection on a modified Bioscan AR2000 radio-TLC scanner (1 mm increments at 2 min acquisition/lane and 1 mm high-resolution collimator) and also in an ImTek microCT scanner (390 steps) for anatomic comparison. MicroCT images were displayed using Amira software. At sacrifice, mammary glands or excised tumors were imaged ex vivo, lesions were excised, weighed, and radioactivity quantitated. Lesion samples were submitted for histologic classification. If necessary a long-acting CT blood pool contrast agent (BP20), developed in the inventors' lab and suitable for long microCT acquisition times was injected intravenously prior to CT scanning in order to assist in blood vessel visualization (FIG. 22). Weichert J P, et al., *Radiology* (2000) 216:865-871.

Figure 20:
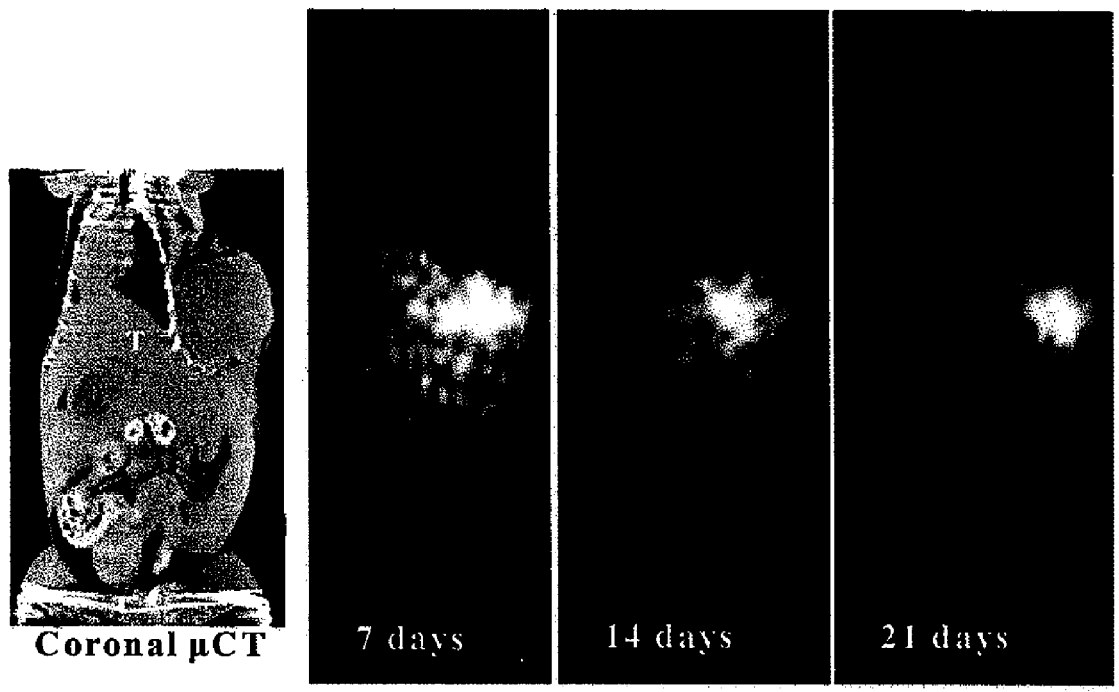
FIG. 20. NM404 Bioscan images of Min mouse with spontaneous right axillary mammary adenocarcinoma (10 mm dia) at various times following IV administration of 125I-NM404 (15 μCi). Coronal microCT image (non-contrast-enhanced) is shown for anatomic comparison (left panel, T=tumor).
Figure 21:
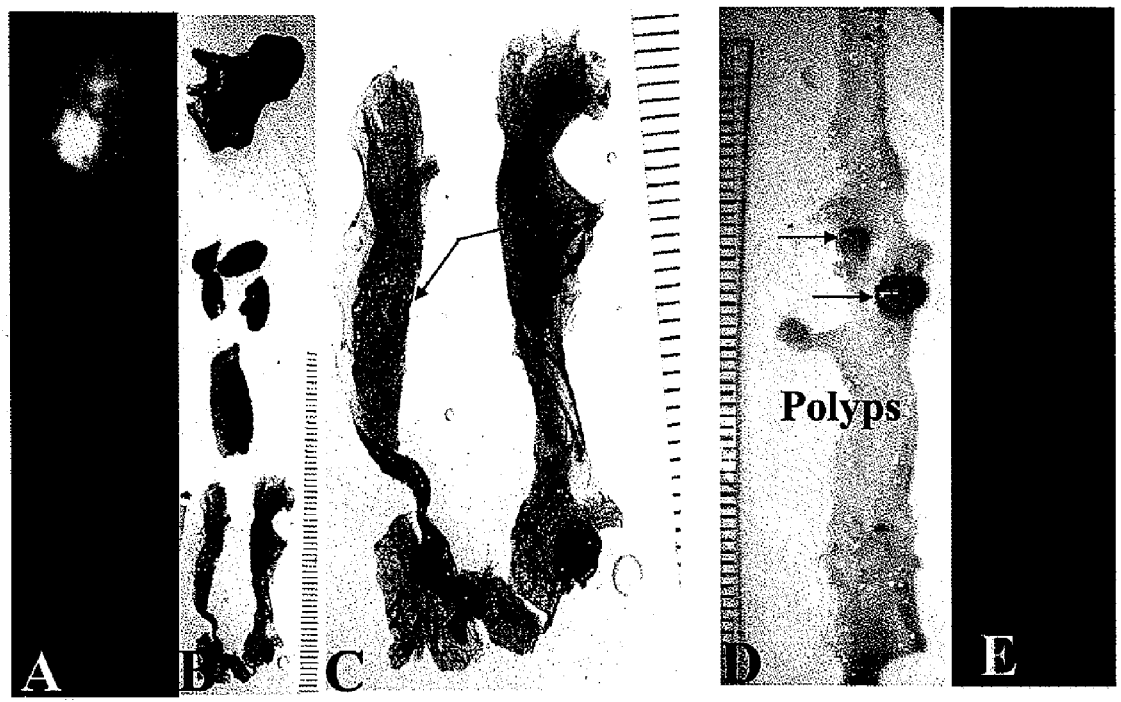
FIG. 21. Bioscan image of excised mammary glands (A) and colon (E) from an FVBxB6Min mouse 8 days post NM404 administration. Corresponding digital photo of same excised tissues in B and D, respectively. Carmine stained enlarged photograph (C) shows the presence of hyperplasias (arrows) but no corresponding focal activity in the Bioscan Image (A). Tumor uptake on Bioscan image (A) corresponds to larger adenocarcinoma in B. Photograph (D) and Bioscan image (E) of excised colon indicates no uptake of NM404 in adenomatous polyps (arrows).

Results and Discussion: This model is unique in that hyperplastic mammary lesions, mammary carcinomas, and intestinal adenomas develop in the same mouse. Initial imaging results with NM404 (FIGS. 20, 21) have shown striking uptake (>20% dose/g) and prolonged retention in all spontaneous mammary carcinomas ranging from 2-15 mm in diameter. Although tumor localization appears rapid, background radioactivity persists for several days in liver and gut during the body clearance phase. HPLC analysis of radioactive urine and feces indicated the presence of metabolites and no parent NM404. Tumor retention of NM404 persisted for >21 days, the predetermined study endpoint. NM404 did not localize, however, in either focal alveolar hyperplasias or in intestinal adenomatous polyps found frequently in these mice (FIG. 21). MicroCT images confirmed the presence and precise location of all mammary tumors (FIG. 22). NM404 apparently is metabolized and eliminated from normal cells but becomes metabolically trapped in tumor cell membranes.

Conclusions: NM404 has displayed striking tumor avidity in 20/20 animal and human xenograft tumor models examined to date. Moreover, while it displayed selective and prolonged retention by mammary adeno- and squamous cell carcinomas in this spontaneous tumor model, it did not localize in associated focal alveolar hyperplasias or intestinal adenomatous polyps and thus appears to be selective for malignant tumor cells.

I. Example IX

Mechanism of Selective Retention of NM404

Introduction: Certain phospholipid ether analogs, such as NM404, are selectively retained within many types of tumor cells for a prolonged time. The inventors sought to evaluate the mechanism of selective retention of NM404 in tumor cells using both an enzymatic assay to evaluate the activity of phospholipase D (PLD) protein and quantitative PCR. The inventors hypothesized that reduced levels of PLD in tumor cells results in a decrease in the ability to metabolize and excrete NM404.

Methods: Single cell suspensions of murine tumor cell lines including hepa-1 (hepatoma), CT26 (colorectal adenocarcinoma), and TS/A (breast adenocarcinoma) were analyzed with two assays: (1) Amplex® Red assay, using a commercially available kit (Molecular Probes) that evaluates PLD protein activity using a fluorescence microplate reader, and (2) quantitative PCR to determine the level of PLD mRNA. Tumor cell lines were compared to normal liver tissue, which exhibits higher levels of uptake and elimination of NM404 and thus likely has lower PLD levels than other normal tissues. For the Amplex® Red assay, total protein was extracted using a detergent solution (Triton-X-100) and quantity of PLD compared to a standard positive control. For PCR, mRNA was purified and converted to cDNA using reverse transcriptase (Promega). Conditions for amplification of cDNA for real-time PCR included: (94° C., 30 sec; 65° C., 30 sec; and 72° C., 30 sec) for 50 cycles (iCycler, iQmix, Bio-Rad). The primer for PLD1, (sense) 5'-TCTGGTTTCAC-CCCGTCAGM-3', (antisense) 5'-TTGCTCATATCTGCG-GCGAT-3', was used. Product was compared to a standard cDNA (GAPDH, Biosource) diluted from 1 μg to $10^{-7}$ μg. All assays were performed in duplicate.

Results: PLD was quantitated as shown in the Table 3. Both PLD protein activity and mRNA levels were significantly lower than normal liver tissue (p<0.05, T-test) in all cell lines.

Conclusion: Both reduced PLD protein activity and a decrease in PLD mRNA were observed in murine tumor cell lines. Thus, the mechanism of selective retention of NM404 may be due to a decrease in the breakdown of NM404 by PLD. Decreased PLD activity in tumor may serve as a potential molecular target for anti-tumor agents.

TABLE 3

| Cell/tissue | PLD protein activity (mU/fluorescence/μg protein/ml) | mRNA (μg × $10^{-5}$/0.01 μg of total cDNA) |
|---|---|---|
| Hepa-1 | 3.3 | 6.2 |
| CT26 | 7.8 | 2.4 |
| TS/A | 2.8 | 4.0 |
| Normal liver | 14.1 | 12.2 |

J. Example X

Therapeutic attributes in Endogenous Murine Mammary Tumor Model

Figure 25:
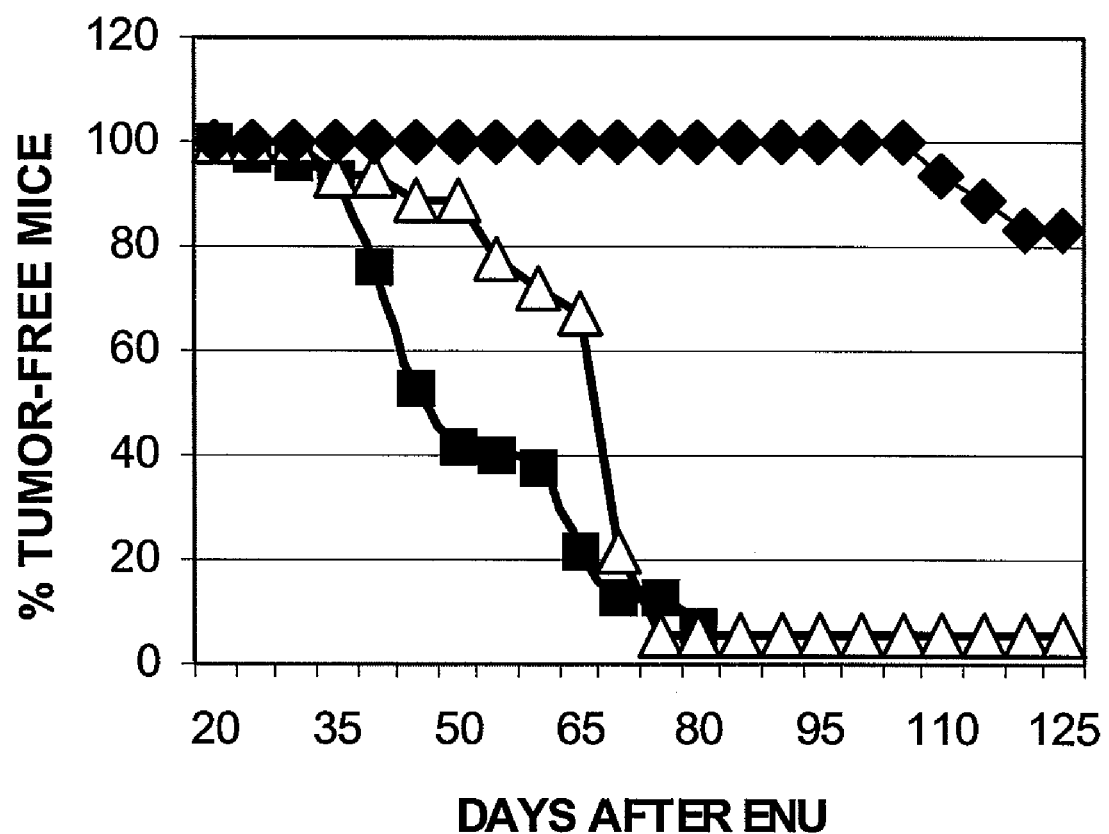
FIG. 25. Time to first tumor in ENU-treated Min/+ mice. Time to first mammary tumor expressed as days after ENU. Female Min/+ mice were treated with ENU and checked twice weekly for the presence of mammary tumors. The time after ENU treatment to first tumor is plotted in 5 day intervals for B6Min/+ (n=45)(□), BRB6 Min/+ (n=18)(Δ), FVBB6 Min/+ (n=18) (◇).
Figure 26:
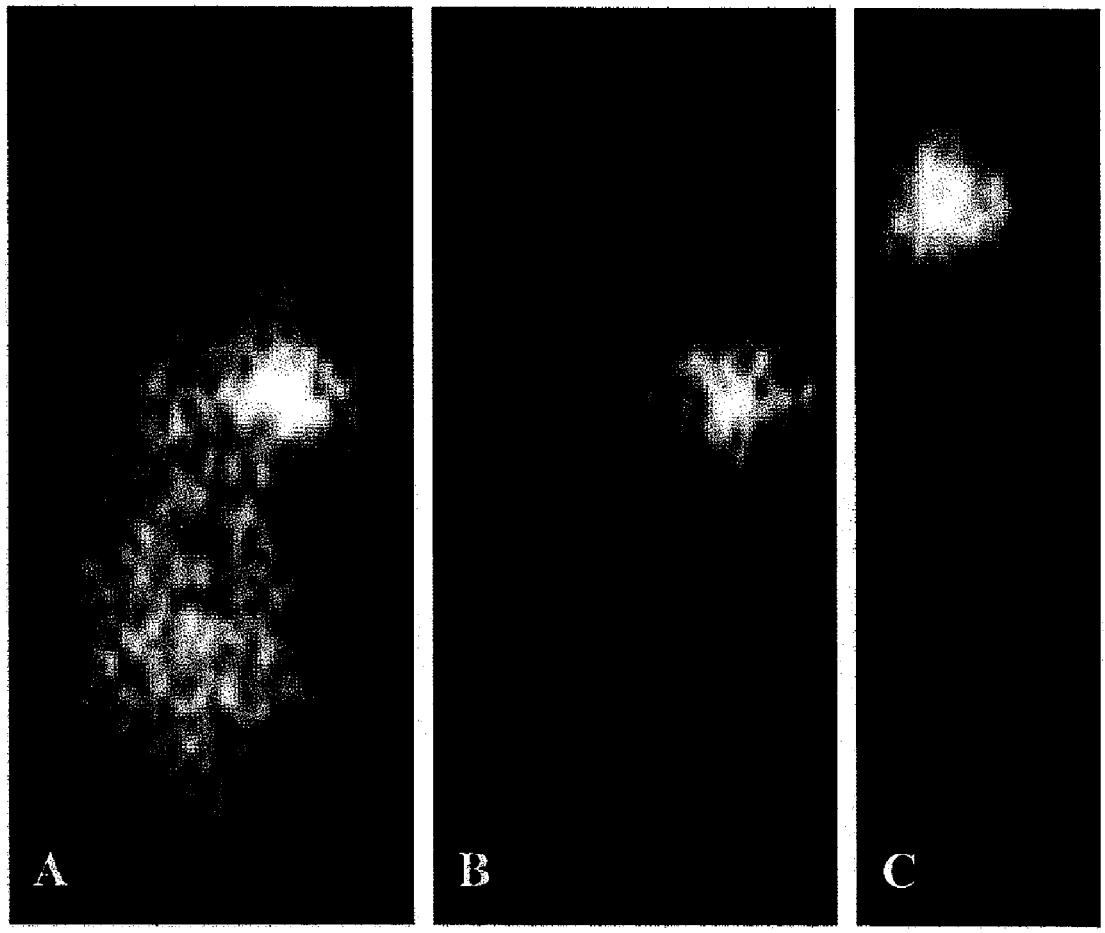
FIG. 26. Bioscan images of prone FVBxB6 min mouse 1 (A) and 7 (B) days post $^{125}$I-NM404 administration indicates presence of large axillary mammary tumor. Bioscan image of excised mammary gland (C) 10 days after injection shows incorporation of NM404 in large 10 mm adenocarcinoma and smaller adjacent 2 mm tumor that wasn't visible in the in vivo scan.

Models for NM404 Therapy Study: Although long-term survival is not essential for imaging studies, it is advantageous for the proposed therapy studies. The models used for imaging studies suffer from concomitant intestinal tumors which usually lead to the death of the animal. In order to increase the number of tumors developing per mouse and decrease the number of intestinal tumors in hopes of increasing the lifespan of the tumor bearing mice, Dr. Moser has recently crossed male B6 Min/+ mice with female C57BR/cdJ (BR) mice. The resulting BRB6 F1 Min/+ female mice developed significantly more mammary tumors than did the B6 Min/+ mice (P=0.016), an average of nearly 5. The number of mice with tumors and the time to first tumor were not different between these two strains (P=1 and P=0.06, respectively) (FIG. 25). The increased mammary tumor number of the BRB6 F1 mice may be due, in part, to the significantly longer survival times of the hybrid BRB6 F1 Min/+ mice relative to the B6 Min/+ mice (P=2×$10^{-7}$).

B6 and BRB6 F1 Min/+ mice were very similar with respect to the mammary gland phenotype, but quite different in susceptibility to intestinal tumors. The B6 and BR strains can be considered sensitive backgrounds for Min-induced mammary tumorigenesis as the mice developed a large number of tumors within a short time after ENU treatment. However, the BR strain carries dominant resistance alleles at modifier loci affecting intestinal tumor development, which may prove relevant to the proposed therapy study. A comparison of these strains is presented in Table 2.

TABLE 2

Genetic background affects mammary and intestinal tumor development in Min/+ mice.

| Strain | # of mice | % with mammary tumor ( ) | Average # of mammary tumors/mouse | # with mammary lesions (%) | Average # of mammary lesions/mouse | Average # of intestinal tumors/mouse | Average survival in days after ENU (range) |
|---|---|---|---|---|---|---|---|
| B6 | 45 | 93 | 3.3 ± 2.0 | 17 (38) | 0.6 ± 0.9 | 34 ± 10 | 64 (43–78) |
| BR × B6 | 18 | 94 | 4.9 ± 2.6 | 7 (39) | 0.5 ± 0.7 | 14 ± 4 | 91 (58–118) |
| FVB × B6 | 18 | 17 | 0.2 ± 0.5 | 18 (100) | 4.1 ± 2.4 | 12 ± 6[a] | 127 (93–178) |

[a] Information on 16 mice as the intestines of 2 mice were lost in processing.

Figure 27:
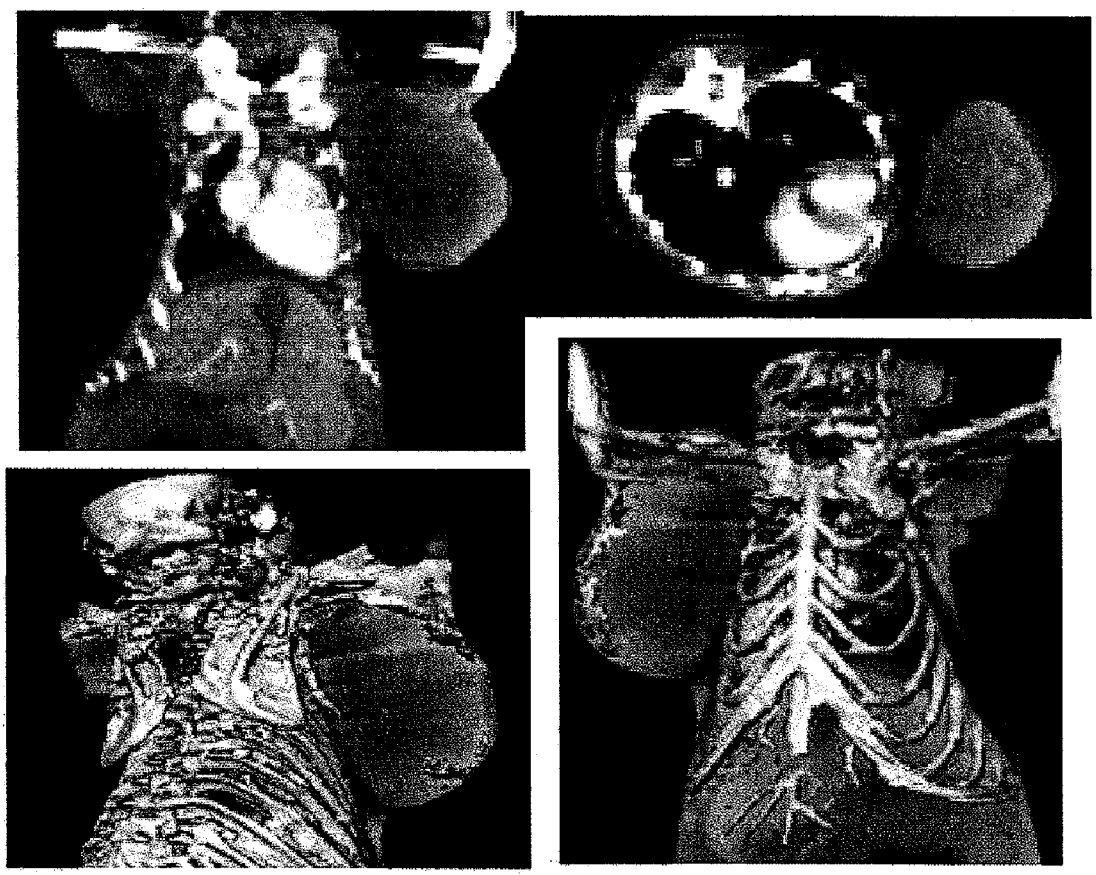
FIG. 27. MicroCT images of same FVBxB6 min mouse, as shown in FIG. 26, showing large axillary mammary tumor. Coronal and axial slices are shown in A and B, whereas 3D-surface (gold) and coronal slices are displayed simultaneously in posterior (C) and anterior (D) views.

Mice were generated by crossing females of each strain with B6 Min/+ males. Female mice were treated with ENU when between 30–45 days of age and sacrificed when moribund. Only the results from the Min/+ mice are shown. Mammary tumors are defined as those tumors identified at necropsy, while mammary lesions are the small focal lesions noted in the whole mounts of the 1st, 4th and 5th mammary glands. Intestinal tumors were counted in three 4 cm sections from the small intestine (duodenum, jejunum, and ileum), and the entire colon. All Min/+ mice developed intestinal tumors. Values are the means ± SD Preliminary Imaging Results with NM404 in Min Mice: In a preliminary experiment to show that NM404 localizes in endogenous FVBxB6 Apc$^{Min}$/+ mouse breast tumors, two animals were injected (IV tail vein) with $^{125}$I-NM404 (15 μCi) and imaged on a modified Bioscan AR2000 radioTLC scanner (equipped with high resolution 1 mm collimator and 2-D acquisition and analysis software) at 1, 4, and 7 days post injection (FIG. 27A,B). Each animal underwent microCT scanning (FIG. 27) on day 10 prior to euthanasia and dissection to remove the mammary glands and associated tumors. Focal hot spots correlated visually with all tumors on ex vivo Bioscan images (FIG. 27C). Although lymph nodes are visible, no radioactivity was associated with them indicating a lack of tumor cell infiltration. The main tumor in FIG. 27C was histologically categorized as an adenocarcinoma. There were four mammary tumors in both mice and all were easily detectable in ex vivo Bioscan images of the excised mammary glands.

Radiotherapeutic Potential of NM404: During the course of recent mouse tumor uptake and retention studies with "imaging" doses (15-20 μCi/20 g mouse) of $^{125}$I-labeled NM404, several apparent therapeutic responses have been observed (unpublished results). In an Apc$^{Min}$/+ mouse mammary tumor model it has generally been noted that tumor growth remains static following a single intravenous injection of NM404. Some of these animals also lost all hair above larger mammary tumors at around 8 days after injection. Moreover, these mice also get intestinal tumors and usually suffer from intestinal bleeding resulting in severe anemia, which renders their feet white. Dr. Moser noted that the feet of these mice had reverted to a pink color around 5 days after a single injection of NM404. Upon eventual dissection of these animals, it was noted that only a very few, if any, of the expected 20 or so intestinal tumors usually found at this age actually remained. The "white to pink feet" phenomenon was also observed in a separate, but more aggressive, mouse intestinal adenocarcinoma model, wherein dissection at 12 days following NM404 administration, again revealed that most, if not all, of the expected intestinal tumors were gone. In both intestinal models, animals that received NM404 easily outlived their untreated litter mates. These coincidental findings were reconfirmed in two separate age-matched groups each involving more than 6 mice. These observations with $^{125}$I-NM404 indicate potential for radiotherapy applications particularly if labeled with iodine-131. Quantitative tumor uptake and retention studies outlined in this proposed mammary tumor model will also provide sufficient data to initiate a comprehensive dosimetry analysis for this agent in order to estimate its true radiotherapeutic potential.

Figure 28:
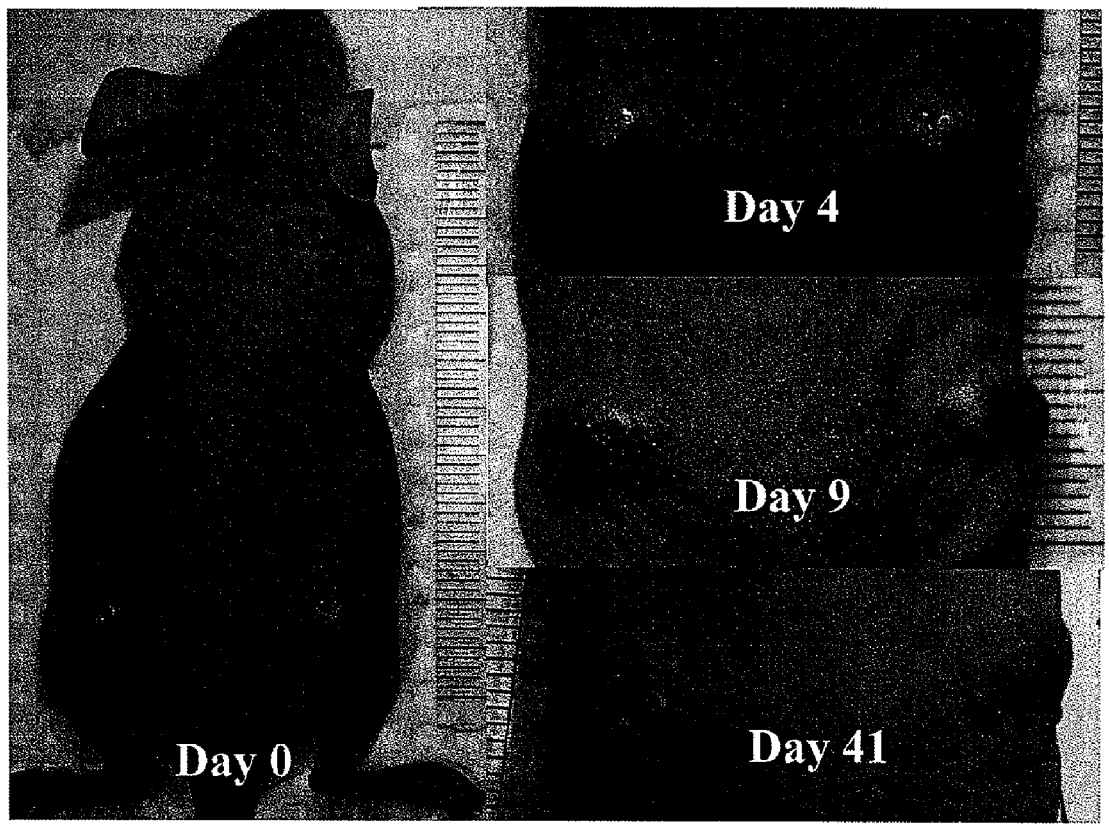
FIG. 28. Apparent SCC1 and 6 Tumor Regression after Injection of $^{125}$I-NM404.

Choice of Isotope: Due to its 60-day physical half-life and low energy 28 KeV photon emission, iodine-125 is suitable for imaging experiments in mice and rats. Iodine-125 also affords therapeutic characteristics as well and is currently used in permanent prostate brachytherapy implants. In one imaging experiment, 2 nude mice were each inoculated with subcutaneous squamous cell 1 and 6 tumor cell implants on opposing flanks. SCC1 and 6 cells were used because one is radiosensitive relative to the other. After 14 days when the average tumor size (4 total) was approaching 0.5 cm in diameter, one of the mice received 20 μCi of $^{125}$I-labeled NM404 and the other one receive unlabeled NM404 in an equal mass dose. The mouse that had received only the unlabeled compound had to be euthanized 20 days after injection due to both tumors reaching the termination size limit as defined in our animal use protocol. Both tumors in the $^{125}$I-NM404 mouse regressed dramatically and unexpectedly over the course of several weeks (FIG. 28). In fact, the tumors of this mouse never did reach terminal size and the mouse was actually euthanized after 90 days in order to collect histology sections. At this time, the center of the tumor had become necrotic while the peripheral rim appeared somewhat viable. Histologic examination confirmed a necrotic center and viable rim. While blood supply factors can contribute to such observations it is also possible that the photon emission from $^{125}$I resulted in poor electron equilibrium at the tumor periphery resulting in under-dosing of the "rind" of the tumor. This electron equilibrium issue is critical in radiation oncology. Photons travel a finite distance, determined by their energy, before interacting with tissue and exerting their biologic effect. A photon with too high an energy can result in under-dosing of the tumor nodule periphery, as photons departing the nodule travel away (out of the tumor) before depositing their dose. This could be a problem with $^{125}$I the photons, however, the low energy insures very local deposition. Complex Monte Carlo calculations could refine such estimates, but the best method for determining optimal isotope selection is experimentation, as there are many factors at play which cannot be modeled accurately (details of tissue distribution, multiple pass, etc). The one advantage of $^{125}$I is that all the photons are of low energy, insuring very limited exposure of normal tissues surrounding the tumor.

Iodine-131 has been used with great efficacy in the treatment of thyroid cancer. Very safe doses of $^{131}$I can control subclinical deposits of well-differentiated thyroid cancer, which concentrates iodine very avidly as does the normal thyroid. This active uptake process helps limit the dose to normal tissues. Iodine-131 has both beta and several gamma emissions, but the predominant tissue dose arises from the beta emissions. The inventors have selected $^{131}$I-labeled NM404 based upon the clinical success with thyroid cancer coupled with results obtained with Bexxar (an iodine-131-labeled antibody-based agent) in low-grade lymphoma patients. The predominant beta emissions and mostly low energy gamma emissions optimize dose homogeneity within the tumor nodule itself. Also, the shorter half-life (8-days) provides more clinically relevant dose-intensity compared to the 60-day half-life of $^{125}$I. These factors will permit the inventors to make the best assessment of the anti-tumor efficacy of this agent. A potential disadvantage of $^{131}$I is that there is a higher energy gamma emission as well which could actually expose adjacent surrounding tissues to more radiation than would occur with $^{125}$I. The tumors in the endogenous model proposed herein are peripherally located in the mammary glands and thus should not represent an immediate threat to the overall well-being of the animal. Since organ toxicity is also one of the study endpoints, the reaction of the surrounding tissue and key organ systems (marrow, liver, kidneys, bowel, brain, etc) is assessed. Tissue distribution data and actual dosimetry of radiolabeled NM404 will determine its optimal therapeutic potential. It is possible that different isotopes will complement each other in the therapeutic setting.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. REFERENCES (1) Cancer Facts and Figures. American Cancer Society 2001.
(2) Penna C, Nordlinger B. *Colorectal metastasis (liver and lung)*. Surg Clin North Am 2002; 82:1075-10xi.
(3) Fong Y, Fortner J, Sun R L, Brennan M F, Blumgart L H. Clinical score for predicting recurrence after hepatic resection for metastatic colorectal cancer: analysis of 1001 consecutive cases. Ann Surg 1999; 230:309-318.
(4) Ike H, Shimada H, Ohki S, Togo S, Yamaguchi S, Ichikawa Y. Results of aggressive resection of lung metastases from colorectal carcinoma detected by intensive follow-up. Dis Colon Rectum 2002; 45:468-473.
(5) O'Dwyer P J, Stevenson J P, Haller D G, Rotman N, Giantonio B J. *Follow-up of stage B and C colorectal cancer in the United States and France*. Seminars in Oncology 2001; 28:Suppl-9.
(6) Wichmann M W, Lau-Werner U, Muller C, Hornung H M, Stieber P, Schildberg F W, The Colorectal Cancer Study Group. Carcinoembryonic antigen for the detection of recurrent disease following curative resection of colorectal cancer. Anticancer Research 2000; 20:4953-4955.
(7) Lencioni R, Cioni D, Bartolozzi C, Percutaneous radiofrequency thermal ablation of liver malignancies: techniques, indications, imaging findings, and clinical results, Abdom Imaging 2001; 26:345-360.
(8) Curley S A, Izzo F, Delrio P, et al. Radiofrequency ablation of unresectable primary and metastatic hepatic malignancies: Results in 123 patients. Ann Surg 1999;230:1-8.
(9) Solbiati L, Livraghi T, Goldberg S N, et al. Percutaneous radio-frequency ablation of hepatic metastases from colorectal cancer: long-term results in 117 patients. Radiology 2001;221:159-166.
(10) Saltz L B, Cox J V, Blanke C, Rosen L S, Fehrenbacher L, Moore M J, Maroun J A, Ackland S P, Locker P K, Pirotta N, Elfring G L, Miller L L. *Irinotecan plus fluorouracil and leucovorin for metastatic colorectal cancer. Irinotecan Study Group*. N Engl J Med 2000; 343:905-914.
(11) De Gramont A, Bosset J F, Milan C, Rougier P, Bouche O, Etienne P L, Morvan F, Louvet C, Guillot T, Francois E, Bedenne L. Randomized trial comparing monthly low-dose leucovorin and fluorouracil bolus with bimonthly high-dose leucovorin and fluorouracil bolus plus continuous infusion for advanced colorectal cancer: a French intergroup study. J Clin Oncol 1997; 15:808-815.
(12) Modulation of fluorouracil by leucovorin in patients with advanced colorectal cancer: evidence in terms of response rate. Advanced Colorectal Cancer Meta-Analysis Project. J Clin Oncol 1992; 10:896-903.
(13) Giacchetti S, Perpoint B, Zidani R, Le Bail N, Faggiuolo R, Focan C, Chollet P, Llory J F, Letourneau Y, Coudert B, Bertheaut-Cvitkovic F, Larregain-Fournier D, Le Rol A, Walter S, Adam R, Misset J L, Levi F. *Phase III multicenter randomized trial of oxaliplatin added to chronomodulated fluorouracil-leucovorin as first-line treatment of metastatic colorectal cancer*. Journal of Clinical Oncology 2000; 18:136-147.
(14) Mayr N A. Taoka T. Yuh W T, et al. Method and timing of tumor volume measurement for outcome prediction in cervical cancer using magnetic resonance imaging. International Journal of Radiation Oncology, Biology, Physics 2002; 52;1:14-22.
(15) Greven K. Williams D. Keyes J, et al. Can positron emission tomography distinguish tumor recurrence from irradiation sequelae in patients treated for larynx cancer? Cancer Journal Scientifica American 1997;3:353-357.
(16) Snyder F, Wood R. Alkyl and alk-1-enyl ethers of glycerol in lipids from normal and neoplastic human tissues. Cancer Research. 1969; 29:251-257.
(17) Snyder F, Blank M L, Morris H P. Occurrence and nature of o-alkyl and o-alkyl-l-enyl moieties of glycerol in lipids of Morris transplanted hepatomas and normal rat livers. *Biochem Biophys Acta*. 1969; 176: 502-510.
(18) Rampy M A, Pinchuk A N, Weichert J P, Skinner R W, Fisher S J, Wahl R L, Gross M D, Counsell R E. *Synthesis and biological evaluation of radioiodinated phospholipid ether stereoisomers*. J Med Chem. 1995; 38:33156-3 162.
(19) Weichert J P, Van Dort M E, Groziak M P, Counsell R E. *Radioiodination via isotope exchange in pivalic acid*. Int J Appl Rad Isotopes. 1986; 37.907-913.
(20) Plotzke K P, Haradahira T, Stancato L, Olken N M, Skinner S, Gross M D, Wahl R L, Counsell R E. *Selective localization of radioiodinated alkylphosphocholine derivatives in tumors*. Int J RadPart B, Nucl Med & Biology. 1992; 79(7):765-773.
(21) Plotzke K P, Fisher S J, Wahl R L, Olken N M, Skinner S, Gross M D, Counsell R E. *Selective localization of a radioiodinated phospholipid ether analog in human tumorxenografts*. J Nucl Med. 1993; 34(5):787-792.
(22) Rampy M A, Brown R S, Pinchuk A N, Weichert J P, Skinner R W, Fisher S J, Wahl R L, Gross M D, Ethier S P, Counsell R E. *Biological disposition and imaging of a radioiodinated alkylphosphocholine in two rodent models of breast cancer*. J Nucl Med. 1996; 37(9):1540-1545.
(23) Arthur G, Bittman R. The inhibition of cell signaling pathways by antitumor ether lipids. Biochim Biophys Acta. 1998; 1390:85-102.
(24) Counsell R E, Longino M, Pinchuk A, Skinner S, Weichert J. *Synthesis and evaluation of radioiodinated phospholipid ethers for imaging of prostate cancer*. Quart J Nucl Med. 1997; 41(suppl 1):14-16.
(25) Weber S M, Shi F, Heise C, Warner T, Mahvi D M. Interleukin-12 gene transfer results in CD8-dependent regression of murine CT26 liver tumors. Ann Surg Oncol 1999; 6:186-194.
(26) Imboden M, Murphy K R, Rakhmilevich A L, Neal Z C, Xiang R, Reisfeld R A, Gillies S D, Sondel P M. The level of MHC class I expression on murine adenocarcinoma can change the antitumor effector mechanism of immunocytokine therapy. Cancer Res 2001; 61:1500-1507.
(27) Weichert J P, Longino M A, Bakan D A, Spigarelli M G, Chou T, Schwendner S W, Counsell R E. *Polyiodinated Triglyceride Analogs as Potential CT Imaging Agents for the Liver*. J Med Chem 1995; 38:636-646.
(28) *Rodent Tumor Models In Experimental Cancer Therapy*, Robert F Kallman ed, Pergamon Press, New York, pp 111-132, 1987.

"DIAPEUTIC" is a trademark of Cellectar, LLC

What is claimed is:

1. A method for the treatment of a cancer in a subject comprising administering to the subject an effective amount of a molecule comprising a phospholipid ether analog, wherein the phospholipid ether analog is 18-(p-iodophenyl) octadecyl phosphocholine wherein the iodo moiety of the 18-(p-iodophenyl)octadecyl phosphocholine is $^{125}$I or $^{131}$I, and wherein said cancer is selected from the group consisting of lung cancer, squamous cell carcinoma, melanoma, colorectal cancer, ovarian cancer, prostate cancer, glioma, breast cancer, carcinosarcoma, and pancreatic cancer.

2. The method of claim 1, wherein the radioactive isotope of iodine is $^{131}$I.

3. The method of claim 1, further comprising administering 5-20 µCi/200 g of body weight of the phospholipid ether analog to the subject.

4. The method of claim 1, further comprising administering 15-20 µCi/200 g of body weight of the phospholipid ether analog to the subject.

5. The method of claim 1, wherein the radioactive isotope of iodine is $^{125}$I.

* * * * *